United States Patent
Rybnikov et al.

(10) Patent No.: US 12,412,346 B2
(45) Date of Patent: *Sep. 9, 2025

(54) METHODS FOR MEDICAL IMAGE VISUALIZATION

(71) Applicant: AUGMEDICS LTD., Yokneam Illit (IL)

(72) Inventors: Silvina Rybnikov, Zichron Ya'akov (IL); Gal Bar-Zohar, Yokneam Hamoshava (IL); Nissan Elimelech, Be'erotaim (IL); Yotam Portal, Kiryat Motzkin (IL)

(73) Assignee: AUGMEDICS LTD., Yokneam Illit (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/399,253

(22) Filed: Dec. 28, 2023

(65) Prior Publication Data

US 2024/0127559 A1 Apr. 18, 2024

Related U.S. Application Data

(63) Continuation of application No. 18/365,566, filed on Aug. 4, 2023, which is a continuation of application No. PCT/IB2023/054056, filed on Apr. 20, 2023.
(Continued)

(51) Int. Cl.
*G06T 19/00* (2011.01)
(52) U.S. Cl.
CPC ........ *G06T 19/006* (2013.01); *G06T 2210/41* (2013.01)

(58) Field of Classification Search
None
See application file for complete search history.

(56) References Cited

U.S. PATENT DOCUMENTS

| 3,101,715 A | 8/1963 | Glassman |
| 3,690,776 A | 9/1972 | Zaporoshan |

(Continued)

FOREIGN PATENT DOCUMENTS

| CA | 3022448 A1 | 2/2018 |
| CA | 3034314 A1 | 2/2018 |

(Continued)

OTHER PUBLICATIONS

U.S. Appl. No. 15/896,102 (U.S. Pat. No. 10,134,166), filed Feb. 14, 2018 (Nov. 20, 2018), Combining Video-Based and Optic-Based Augmented Reality in a Near Eye Display.
(Continued)

*Primary Examiner* — Nicholas R Wilson
(74) *Attorney, Agent, or Firm* — Dinsmore & Shohl LLP

(57) ABSTRACT

A computer-implemented method includes obtaining a three-dimensional (3D) image of a region of a body of a patient, the 3D image having feature values. The 3D image is segmented to define one or more regions of interest (ROIs). At least one region of interest (ROI) feature threshold is determined. A background feature threshold is determined. A 3D model is generated from the 3D image based on the determined at least one ROI feature threshold, the determined background feature threshold, and the segmentation. The 3D model is output for display to a user.

20 Claims, 7 Drawing Sheets

Related U.S. Application Data

(60) Provisional application No. 63/428,781, filed on Nov. 30, 2022, provisional application No. 63/333,128, filed on Apr. 21, 2022.

(56) References Cited

U.S. PATENT DOCUMENTS

| | | |
|---|---|---|
| 4,459,358 A | 7/1984 | Berke |
| 4,711,512 A | 12/1987 | Upatnieks |
| 4,863,238 A | 9/1989 | Brewster |
| 4,944,739 A | 7/1990 | Torre |
| 5,100,420 A | 3/1992 | Green et al. |
| 5,147,365 A | 9/1992 | Whitlock et al. |
| 5,357,292 A | 10/1994 | Wiedner |
| 5,410,802 A | 5/1995 | Buckley |
| 5,441,042 A | 8/1995 | Putman |
| 5,442,146 A | 8/1995 | Bell et al. |
| 5,510,832 A | 4/1996 | Garcia |
| D370,309 S | 5/1996 | Stucky |
| 5,620,188 A | 4/1997 | Mccurry et al. |
| 5,636,255 A | 6/1997 | Ellis |
| 5,665,092 A | 9/1997 | Mangiardi et al. |
| 5,743,731 A | 4/1998 | Lares et al. |
| 5,771,121 A | 6/1998 | Hentschke |
| 5,792,046 A | 8/1998 | Dobrovolny |
| 5,841,507 A | 11/1998 | Barnes |
| 6,006,126 A | 12/1999 | Cosman |
| 6,038,467 A | 3/2000 | De Bliek et al. |
| 6,125,164 A | 9/2000 | Murphy et al. |
| 6,138,530 A | 10/2000 | McClure |
| 6,147,805 A | 11/2000 | Fergason |
| 6,227,667 B1 | 5/2001 | Halldorsson et al. |
| 6,256,529 B1 | 7/2001 | Holupka et al. |
| 6,285,505 B1 | 9/2001 | Melville et al. |
| 6,314,310 B1 | 11/2001 | Ben-Haim et al. |
| 6,349,001 B1 | 2/2002 | Spitzer |
| 6,444,192 B1 | 9/2002 | Mattrey |
| 6,447,503 B1 | 9/2002 | Wynne et al. |
| 6,449,090 B1 | 9/2002 | Omar et al. |
| 6,456,405 B2 | 9/2002 | Horikoshi et al. |
| 6,456,868 B2 | 9/2002 | Saito et al. |
| 6,474,159 B1 | 11/2002 | Foxlin et al. |
| 6,518,939 B1 | 2/2003 | Kikuchi |
| 6,527,777 B2 | 3/2003 | Justin |
| 6,529,331 B2 | 3/2003 | Massof et al. |
| 6,549,645 B1 | 4/2003 | Oikawa et al. |
| 6,578,962 B1 | 6/2003 | Amir et al. |
| 6,609,022 B2 | 8/2003 | Vilsmeier et al. |
| 6,610,009 B2 | 8/2003 | Person |
| D480,476 S | 10/2003 | Martinson et al. |
| 6,659,611 B2 | 12/2003 | Amir et al. |
| 6,675,040 B1 | 1/2004 | Cosman |
| 6,683,584 B2 | 1/2004 | Ronzani et al. |
| 6,690,964 B2 | 2/2004 | Bieger et al. |
| 6,714,810 B2 | 3/2004 | Grzeszczuk et al. |
| 6,737,425 B1 | 5/2004 | Yamamoto et al. |
| 6,740,882 B2 | 5/2004 | Weinberg |
| 6,757,068 B2 | 6/2004 | Foxlin |
| 6,759,200 B1 | 7/2004 | Stanton, Jr. |
| 6,847,336 B1 | 1/2005 | Lemelson et al. |
| 6,856,324 B2 | 2/2005 | Sauer et al. |
| 6,856,826 B2 | 2/2005 | Seeley et al. |
| 6,891,518 B2 | 5/2005 | Sauer et al. |
| 6,900,777 B1 | 5/2005 | Hebert et al. |
| 6,919,867 B2 | 7/2005 | Sauer |
| 6,921,167 B2 | 7/2005 | Nagata |
| 6,966,668 B2 | 11/2005 | Cugini et al. |
| 6,980,849 B2 | 12/2005 | Sasso |
| 6,993,374 B2 | 1/2006 | Sasso |
| 6,997,552 B1 | 2/2006 | Hung |
| 6,999,239 B1 | 2/2006 | Martins et al. |
| 7,000,262 B2 | 2/2006 | Bielefeld |
| 7,035,371 B2 | 4/2006 | Boese et al. |
| 7,043,961 B2 | 5/2006 | Pandey et al. |
| 7,072,435 B2 | 7/2006 | Metz et al. |
| 7,103,233 B2 | 9/2006 | Stearns |
| 7,107,091 B2 | 9/2006 | Jutras et al. |
| 7,112,656 B2 | 9/2006 | Desnoyers et al. |
| 7,141,812 B2 | 11/2006 | Appleby et al. |
| 7,157,459 B2 | 1/2007 | Ohta et al. |
| 7,169,785 B2 | 1/2007 | Timmer et al. |
| 7,171,255 B2 | 1/2007 | Holupka et al. |
| 7,176,936 B2 | 2/2007 | Sauer et al. |
| 7,187,792 B2 | 3/2007 | Fu et al. |
| 7,190,331 B2 | 3/2007 | Genc et al. |
| 7,194,295 B2 | 3/2007 | Vilsmeier |
| 7,215,322 B2 | 5/2007 | Genc et al. |
| 7,229,078 B2 | 6/2007 | Lechot |
| 7,231,076 B2 | 6/2007 | Fu et al. |
| 7,235,076 B2 | 6/2007 | Pacheco |
| 7,239,330 B2 | 7/2007 | Sauer et al. |
| 7,241,292 B2 | 7/2007 | Hooven |
| 7,259,266 B2 | 8/2007 | Carter et al. |
| 7,260,426 B2 | 8/2007 | Schweikard et al. |
| 7,269,192 B2 | 9/2007 | Hayashi |
| 7,281,826 B2 | 10/2007 | Huang |
| 7,315,636 B2 | 1/2008 | Kuduvalli |
| 7,320,556 B2 | 1/2008 | Vagn-Erik |
| 7,330,578 B2 | 2/2008 | Wang et al. |
| 7,359,535 B2 | 4/2008 | Salla et al. |
| 7,364,314 B2 | 4/2008 | Nilsen et al. |
| 7,366,934 B1 | 4/2008 | Narayan et al. |
| 7,379,077 B2 | 5/2008 | Bani-Hashemi et al. |
| 7,431,453 B2 | 10/2008 | Hogan |
| 7,435,219 B2 | 10/2008 | Kim |
| 7,450,743 B2 | 11/2008 | Sundar et al. |
| 7,458,977 B2 | 12/2008 | McGinley et al. |
| 7,462,852 B2 | 12/2008 | Appleby et al. |
| 7,493,153 B2 | 2/2009 | Ahmed et al. |
| 7,505,617 B2 | 3/2009 | Fu et al. |
| 7,507,968 B2 | 3/2009 | Wollenweber et al. |
| 7,518,136 B2 | 4/2009 | Appleby et al. |
| 7,525,735 B2 | 4/2009 | Sottilare et al. |
| D592,691 S | 5/2009 | Chang |
| D592,692 S | 5/2009 | Chang |
| D592,693 S | 5/2009 | Chang |
| 7,536,216 B2 | 5/2009 | Geiger et al. |
| 7,542,791 B2 | 6/2009 | Mire et al. |
| 7,556,428 B2 | 7/2009 | Sukovic et al. |
| 7,557,824 B2 | 7/2009 | Holliman |
| 7,563,228 B2 | 7/2009 | Ma et al. |
| 7,567,834 B2 | 7/2009 | Clayton et al. |
| 7,570,791 B2 | 8/2009 | Frank et al. |
| 7,586,686 B1 | 9/2009 | Hall |
| D602,620 S | 10/2009 | Cristoforo |
| 7,605,826 B2 | 10/2009 | Sauer |
| 7,606,613 B2 | 10/2009 | Simon et al. |
| 7,607,775 B2 | 10/2009 | Hermanson et al. |
| 7,620,223 B2 | 11/2009 | Xu et al. |
| 7,623,902 B2 | 11/2009 | Pacheco |
| 7,627,085 B2 | 12/2009 | Boyden et al. |
| 7,630,753 B2 | 12/2009 | Simon et al. |
| 7,633,501 B2 | 12/2009 | Wood et al. |
| 7,645,050 B2 | 1/2010 | Wilt et al. |
| 7,653,226 B2 | 1/2010 | Guhring et al. |
| 7,657,075 B2 | 2/2010 | Viswanathan |
| 7,689,019 B2 | 3/2010 | Boese et al. |
| 7,689,042 B2 | 3/2010 | Brunner et al. |
| 7,689,320 B2 | 3/2010 | Prisco et al. |
| 7,699,486 B1 | 4/2010 | Beiner |
| 7,699,793 B2 | 4/2010 | Goette et al. |
| 7,719,769 B2 | 5/2010 | Sugihara et al. |
| D617,825 S | 6/2010 | Chang |
| 7,734,327 B2 | 6/2010 | Colquhoun |
| D619,285 S | 7/2010 | Cristoforo |
| 7,751,865 B2 | 7/2010 | Jascob et al. |
| 7,758,204 B2 | 7/2010 | Klipstein et al. |
| 7,768,702 B2 | 8/2010 | Hirose et al. |
| 7,769,236 B2 | 8/2010 | Fiala |
| 7,773,074 B2 | 8/2010 | Arenson et al. |
| 7,774,044 B2 | 8/2010 | Sauer et al. |
| 7,822,483 B2 | 10/2010 | Stone et al. |
| D628,307 S | 11/2010 | Krause-Bonte |
| 7,826,902 B2 | 11/2010 | Stone et al. |

(56) References Cited

U.S. PATENT DOCUMENTS

| | | |
|---|---|---|
| 7,831,073 B2 | 11/2010 | Fu et al. |
| 7,831,096 B2 | 11/2010 | Williamson, Jr. |
| 7,835,778 B2 | 11/2010 | Foley et al. |
| 7,835,784 B2 | 11/2010 | Mire et al. |
| 7,837,987 B2 | 11/2010 | Shi et al. |
| 7,840,093 B2 | 11/2010 | Fu et al. |
| 7,840,253 B2 | 11/2010 | Tremblay et al. |
| 7,840,256 B2 | 11/2010 | Lakin et al. |
| 7,853,305 B2 | 12/2010 | Simon et al. |
| 7,854,705 B2 | 12/2010 | Pawluczyk et al. |
| 7,857,271 B2 | 12/2010 | Lees |
| 7,860,282 B2 | 12/2010 | Boese et al. |
| D630,766 S | 1/2011 | Harbin |
| 7,865,269 B2 | 1/2011 | Prisco et al. |
| 7,874,686 B2 | 1/2011 | Rossner et al. |
| 7,881,770 B2 | 2/2011 | Melkent et al. |
| 7,893,413 B1 | 2/2011 | Appleby et al. |
| 7,894,649 B2 | 2/2011 | Fu et al. |
| 7,920,162 B2 | 4/2011 | Masini et al. |
| 7,922,391 B2 | 4/2011 | Essenreiter et al. |
| 7,938,553 B1 | 5/2011 | Beiner |
| 7,945,310 B2 | 5/2011 | Gattani et al. |
| 7,953,471 B2 | 5/2011 | Clayton et al. |
| 7,969,383 B2 | 6/2011 | Eberl et al. |
| 7,974,677 B2 | 7/2011 | Mire et al. |
| 7,985,756 B2 | 7/2011 | Barlow et al. |
| 7,991,557 B2 | 8/2011 | Liew et al. |
| 7,993,353 B2 | 8/2011 | Roner et al. |
| 7,996,064 B2 | 8/2011 | Simon et al. |
| 8,004,524 B2 | 8/2011 | Deinzer |
| 8,021,300 B2 | 9/2011 | Ma et al. |
| 8,022,984 B2 | 9/2011 | Cheong et al. |
| 8,045,266 B2 | 10/2011 | Nakamura |
| 8,060,181 B2 | 11/2011 | Rodriguez et al. |
| 8,068,581 B2 | 11/2011 | Boese et al. |
| 8,068,896 B2 | 11/2011 | Daghighian et al. |
| 8,077,943 B2 | 12/2011 | Williams et al. |
| 8,079,957 B2 | 12/2011 | Ma et al. |
| 8,081,812 B2 | 12/2011 | Kreiser |
| 8,085,075 B2 | 12/2011 | Huffman et al. |
| 8,085,897 B2 | 12/2011 | Morton |
| 8,090,175 B2 | 1/2012 | Fu et al. |
| 8,092,400 B2 | 1/2012 | Warkentine et al. |
| 8,108,072 B2 | 1/2012 | Zhao et al. |
| 8,112,292 B2 | 2/2012 | Simon |
| 8,116,847 B2 | 2/2012 | Gattani et al. |
| 8,120,847 B2 | 2/2012 | Chang |
| 8,121,255 B2 | 2/2012 | Sugiyama |
| 8,155,479 B2 | 4/2012 | Hoffman et al. |
| 8,180,132 B2 | 5/2012 | Gorges et al. |
| 8,180,429 B2 | 5/2012 | Sasso |
| 8,208,599 B2 | 6/2012 | Ye et al. |
| 8,216,211 B2 | 7/2012 | Mathis et al. |
| 8,221,402 B2 | 7/2012 | Francischelli et al. |
| 8,239,001 B2 | 8/2012 | Verard et al. |
| 8,244,012 B2 | 8/2012 | Liang et al. |
| 8,253,778 B2 | 8/2012 | Atsushi |
| 8,271,069 B2 | 9/2012 | Jascob et al. |
| 8,280,491 B2 | 10/2012 | Kuduvalli et al. |
| 8,285,021 B2 | 10/2012 | Boese et al. |
| 8,300,315 B2 | 10/2012 | Kobayashi |
| 8,305,685 B2 | 11/2012 | Heine et al. |
| 8,306,305 B2 | 11/2012 | Porat et al. |
| 8,309,932 B2 | 11/2012 | Haselman et al. |
| 8,317,320 B2 | 11/2012 | Huang |
| 8,328,815 B2 | 12/2012 | Farr et al. |
| 8,335,553 B2 | 12/2012 | Rubner et al. |
| 8,335,557 B2 | 12/2012 | Maschke |
| 8,340,379 B2 | 12/2012 | Razzaque et al. |
| 8,369,925 B2 | 2/2013 | Giesel et al. |
| 8,386,022 B2 | 2/2013 | Jutras et al. |
| 8,394,144 B2 | 3/2013 | Zehavi et al. |
| 8,398,541 B2 | 3/2013 | Dimaio et al. |
| 8,444,266 B2 | 5/2013 | Waters |
| 8,457,719 B2 | 6/2013 | Moctezuma De La Barrera et al. |
| 8,467,851 B2 | 6/2013 | Mire et al. |
| 8,469,902 B2 | 6/2013 | Dick et al. |
| 8,475,470 B2 | 7/2013 | Von Jako |
| 8,494,612 B2 | 7/2013 | Vetter et al. |
| 8,509,503 B2 | 8/2013 | Nahum et al. |
| 8,511,827 B2 | 8/2013 | Hua et al. |
| 8,531,394 B2 | 9/2013 | Maltz |
| 8,540,364 B2 | 9/2013 | Waters |
| 8,545,012 B2 | 10/2013 | Waters |
| 8,548,567 B2 | 10/2013 | Maschke et al. |
| 8,556,883 B2 | 10/2013 | Saleh |
| 8,559,596 B2 | 10/2013 | Thomson et al. |
| 8,567,945 B2 | 10/2013 | Waters |
| 8,571,353 B2 | 10/2013 | Watanabe |
| 8,585,598 B2 | 11/2013 | Razzaque et al. |
| 8,600,001 B2 | 12/2013 | Schweizer |
| 8,600,477 B2 | 12/2013 | Beyar et al. |
| 8,605,199 B2 | 12/2013 | Imai |
| 8,611,988 B2 | 12/2013 | Miyamoto |
| 8,612,024 B2 | 12/2013 | Stone et al. |
| 8,634,897 B2 | 1/2014 | Simon et al. |
| 8,641,621 B2 | 2/2014 | Razzaque et al. |
| 8,643,950 B2 | 2/2014 | König |
| 8,644,907 B2 | 2/2014 | Hartmann et al. |
| 8,674,902 B2 | 3/2014 | Park et al. |
| 8,686,923 B2 | 4/2014 | Eberl et al. |
| 8,690,581 B2 | 4/2014 | Ruf et al. |
| 8,690,776 B2 | 4/2014 | Razzaque et al. |
| 8,692,845 B2 | 4/2014 | Fedorovskaya et al. |
| 8,693,632 B2 | 4/2014 | Allison |
| 8,694,075 B2 | 4/2014 | Groszmann et al. |
| 8,699,765 B2 | 4/2014 | Hao et al. |
| 8,705,829 B2 | 4/2014 | Frank et al. |
| 8,737,708 B2 | 5/2014 | Hartmann et al. |
| 8,746,887 B2 | 6/2014 | Shestak et al. |
| 8,764,025 B1 | 7/2014 | Gao |
| 8,784,450 B2 | 7/2014 | Moskowitz et al. |
| 8,786,689 B1 | 7/2014 | Liu |
| D710,545 S | 8/2014 | Wu |
| D710,546 S | 8/2014 | Wu |
| 8,827,934 B2 | 9/2014 | Chopra et al. |
| 8,831,706 B2 | 9/2014 | Fu et al. |
| 8,836,768 B1 | 9/2014 | Rafii et al. |
| 8,838,199 B2 | 9/2014 | Simon et al. |
| 8,848,977 B2 | 9/2014 | Bammer et al. |
| 8,855,395 B2 | 10/2014 | Baturin et al. |
| 8,878,900 B2 | 11/2014 | Yang et al. |
| 8,879,815 B2 | 11/2014 | Miao et al. |
| 8,885,177 B2 | 11/2014 | Ben-Yishai et al. |
| 8,890,772 B2 | 11/2014 | Woo et al. |
| 8,890,773 B1 | 11/2014 | Pederson |
| 8,890,943 B2 | 11/2014 | Lee et al. |
| 8,897,514 B2 | 11/2014 | Feikas et al. |
| 8,900,131 B2 | 12/2014 | Chopra et al. |
| 8,903,150 B2 | 12/2014 | Star-Lack et al. |
| 8,908,952 B2 | 12/2014 | Isaacs et al. |
| 8,911,358 B2 | 12/2014 | Koninckx et al. |
| 8,917,268 B2 | 12/2014 | Johnsen et al. |
| 8,920,776 B2 | 12/2014 | Gaiger et al. |
| 8,922,589 B2 | 12/2014 | Laor |
| 8,941,559 B2 | 1/2015 | Bar-Zeev et al. |
| 8,942,455 B2 | 1/2015 | Chou et al. |
| 8,950,877 B2 | 2/2015 | Northey et al. |
| 8,953,246 B2 | 2/2015 | Koenig |
| 8,961,500 B2 | 2/2015 | Dicorleto et al. |
| 8,965,583 B2 | 2/2015 | Ortmaier et al. |
| 8,969,829 B2 | 3/2015 | Wollenweber et al. |
| 8,989,349 B2 | 3/2015 | Thomson et al. |
| 8,992,580 B2 | 3/2015 | Bar et al. |
| 8,994,729 B2 | 3/2015 | Nakamura |
| 8,994,795 B2 | 3/2015 | Oh |
| 9,004,711 B2 | 4/2015 | Gerolemou |
| 9,005,211 B2 | 4/2015 | Brundobler et al. |
| 9,011,441 B2 | 4/2015 | Bertagnoli et al. |
| 9,057,759 B2 | 6/2015 | Klingenbeck et al. |
| 9,060,757 B2 | 6/2015 | Lawson et al. |
| 9,066,751 B2 | 6/2015 | Sasso |
| 9,081,436 B1 | 7/2015 | Berme et al. |
| 9,084,635 B2 | 7/2015 | Nuckley et al. |

(56) References Cited

U.S. PATENT DOCUMENTS

| | | |
|---|---|---|
| 9,085,643 B2 | 7/2015 | Svanborg et al. |
| 9,087,471 B2 | 7/2015 | Miao |
| 9,100,643 B2 | 8/2015 | McDowall et al. |
| 9,101,394 B2 | 8/2015 | Arata et al. |
| 9,104,902 B2 | 8/2015 | Xu et al. |
| 9,111,175 B2 | 8/2015 | Strommer et al. |
| 9,123,155 B2 | 9/2015 | Cunningham et al. |
| 9,125,556 B2 | 9/2015 | Zehavi et al. |
| 9,129,054 B2 | 9/2015 | Nawana et al. |
| 9,129,372 B2 | 9/2015 | Kriston et al. |
| 9,132,361 B2 | 9/2015 | Smithwick |
| 9,135,706 B2 | 9/2015 | Zagorchev et al. |
| 9,141,873 B2 | 9/2015 | Takemoto |
| 9,142,020 B2 | 9/2015 | Deguise et al. |
| 9,149,317 B2 | 10/2015 | Arthur et al. |
| 9,165,203 B2 | 10/2015 | McCarthy |
| 9,165,362 B2 | 10/2015 | Siewerdsen et al. |
| 9,179,984 B2 | 11/2015 | Teichman et al. |
| D746,354 S | 12/2015 | Chang |
| 9,208,916 B2 | 12/2015 | Appleby et al. |
| 9,220,573 B2 | 12/2015 | Kendrick et al. |
| 9,225,895 B2 | 12/2015 | Kozinski |
| 9,232,982 B2 | 1/2016 | Soler et al. |
| 9,235,934 B2 | 1/2016 | Mandella et al. |
| 9,240,046 B2 | 1/2016 | Carrell et al. |
| 9,244,278 B2 | 1/2016 | Sugiyama et al. |
| 9,247,240 B2 | 1/2016 | Park et al. |
| 9,259,192 B2 | 2/2016 | Ishihara |
| 9,265,572 B2 | 2/2016 | Fuchs et al. |
| 9,269,192 B2 | 2/2016 | Kobayashi |
| 9,283,052 B2 | 3/2016 | Rodriguez Ponce |
| 9,286,730 B2 | 3/2016 | Bar-Zeev et al. |
| 9,289,267 B2 | 3/2016 | Sauer et al. |
| 9,294,222 B2 | 3/2016 | Proctor, Jr. |
| 9,300,949 B2 | 3/2016 | Ahearn |
| 9,305,354 B2 | 4/2016 | Burlon et al. |
| 9,310,591 B2 | 4/2016 | Hua et al. |
| 9,320,474 B2 | 4/2016 | Demri et al. |
| 9,323,055 B2 | 4/2016 | Baillot |
| 9,330,477 B2 | 5/2016 | Rappel |
| 9,335,547 B2 | 5/2016 | Takano et al. |
| 9,335,567 B2 | 5/2016 | Nakamura |
| 9,341,704 B2 | 5/2016 | Picard et al. |
| 9,344,686 B2 | 5/2016 | Moharir |
| 9,349,066 B2 | 5/2016 | Koo et al. |
| 9,349,520 B2 | 5/2016 | Demetriou et al. |
| 9,364,294 B2 | 6/2016 | Razzaque et al. |
| 9,370,332 B2 | 6/2016 | Paladini et al. |
| 9,373,166 B2 | 6/2016 | Azar |
| 9,375,639 B2 | 6/2016 | Kobayashi et al. |
| 9,378,558 B2 | 6/2016 | Kajiwara et al. |
| 9,380,287 B2 | 6/2016 | Nistico et al. |
| 9,387,008 B2 | 7/2016 | Sarvestani et al. |
| 9,392,129 B2 | 7/2016 | Simmons |
| 9,395,542 B2 | 7/2016 | Tilleman et al. |
| 9,398,936 B2 | 7/2016 | Razzaque et al. |
| 9,400,384 B2 | 7/2016 | Griffith |
| 9,414,041 B2 | 8/2016 | Ko et al. |
| 9,424,611 B2 | 8/2016 | Kanjirathinkal et al. |
| 9,424,641 B2 | 8/2016 | Wiemker et al. |
| 9,427,286 B2 | 8/2016 | Siewerdsen et al. |
| 9,438,894 B2 | 9/2016 | Park et al. |
| 9,443,488 B2 | 9/2016 | Borenstein et al. |
| 9,453,804 B2 | 9/2016 | Tahtali |
| 9,456,878 B2 | 10/2016 | MacFarlane et al. |
| 9,465,235 B2 | 10/2016 | Chang |
| 9,468,373 B2 | 10/2016 | Larsen |
| 9,470,908 B1 | 10/2016 | Frankel et al. |
| 9,473,766 B2 | 10/2016 | Douglas et al. |
| 9,492,222 B2 | 11/2016 | Singh |
| 9,495,585 B2 | 11/2016 | Bicer et al. |
| 9,498,132 B2 | 11/2016 | Maier-Hein et al. |
| 9,498,231 B2 | 11/2016 | Haider et al. |
| 9,499,999 B2 | 11/2016 | Nanqing |
| 9,507,155 B2 | 11/2016 | Morimoto |
| 9,513,495 B2 | 12/2016 | Waters |
| 9,521,966 B2 | 12/2016 | Schwartz |
| 9,526,443 B1 | 12/2016 | Berme et al. |
| 9,530,382 B2 | 12/2016 | Simmons |
| 9,532,846 B2 | 1/2017 | Nakamura |
| 9,532,849 B2 | 1/2017 | Anderson et al. |
| 9,533,407 B1 | 1/2017 | Ragner |
| 9,538,962 B1 | 1/2017 | Hannaford et al. |
| 9,545,233 B2 | 1/2017 | Sirpad et al. |
| 9,546,779 B2 | 1/2017 | Rementer |
| 9,547,174 B2 | 1/2017 | Gao et al. |
| 9,547,940 B1 | 1/2017 | Sun et al. |
| 9,557,566 B2 | 1/2017 | Fujimaki |
| 9,560,318 B2 | 1/2017 | Reina et al. |
| 9,561,095 B1 | 2/2017 | Nguyen et al. |
| 9,561,446 B2 | 2/2017 | Brecher |
| 9,565,415 B2 | 2/2017 | Zhang et al. |
| 9,572,661 B2 | 2/2017 | Robin et al. |
| 9,576,398 B1 | 2/2017 | Zehner et al. |
| 9,576,556 B2 | 2/2017 | Simmons |
| 9,581,822 B2 | 2/2017 | Morimoto |
| 9,610,056 B2 | 4/2017 | Lavallee et al. |
| 9,612,657 B2 | 4/2017 | Bertram et al. |
| 9,626,936 B2 | 4/2017 | Bell |
| 9,629,595 B2 | 4/2017 | Walker et al. |
| 9,633,431 B2 | 4/2017 | Merlet |
| 9,645,395 B2 | 5/2017 | Bolas et al. |
| 9,646,423 B1 | 5/2017 | Sun et al. |
| 9,672,597 B2 | 6/2017 | Amiot et al. |
| 9,672,607 B2 | 6/2017 | Demri et al. |
| 9,672,640 B2 | 6/2017 | Kleiner |
| 9,675,306 B2 | 6/2017 | Morton |
| 9,675,319 B1 | 6/2017 | Razzaque et al. |
| 9,684,980 B2 | 6/2017 | Royalty et al. |
| 9,690,119 B2 | 6/2017 | Garofolo et al. |
| RE46,463 E | 7/2017 | Fienbloom et al. |
| 9,693,748 B2 | 7/2017 | Rai et al. |
| 9,710,968 B2 | 7/2017 | Dillavou et al. |
| 9,713,502 B2 | 7/2017 | Finkman et al. |
| 9,724,119 B2 | 8/2017 | Hissong et al. |
| 9,724,165 B2 | 8/2017 | Arata et al. |
| 9,726,888 B2 | 8/2017 | Giartosio et al. |
| 9,728,006 B2 | 8/2017 | Varga |
| 9,729,831 B2 | 8/2017 | Birnkrant et al. |
| 9,746,739 B2 | 8/2017 | Alton et al. |
| 9,757,034 B2 | 9/2017 | Desjardins et al. |
| 9,757,087 B2 | 9/2017 | Simon et al. |
| 9,766,441 B2 | 9/2017 | Rappel |
| 9,766,459 B2 | 9/2017 | Alton et al. |
| 9,767,608 B2 | 9/2017 | Lee et al. |
| 9,770,203 B1 | 9/2017 | Berme et al. |
| 9,772,102 B1 | 9/2017 | Ferguson |
| 9,772,495 B2 | 9/2017 | Tam et al. |
| 9,791,138 B1 | 10/2017 | Feinbloom et al. |
| 9,800,995 B2 | 10/2017 | Libin et al. |
| 9,805,504 B2 | 10/2017 | Zhang et al. |
| 9,808,148 B2 | 11/2017 | Miller et al. |
| 9,839,448 B2 | 12/2017 | Reckling et al. |
| 9,844,413 B2 | 12/2017 | Daon et al. |
| 9,851,080 B2 | 12/2017 | Wilt et al. |
| 9,858,663 B2 | 1/2018 | Penney et al. |
| 9,861,446 B2 | 1/2018 | Lang |
| 9,864,214 B2 | 1/2018 | Fass |
| 9,872,733 B2 | 1/2018 | Shoham et al. |
| 9,875,544 B2 | 1/2018 | Rai et al. |
| 9,877,642 B2 | 1/2018 | Duret |
| 9,885,465 B2 | 2/2018 | Nguyen |
| 9,886,552 B2 | 2/2018 | Dillavou et al. |
| 9,886,760 B2 | 2/2018 | Liu et al. |
| 9,892,564 B1 | 2/2018 | Cvetko et al. |
| 9,898,866 B2 | 2/2018 | Fuchs et al. |
| 9,901,414 B2 | 2/2018 | Lively et al. |
| 9,911,187 B2 | 3/2018 | Steinle et al. |
| 9,911,236 B2 | 3/2018 | Bar et al. |
| 9,927,611 B2 | 3/2018 | Rudy et al. |
| 9,928,629 B2 | 3/2018 | Benishti et al. |
| 9,940,750 B2 | 4/2018 | Dillavou et al. |
| 9,943,374 B2 | 4/2018 | Merritt et al. |
| 9,947,110 B2 | 4/2018 | Haimerl |

(56) References Cited

U.S. PATENT DOCUMENTS

| | | |
|---|---|---|
| 9,952,664 B2 | 4/2018 | Border et al. |
| 9,956,054 B2 | 5/2018 | Aguirre-Valencia |
| 9,958,674 B2 | 5/2018 | Border |
| 9,959,620 B2 | 5/2018 | Merlet |
| 9,959,629 B2 | 5/2018 | Dillavou et al. |
| 9,965,681 B2 | 5/2018 | Border et al. |
| 9,968,297 B2 | 5/2018 | Connor |
| 9,980,780 B2 | 5/2018 | Lang |
| 9,986,228 B2 | 5/2018 | Woods |
| D824,523 S | 7/2018 | Paoli et al. |
| 10,010,379 B1 | 7/2018 | Gibby et al. |
| 10,013,531 B2 | 7/2018 | Richards et al. |
| 10,015,243 B2 | 7/2018 | Kazerani et al. |
| 10,016,243 B2 | 7/2018 | Esterberg |
| 10,022,064 B2 | 7/2018 | Kim et al. |
| 10,022,065 B2 | 7/2018 | Ben-Yishai et al. |
| 10,022,104 B2 | 7/2018 | Sell et al. |
| 10,023,615 B2 | 7/2018 | Bonny |
| 10,026,015 B2 | 7/2018 | Cavusoglu et al. |
| 10,034,713 B2 | 7/2018 | Yang et al. |
| 10,042,167 B2 | 8/2018 | Mcdowall et al. |
| 10,046,165 B2 | 8/2018 | Frewin et al. |
| 10,055,838 B2 | 8/2018 | Elenbaas et al. |
| 10,066,816 B2 | 9/2018 | Chang |
| 10,067,359 B1 | 9/2018 | Ushakov |
| 10,073,515 B2 | 9/2018 | Awdeh |
| 10,080,616 B2 | 9/2018 | Wilkinson et al. |
| 10,082,680 B2 | 9/2018 | Chung |
| 10,085,709 B2 | 10/2018 | Lavallee et al. |
| 10,105,187 B2 | 10/2018 | Corndorf et al. |
| 10,107,483 B2 | 10/2018 | Oren |
| 10,108,833 B2 | 10/2018 | Hong et al. |
| 10,123,840 B2 | 11/2018 | Dorman |
| 10,130,378 B2 | 11/2018 | Bryan |
| 10,132,483 B1 | 11/2018 | Feinbloom et al. |
| 10,134,166 B2 | 11/2018 | Benishti et al. |
| 10,134,194 B2 | 11/2018 | Kepner et al. |
| 10,139,652 B2 | 11/2018 | Windham |
| 10,139,920 B2 | 11/2018 | Isaacs et al. |
| 10,142,496 B1 | 11/2018 | Rao et al. |
| 10,151,928 B2 | 12/2018 | Ushakov |
| 10,154,239 B2 | 12/2018 | Casas |
| 10,159,530 B2 | 12/2018 | Lang |
| 10,163,207 B2 | 12/2018 | Merlet |
| 10,166,079 B2 | 1/2019 | McLachlin et al. |
| 10,175,507 B2 | 1/2019 | Nakamura |
| 10,175,753 B2 | 1/2019 | Boesen |
| 10,181,361 B2 | 1/2019 | Dillavou et al. |
| 10,186,055 B2 | 1/2019 | Takahashi et al. |
| 10,188,672 B2 | 1/2019 | Wagner |
| 10,194,131 B2 | 1/2019 | Casas |
| 10,194,990 B2 | 2/2019 | Amanatullah et al. |
| 10,194,993 B2 | 2/2019 | Roger et al. |
| 10,195,076 B2 | 2/2019 | Fateh |
| 10,197,803 B2 | 2/2019 | Badiali et al. |
| 10,197,816 B2 | 2/2019 | Waisman et al. |
| 10,207,315 B2 | 2/2019 | Appleby et al. |
| 10,212,517 B1 | 2/2019 | Beltran et al. |
| 10,230,719 B2 | 3/2019 | Vaughn et al. |
| 10,231,893 B2 | 3/2019 | Lei et al. |
| 10,235,606 B2 | 3/2019 | Miao et al. |
| 10,240,769 B1 | 3/2019 | Braganca et al. |
| 10,247,965 B2 | 4/2019 | Ton |
| 10,251,724 B2 | 4/2019 | McLachlin et al. |
| 10,261,324 B2 | 4/2019 | Chuang et al. |
| 10,262,424 B2 | 4/2019 | Ketcha et al. |
| 10,274,731 B2 | 4/2019 | Maimone |
| 10,278,777 B1 | 5/2019 | Lang |
| 10,292,768 B2 | 5/2019 | Lang |
| 10,296,805 B2 | 5/2019 | Yang et al. |
| 10,319,154 B1 | 6/2019 | Chakravarthula et al. |
| 10,326,975 B2 | 6/2019 | Casas |
| 10,332,267 B2 | 6/2019 | Rai et al. |
| 10,339,719 B2 | 7/2019 | Jagga et al. |
| 10,352,543 B1 | 7/2019 | Braganca et al. |
| 10,357,146 B2 | 7/2019 | Fiebel et al. |
| 10,357,574 B2 | 7/2019 | Hilderbrand et al. |
| 10,366,489 B2 | 7/2019 | Boettger et al. |
| 10,368,947 B2 | 8/2019 | Lang |
| 10,368,948 B2 | 8/2019 | Tripathi |
| 10,382,748 B2 | 8/2019 | Benishti et al. |
| 10,383,654 B2 | 8/2019 | Yilmaz et al. |
| 10,386,645 B2 | 8/2019 | Abou Shousha |
| 10,388,076 B2 | 8/2019 | Bar-Zeev et al. |
| 10,398,514 B2 | 9/2019 | Ryan et al. |
| 10,401,657 B2 | 9/2019 | Jiang et al. |
| 10,405,825 B2 | 9/2019 | Rai et al. |
| 10,405,927 B1 | 9/2019 | Lang |
| 10,413,752 B2 | 9/2019 | Berlinger et al. |
| 10,419,655 B2 | 9/2019 | Sivan |
| 10,420,626 B2 | 9/2019 | Tokuda et al. |
| 10,420,813 B2 | 9/2019 | Newell-Rogers et al. |
| 10,424,115 B2 | 9/2019 | Ellerbrock |
| D862,469 S | 10/2019 | Sadot et al. |
| 10,426,554 B2 | 10/2019 | Siewerdsen et al. |
| 10,429,675 B2 | 10/2019 | Greget |
| 10,431,008 B2 | 10/2019 | Djajadiningrat et al. |
| 10,433,814 B2 | 10/2019 | Razzaque et al. |
| 10,434,335 B2 | 10/2019 | Takahashi et al. |
| 10,441,236 B2 | 10/2019 | Bar-Tal et al. |
| 10,444,514 B2 | 10/2019 | Abou Shousha et al. |
| 10,447,947 B2 | 10/2019 | Liu |
| 10,448,003 B2 | 10/2019 | Grafenberg |
| 10,449,040 B2 | 10/2019 | Lashinski et al. |
| 10,453,187 B2 | 10/2019 | Peterson et al. |
| 10,463,434 B2 | 11/2019 | Siegler et al. |
| 10,465,892 B1 | 11/2019 | Feinbloom et al. |
| 10,466,487 B2 | 11/2019 | Blum et al. |
| 10,470,732 B2 | 11/2019 | Baumgart et al. |
| 10,473,314 B1 | 11/2019 | Braganca et al. |
| 10,485,989 B2 | 11/2019 | Jordan et al. |
| 10,488,663 B2 | 11/2019 | Choi |
| D869,772 S | 12/2019 | Gand |
| D870,977 S | 12/2019 | Berggren et al. |
| 10,492,755 B2 | 12/2019 | Lin et al. |
| 10,499,997 B2 | 12/2019 | Weinstein et al. |
| 10,502,363 B2 | 12/2019 | Edwards et al. |
| 10,504,231 B2 | 12/2019 | Fiala |
| 10,507,066 B2 | 12/2019 | Dimaio et al. |
| 10,511,822 B2 | 12/2019 | Casas |
| 10,517,544 B2 | 12/2019 | Taguchi et al. |
| 10,537,395 B2 | 1/2020 | Perez |
| 10,540,780 B1 | 1/2020 | Cousins et al. |
| 10,543,485 B2 | 1/2020 | Ismagilov et al. |
| 10,546,423 B2 | 1/2020 | Jones et al. |
| 10,548,557 B2 | 2/2020 | Lim et al. |
| 10,555,775 B2 | 2/2020 | Hoffman et al. |
| 10,568,535 B2 | 2/2020 | Roberts et al. |
| 10,571,696 B2 | 2/2020 | Urey et al. |
| 10,571,716 B2 | 2/2020 | Chapiro |
| 10,573,086 B2 | 2/2020 | Bar-Zeev et al. |
| 10,573,087 B2 | 2/2020 | Gallop et al. |
| 10,577,630 B2 | 3/2020 | Zhang et al. |
| 10,586,400 B2 | 3/2020 | Douglas |
| 10,591,737 B2 | 3/2020 | Yildiz et al. |
| 10,592,748 B1 | 3/2020 | Cousins et al. |
| 10,594,998 B1 | 3/2020 | Casas |
| 10,595,716 B2 | 3/2020 | Nazareth et al. |
| 10,601,950 B2 | 3/2020 | Devam et al. |
| 10,602,114 B2 | 3/2020 | Casas |
| 10,603,113 B2 | 3/2020 | Lang |
| 10,603,133 B2 | 3/2020 | Wang et al. |
| 10,606,085 B2 | 3/2020 | Toyama |
| 10,610,172 B2 | 4/2020 | Hummel et al. |
| 10,610,179 B2 | 4/2020 | Altmann |
| 10,613,352 B2 | 4/2020 | Knoll |
| 10,617,566 B2 | 4/2020 | Esmonde |
| 10,620,460 B2 | 4/2020 | Carabin |
| 10,621,738 B2 | 4/2020 | Miao et al. |
| 10,625,099 B2 | 4/2020 | Takahashi et al. |
| 10,626,473 B2 | 4/2020 | Mariani et al. |
| 10,631,905 B2 | 4/2020 | Asfora et al. |
| 10,631,907 B2 | 4/2020 | Zucker et al. |
| 10,634,331 B1 | 4/2020 | Feinbloom et al. |

(56) References Cited

U.S. PATENT DOCUMENTS

| | | |
|---|---|---|
| 10,634,921 B2 | 4/2020 | Blum et al. |
| 10,638,080 B2 | 4/2020 | Ovchinnikov et al. |
| 10,646,285 B2 | 5/2020 | Siemionow et al. |
| 10,650,513 B2 | 5/2020 | Penney et al. |
| 10,650,594 B2 | 5/2020 | Jones et al. |
| 10,652,525 B2 | 5/2020 | Woods |
| 10,653,495 B2 | 5/2020 | Gregerson et al. |
| 10,660,715 B2 | 5/2020 | Dozeman |
| 10,663,738 B2 | 5/2020 | Carlvik et al. |
| 10,665,033 B2 | 5/2020 | Bar-Zeev et al. |
| 10,670,937 B2 | 6/2020 | Alton et al. |
| 10,672,145 B2 | 6/2020 | Albiol et al. |
| 10,682,112 B2 | 6/2020 | Pizaine et al. |
| 10,682,767 B2 | 6/2020 | Grafenberg et al. |
| 10,687,901 B2 | 6/2020 | Thomas |
| 10,691,397 B1 | 6/2020 | Clements |
| 10,702,713 B2 | 7/2020 | Mori et al. |
| 10,706,540 B2 | 7/2020 | Merlet |
| 10,709,398 B2 | 7/2020 | Schweizer |
| 10,713,801 B2 | 7/2020 | Jordan et al. |
| 10,716,643 B2 | 7/2020 | Justin et al. |
| 10,722,733 B2 | 7/2020 | Takahashi |
| 10,725,535 B2 | 7/2020 | Yu |
| 10,731,832 B2 | 8/2020 | Koo |
| 10,732,721 B1 | 8/2020 | Clements |
| 10,742,949 B2 | 8/2020 | Casas |
| 10,743,939 B1 | 8/2020 | Lang |
| 10,743,943 B2 | 8/2020 | Razeto et al. |
| 10,747,315 B2 | 8/2020 | Tungare et al. |
| 10,748,319 B1 | 8/2020 | Tao et al. |
| 10,758,315 B2 | 9/2020 | Johnson et al. |
| 10,777,094 B1 | 9/2020 | Rao et al. |
| 10,777,315 B2 | 9/2020 | Zehavi et al. |
| 10,781,482 B2 | 9/2020 | Gubatayao et al. |
| 10,792,110 B2 | 10/2020 | Leung et al. |
| 10,799,145 B2 | 10/2020 | West et al. |
| 10,799,296 B2 | 10/2020 | Lang |
| 10,799,298 B2 | 10/2020 | Crawford et al. |
| 10,799,316 B2 | 10/2020 | Sela et al. |
| 10,810,799 B2 | 10/2020 | Tepper et al. |
| 10,818,019 B2 | 10/2020 | Piat et al. |
| 10,818,101 B2 | 10/2020 | Gallop et al. |
| 10,818,199 B2 | 10/2020 | Buras et al. |
| 10,825,563 B2 | 11/2020 | Gibby et al. |
| 10,827,164 B2 | 11/2020 | Perreault et al. |
| 10,831,943 B2 | 11/2020 | Santarone et al. |
| 10,835,296 B2 | 11/2020 | Elimelech et al. |
| 10,838,206 B2 | 11/2020 | Fortin-Deschnes et al. |
| 10,839,629 B2 | 11/2020 | Jones et al. |
| 10,839,956 B2 | 11/2020 | Beydoun et al. |
| 10,841,556 B2 | 11/2020 | Casas |
| 10,842,002 B2 | 11/2020 | Chang |
| 10,842,461 B2 | 11/2020 | Johnson et al. |
| 10,849,691 B2 | 12/2020 | Zucker et al. |
| 10,849,693 B2 | 12/2020 | Lang |
| 10,849,710 B2 | 12/2020 | Liu |
| 10,861,236 B2 | 12/2020 | Geri et al. |
| 10,865,220 B2 | 12/2020 | Ebetino et al. |
| 10,869,517 B1 | 12/2020 | Halpern |
| 10,869,727 B2 | 12/2020 | Yanof et al. |
| 10,872,472 B2 | 12/2020 | Watola et al. |
| 10,877,262 B1 | 12/2020 | Luxembourg |
| 10,877,296 B2 | 12/2020 | Lindsey et al. |
| 10,878,639 B2 | 12/2020 | Douglas et al. |
| 10,893,260 B2 | 1/2021 | Trail et al. |
| 10,895,742 B2 | 1/2021 | Schneider et al. |
| 10,895,743 B2 | 1/2021 | Dausmann |
| 10,895,906 B2 | 1/2021 | West et al. |
| 10,898,151 B2 | 1/2021 | Harding et al. |
| 10,908,420 B2 | 2/2021 | Lee et al. |
| 10,921,595 B2 | 2/2021 | Rakshit et al. |
| 10,921,613 B2 | 2/2021 | Gupta et al. |
| 10,928,321 B2 | 2/2021 | Rawle |
| 10,928,638 B2 | 2/2021 | Ninan et al. |
| 10,929,670 B1 | 2/2021 | Troy et al. |
| 10,935,815 B1 | 3/2021 | Castaeda |
| 10,935,816 B2 | 3/2021 | Ban et al. |
| 10,936,537 B2 | 3/2021 | Huston |
| 10,939,973 B2 | 3/2021 | Dimaio et al. |
| 10,939,977 B2 | 3/2021 | Messinger et al. |
| 10,941,933 B2 | 3/2021 | Ferguson |
| 10,946,108 B2 | 3/2021 | Zhang et al. |
| 10,950,338 B2 | 3/2021 | Douglas |
| 10,951,872 B2 | 3/2021 | Casas |
| 10,964,095 B1 | 3/2021 | Douglas |
| 10,964,124 B1 | 3/2021 | Douglas |
| 10,966,768 B2 | 4/2021 | Poulos |
| 10,969,587 B2 | 4/2021 | Mcdowall et al. |
| 10,993,754 B2 | 5/2021 | Kuntz et al. |
| 11,000,335 B2 | 5/2021 | Dorman |
| 11,002,994 B2 | 5/2021 | Jiang et al. |
| 11,006,093 B1 | 5/2021 | Hegyi |
| 11,013,550 B2 | 5/2021 | Rioux et al. |
| 11,013,560 B2 | 5/2021 | Lang |
| 11,013,562 B2 | 5/2021 | Marti et al. |
| 11,013,573 B2 | 5/2021 | Chang |
| 11,013,900 B2 | 5/2021 | Malek et al. |
| 11,016,302 B2 | 5/2021 | Freeman et al. |
| 11,019,988 B2 | 6/2021 | Fiebel et al. |
| 11,027,027 B2 | 6/2021 | Manning et al. |
| 11,029,147 B2 | 6/2021 | Abovitz et al. |
| 11,030,809 B2 | 6/2021 | Wang |
| 11,041,173 B2 | 6/2021 | Zhang et al. |
| 11,045,663 B2 | 6/2021 | Mori et al. |
| 11,049,293 B2 | 6/2021 | Chae et al. |
| 11,049,476 B2 | 6/2021 | Fuchs et al. |
| 11,050,990 B2 | 6/2021 | Casas |
| 11,057,505 B2 | 7/2021 | Dharmatilleke |
| 11,058,390 B1 | 7/2021 | Douglas |
| 11,061,257 B1 | 7/2021 | Hakim |
| 11,064,904 B2 | 7/2021 | Kay et al. |
| 11,065,062 B2 | 7/2021 | Frushour et al. |
| 11,067,387 B2 | 7/2021 | Marell et al. |
| 11,071,497 B2 | 7/2021 | Hallack et al. |
| 11,079,596 B2 | 8/2021 | Hua et al. |
| 11,087,039 B2 | 8/2021 | Duff et al. |
| 11,090,019 B2 | 8/2021 | Siemionow et al. |
| 11,097,129 B2 | 8/2021 | Sakata et al. |
| 11,099,376 B1 | 8/2021 | Steier et al. |
| 11,103,320 B2 | 8/2021 | Leboeuf et al. |
| D930,162 S | 9/2021 | Cremer et al. |
| 11,109,762 B1 | 9/2021 | Steier et al. |
| 11,112,611 B1 | 9/2021 | Kessler et al. |
| 11,122,164 B2 | 9/2021 | Gigante |
| 11,123,604 B2 | 9/2021 | Fung |
| 11,129,562 B2 | 9/2021 | Roberts et al. |
| 11,132,055 B2 | 9/2021 | Jones et al. |
| 11,135,015 B2 | 10/2021 | Crawford et al. |
| 11,135,016 B2 | 10/2021 | Frielinghaus et al. |
| 11,137,610 B1 | 10/2021 | Kessler et al. |
| 11,141,221 B2 | 10/2021 | Hobeika et al. |
| 11,153,549 B2 | 10/2021 | Casas |
| 11,153,555 B1 | 10/2021 | Healy et al. |
| 11,163,176 B2 | 11/2021 | Karafin et al. |
| 11,164,324 B2 | 11/2021 | Liu et al. |
| 11,166,006 B2 | 11/2021 | Hegyi |
| 11,169,380 B2 | 11/2021 | Manly et al. |
| 11,172,990 B2 | 11/2021 | Lang |
| 11,179,136 B2 | 11/2021 | Kohli et al. |
| 11,180,557 B2 | 11/2021 | Noelle |
| 11,181,747 B1 | 11/2021 | Kessler et al. |
| 11,185,891 B2 | 11/2021 | Cousins et al. |
| 11,187,907 B2 | 11/2021 | Osterman et al. |
| 11,202,682 B2 | 12/2021 | Staunton et al. |
| 11,207,150 B2 | 12/2021 | Healy et al. |
| 11,217,028 B2 | 1/2022 | Jones et al. |
| 11,224,483 B2 | 1/2022 | Steinberg et al. |
| 11,224,763 B2 | 1/2022 | Takahashi et al. |
| 11,227,417 B2 | 1/2022 | Berlinger et al. |
| 11,231,787 B2 | 1/2022 | Isaacs et al. |
| 11,243,404 B2 | 2/2022 | Mcdowall et al. |
| 11,244,508 B2 | 2/2022 | Kazanzides et al. |
| 11,253,216 B2 | 2/2022 | Crawford et al. |
| 11,253,323 B2 | 2/2022 | Hughes et al. |

(56) References Cited

U.S. PATENT DOCUMENTS

| | | |
|---|---|---|
| 11,257,190 B2 | 2/2022 | Mao et al. |
| 11,257,241 B2 | 2/2022 | Tao |
| 11,263,772 B2 | 3/2022 | Siemionow et al. |
| 11,269,401 B2 | 3/2022 | West et al. |
| 11,272,151 B2 | 3/2022 | Casas |
| 11,278,359 B2 | 3/2022 | Siemionow et al. |
| 11,278,413 B1 | 3/2022 | Lang |
| 11,280,480 B2 | 3/2022 | Wilt et al. |
| 11,284,846 B2 | 3/2022 | Graumann et al. |
| 11,291,521 B2 | 4/2022 | Im |
| 11,294,167 B2 | 4/2022 | Ishimoda |
| 11,297,285 B2 | 4/2022 | Pierce |
| 11,300,252 B2 | 4/2022 | Nguyen |
| 11,300,790 B2 | 4/2022 | Cheng et al. |
| 11,304,621 B2 | 4/2022 | Merschon et al. |
| 11,304,759 B2 | 4/2022 | Kovtun et al. |
| 11,307,402 B2 | 4/2022 | Steier et al. |
| 11,308,663 B2 | 4/2022 | Alhrishy et al. |
| 11,311,341 B2 | 4/2022 | Lang |
| 11,317,973 B2 | 5/2022 | Calloway et al. |
| 11,337,763 B2 | 5/2022 | Choi |
| 11,348,257 B2 | 5/2022 | Lang |
| 11,350,072 B1 | 5/2022 | Quiles Casas |
| 11,350,965 B2 | 6/2022 | Yilmaz et al. |
| 11,351,006 B2 | 6/2022 | Aferzon et al. |
| 11,354,813 B2 | 6/2022 | Piat et al. |
| 11,360,315 B2 | 6/2022 | Tu et al. |
| 11,373,342 B2 | 6/2022 | Stafford et al. |
| 11,382,699 B2 | 7/2022 | Wassall et al. |
| 11,382,700 B2 | 7/2022 | Calloway et al. |
| 11,382,712 B2 | 7/2022 | Elimelech et al. |
| 11,382,713 B2 | 7/2022 | Healy et al. |
| 11,389,252 B2 | 7/2022 | Gera et al. |
| 11,393,229 B2 | 7/2022 | Zhou et al. |
| 11,399,895 B2 | 8/2022 | Soper et al. |
| 11,402,524 B2 | 8/2022 | Song et al. |
| 11,406,338 B2 | 8/2022 | Tolkowsky |
| 11,412,202 B2 | 8/2022 | Hegyi |
| 11,423,554 B2 | 8/2022 | Borsdorf et al. |
| 11,430,203 B2 | 8/2022 | Navab et al. |
| 11,432,828 B1 | 9/2022 | Lang |
| 11,432,931 B2 | 9/2022 | Lang |
| 11,443,428 B2 | 9/2022 | Petersen et al. |
| 11,443,431 B2 | 9/2022 | Flossmann et al. |
| 11,452,568 B2 | 9/2022 | Lang |
| 11,452,570 B2 | 9/2022 | Tolkowsky |
| 11,460,915 B2 | 10/2022 | Frielinghaus et al. |
| 11,461,936 B2 | 10/2022 | Freeman et al. |
| 11,461,983 B2 | 10/2022 | Jones et al. |
| 11,464,580 B2 | 10/2022 | Kemp et al. |
| 11,464,581 B2 | 10/2022 | Calloway |
| 11,475,625 B1 | 10/2022 | Douglas |
| 11,478,214 B2 | 10/2022 | Siewerdsen et al. |
| 11,483,532 B2 | 10/2022 | Quiles Casas |
| 11,488,021 B2 | 11/2022 | Sun et al. |
| 11,490,986 B2 | 11/2022 | BEn-Yishai |
| 11,510,750 B2 | 11/2022 | Dulin et al. |
| 11,513,358 B2 | 11/2022 | Mcdowall et al. |
| 11,527,002 B2 | 12/2022 | Govari |
| 11,528,393 B2 | 12/2022 | Garofolo et al. |
| 11,544,031 B2 | 1/2023 | Harviainen |
| 11,573,420 B2 | 2/2023 | Sarma et al. |
| 11,589,927 B2 | 2/2023 | Oezbek et al. |
| 11,627,924 B2 | 4/2023 | Alexandroni et al. |
| 11,644,675 B2 | 5/2023 | Manly et al. |
| 11,648,016 B2 | 5/2023 | Hathaway et al. |
| 11,651,499 B2 | 5/2023 | Wang et al. |
| 11,657,518 B2 | 5/2023 | Ketcha et al. |
| 11,666,458 B2 | 6/2023 | Kim et al. |
| 11,669,984 B2 | 6/2023 | Siewerdsen et al. |
| 11,686,947 B2 | 6/2023 | Loyola et al. |
| 11,699,236 B2 | 7/2023 | Avital et al. |
| 11,712,582 B2 | 8/2023 | Miyazaki et al. |
| 11,715,210 B2 | 8/2023 | Haslam et al. |
| 11,719,941 B2 | 8/2023 | Russell |
| 11,730,389 B2 | 8/2023 | Farshad et al. |
| 11,733,516 B2 | 8/2023 | Edwin et al. |
| 11,734,901 B2 | 8/2023 | Jones et al. |
| 11,744,657 B2 | 9/2023 | Leboeuf et al. |
| 11,750,794 B2 | 9/2023 | Benishti et al. |
| 11,766,296 B2 | 9/2023 | Wolf et al. |
| 11,798,178 B2 | 10/2023 | Merlet |
| 11,801,097 B2 | 10/2023 | Crawford et al. |
| 11,801,115 B2 | 10/2023 | Elimelech et al. |
| 11,808,943 B2 | 11/2023 | Robaina et al. |
| 11,815,683 B2 | 11/2023 | Sears et al. |
| 11,826,111 B2 | 11/2023 | Mahfouz |
| 11,832,886 B2 | 12/2023 | Dorman |
| 11,838,493 B2 | 12/2023 | Healy et al. |
| 11,839,433 B2 | 12/2023 | Schaewe et al. |
| 11,839,501 B2 | 12/2023 | Takahashi et al. |
| 11,864,934 B2 | 1/2024 | Junio et al. |
| 11,885,752 B2 | 1/2024 | St-Aubin et al. |
| 11,892,647 B2 | 2/2024 | Hung et al. |
| 11,896,445 B2 | 2/2024 | Gera et al. |
| 11,900,620 B2 | 2/2024 | Lalys et al. |
| 11,914,155 B2 | 2/2024 | Zhu et al. |
| 11,918,310 B1 | 3/2024 | Roh et al. |
| 11,922,631 B2 | 3/2024 | Haslam et al. |
| 11,941,814 B2 | 3/2024 | Crawford et al. |
| 11,944,508 B1 | 4/2024 | Cowin et al. |
| 11,948,265 B2 | 4/2024 | Gibby et al. |
| 11,950,968 B2 | 4/2024 | Wiggermann |
| 11,957,420 B2 | 4/2024 | Lang |
| 11,961,193 B2 | 4/2024 | Pelzl et al. |
| 11,963,723 B2 | 4/2024 | Mlsmeier et al. |
| 11,972,582 B2 | 4/2024 | Yan et al. |
| 11,974,819 B2 | 5/2024 | Finley et al. |
| 11,974,887 B2 | 5/2024 | Elimelech et al. |
| 11,977,232 B2 | 5/2024 | Wu et al. |
| 11,980,429 B2 | 5/2024 | Wolf et al. |
| 11,980,506 B2 | 5/2024 | Wolf et al. |
| 11,980,507 B2 | 5/2024 | Elimelech et al. |
| 11,980,508 B2 | 5/2024 | Elimelech et al. |
| 11,983,824 B2 | 5/2024 | Avisar et al. |
| 12,002,171 B2 | 6/2024 | Jones et al. |
| 12,010,285 B2 | 6/2024 | Quiles Casas |
| 12,014,497 B2 | 6/2024 | Hong et al. |
| 12,019,314 B1 | 6/2024 | Steines et al. |
| 12,026,897 B2 | 7/2024 | Frantz et al. |
| 12,033,322 B2 | 7/2024 | Laaksonen et al. |
| 12,044,856 B2 | 7/2024 | Gera et al. |
| 12,044,858 B2 | 7/2024 | Gera et al. |
| 12,053,247 B1 | 8/2024 | Chiou |
| 12,056,830 B2 | 8/2024 | Cvetko et al. |
| 12,059,281 B2 | 8/2024 | Weingarten et al. |
| 12,063,338 B2 | 8/2024 | Quiles Casas |
| 12,063,345 B2 | 8/2024 | Benishti et al. |
| 12,069,233 B2 | 8/2024 | Benishti et al. |
| 12,076,158 B2 | 9/2024 | Geiger et al. |
| 12,076,196 B2 | 9/2024 | Elimelech et al. |
| 12,079,385 B2 | 9/2024 | Ben-Yishai et al. |
| 12,112,483 B2 | 10/2024 | Grady et al. |
| 12,114,933 B2 | 10/2024 | Seo et al. |
| 12,115,028 B2 | 10/2024 | Dulin et al. |
| 12,127,800 B2 | 10/2024 | Qian et al. |
| 12,133,772 B2 | 11/2024 | Calloway et al. |
| 12,136,176 B2 | 11/2024 | Spaas et al. |
| 12,142,365 B2 | 11/2024 | Kaethner et al. |
| 12,150,821 B2 | 11/2024 | Gera et al. |
| 12,178,666 B2 | 12/2024 | Wolf et al. |
| 12,186,028 B2 | 1/2025 | Gera et al. |
| 12,201,384 B2 | 1/2025 | Wolf et al. |
| 12,206,837 B2 | 1/2025 | Benishti et al. |
| 12,239,385 B2 | 3/2025 | Wolf et al. |
| 2002/0082498 A1 | 6/2002 | Wendt et al. |
| 2003/0059097 A1 | 3/2003 | Abovitz et al. |
| 2003/0117393 A1 | 6/2003 | Sauer et al. |
| 2003/0130576 A1 | 7/2003 | Seeley et al. |
| 2003/0156144 A1 | 8/2003 | Morita |
| 2003/0210812 A1 | 11/2003 | Khamene et al. |
| 2003/0225329 A1 | 12/2003 | Rossner et al. |
| 2004/0019263 A1 | 1/2004 | Jutras et al. |
| 2004/0030237 A1 | 2/2004 | Lee et al. |

(56) References Cited

U.S. PATENT DOCUMENTS

| | | |
|---|---|---|
| 2004/0138556 A1 | 7/2004 | Cosman |
| 2004/0152955 A1 | 8/2004 | McGinley et al. |
| 2004/0171930 A1 | 9/2004 | Grimm et al. |
| 2004/0238732 A1 | 12/2004 | State et al. |
| 2005/0017972 A1 | 1/2005 | Poole et al. |
| 2005/0024586 A1 | 2/2005 | Teiwes et al. |
| 2005/0119639 A1 | 6/2005 | McCombs et al. |
| 2005/0154296 A1 | 7/2005 | Lechner et al. |
| 2005/0203367 A1 | 9/2005 | Ahmed et al. |
| 2005/0203380 A1 | 9/2005 | Sauer et al. |
| 2005/0215879 A1 | 9/2005 | Chuanggui |
| 2005/0267358 A1 | 12/2005 | Tuma et al. |
| 2006/0072124 A1 | 4/2006 | Smetak et al. |
| 2006/0134198 A1 | 6/2006 | Tawa et al. |
| 2006/0147100 A1 | 7/2006 | Fitzpatrick |
| 2006/0176242 A1 | 8/2006 | Jaramaz et al. |
| 2006/0241760 A1 | 10/2006 | Randall et al. |
| 2007/0018975 A1 | 1/2007 | Chuanggui et al. |
| 2007/0058261 A1 | 3/2007 | Sugihara et al. |
| 2007/0100325 A1 | 5/2007 | Jutras et al. |
| 2007/0183041 A1 | 8/2007 | McCloy et al. |
| 2007/0233371 A1 | 10/2007 | Stoschek et al. |
| 2007/0273610 A1 | 11/2007 | Baillot |
| 2008/0002809 A1 | 1/2008 | Bodduluri |
| 2008/0007645 A1 | 1/2008 | McCutchen |
| 2008/0035266 A1 | 2/2008 | Danziger |
| 2008/0085033 A1 | 4/2008 | Haven et al. |
| 2008/0159612 A1 | 7/2008 | Fu et al. |
| 2008/0183065 A1 | 7/2008 | Goldbach |
| 2008/0221625 A1 | 9/2008 | Hufner et al. |
| 2008/0253527 A1 | 10/2008 | Boyden et al. |
| 2008/0262812 A1 | 10/2008 | Arata et al. |
| 2008/0287728 A1 | 11/2008 | Mostafavi et al. |
| 2009/0005961 A1 | 1/2009 | Grabowski et al. |
| 2009/0018437 A1 | 1/2009 | Cooke |
| 2009/0024127 A1 | 1/2009 | Lechner et al. |
| 2009/0036902 A1 | 2/2009 | Dimaio et al. |
| 2009/0062869 A1 | 3/2009 | Claverie et al. |
| 2009/0099445 A1 | 4/2009 | Burger |
| 2009/0123452 A1 | 5/2009 | Madison |
| 2009/0227847 A1 | 9/2009 | Tepper et al. |
| 2009/0285366 A1 | 11/2009 | Essenreiter et al. |
| 2009/0300540 A1 | 12/2009 | Russell |
| 2010/0076305 A1 | 3/2010 | Maier-Hein et al. |
| 2010/0094308 A1 | 4/2010 | Tatsumi et al. |
| 2010/0106010 A1 | 4/2010 | Rubner et al. |
| 2010/0114110 A1 | 5/2010 | Taft et al. |
| 2010/0138939 A1 | 6/2010 | Bentzon et al. |
| 2010/0149073 A1 | 6/2010 | Chaum et al. |
| 2010/0172567 A1 | 7/2010 | Prokoski |
| 2010/0210939 A1 | 8/2010 | Hartmann et al. |
| 2010/0266220 A1 | 10/2010 | Zagorchev et al. |
| 2010/0274124 A1 | 10/2010 | Jascob et al. |
| 2011/0004259 A1 | 1/2011 | Stallings et al. |
| 2011/0098553 A1 | 4/2011 | Robbins et al. |
| 2011/0105895 A1 | 5/2011 | Kornblau et al. |
| 2011/0125159 A1 | 5/2011 | Hanson et al. |
| 2011/0125160 A1 | 5/2011 | Bagga et al. |
| 2011/0216060 A1 | 9/2011 | Weising et al. |
| 2011/0245625 A1 | 10/2011 | Trovato et al. |
| 2011/0248064 A1 | 10/2011 | Marczyk |
| 2011/0254922 A1 | 10/2011 | Schaerer et al. |
| 2011/0306873 A1 | 12/2011 | Shenai et al. |
| 2012/0014608 A1 | 1/2012 | Watanabe |
| 2012/0068913 A1 | 3/2012 | Bar-Zeev et al. |
| 2012/0078236 A1 | 3/2012 | Schoepp |
| 2012/0109151 A1 | 5/2012 | Maier-Hein et al. |
| 2012/0143050 A1 | 6/2012 | Heigl |
| 2012/0155064 A1 | 6/2012 | Waters |
| 2012/0162452 A1 | 6/2012 | Liu |
| 2012/0182605 A1 | 7/2012 | Hall et al. |
| 2012/0201421 A1 | 8/2012 | Hartmann et al. |
| 2012/0216411 A1 | 8/2012 | Wevers et al. |
| 2012/0224260 A1 | 9/2012 | Healy et al. |
| 2012/0238609 A1 | 9/2012 | Srivastava et al. |
| 2012/0245645 A1 | 9/2012 | Hanson et al. |
| 2012/0289777 A1 | 11/2012 | Chopra et al. |
| 2012/0306850 A1 | 12/2012 | Balan et al. |
| 2012/0320100 A1 | 12/2012 | Machida et al. |
| 2013/0002928 A1 | 1/2013 | Imai |
| 2013/0009853 A1 | 1/2013 | Hesselink et al. |
| 2013/0038632 A1 | 2/2013 | Dillavou et al. |
| 2013/0050258 A1 | 2/2013 | Liu et al. |
| 2013/0050833 A1 | 2/2013 | Lewis et al. |
| 2013/0057581 A1 | 3/2013 | Meier |
| 2013/0079829 A1 | 3/2013 | Globerman et al. |
| 2013/0083009 A1 | 4/2013 | Geisner et al. |
| 2013/0106833 A1 | 5/2013 | Fun |
| 2013/0135734 A1 | 5/2013 | Shafer et al. |
| 2013/0135738 A1 | 5/2013 | Shafer et al. |
| 2013/0190602 A1 | 7/2013 | Liao et al. |
| 2013/0195338 A1 | 8/2013 | Xu et al. |
| 2013/0209953 A1 | 8/2013 | Arlinsky et al. |
| 2013/0212453 A1 | 8/2013 | Gudai et al. |
| 2013/0234914 A1 | 9/2013 | Fujimaki |
| 2013/0234935 A1 | 9/2013 | Griffith |
| 2013/0237811 A1 | 9/2013 | Mihailescu et al. |
| 2013/0245461 A1 | 9/2013 | Maier-Hein et al. |
| 2013/0249787 A1 | 9/2013 | Morimoto |
| 2013/0249945 A1 | 9/2013 | Kobayashi |
| 2013/0265623 A1 | 10/2013 | Sugiyama et al. |
| 2013/0267838 A1 | 10/2013 | Fronk et al. |
| 2013/0278631 A1 | 10/2013 | Border et al. |
| 2013/0278635 A1 | 10/2013 | Maggiore |
| 2013/0300637 A1 | 11/2013 | Smits et al. |
| 2013/0300760 A1 | 11/2013 | Sugano et al. |
| 2013/0342571 A1 | 12/2013 | Kinnebrew et al. |
| 2013/0345718 A1 | 12/2013 | Crawford et al. |
| 2014/0031668 A1 | 1/2014 | Mobasser et al. |
| 2014/0049629 A1 | 2/2014 | Siewerdsen et al. |
| 2014/0088402 A1 | 3/2014 | Xu |
| 2014/0088990 A1 | 3/2014 | Nawana et al. |
| 2014/0104505 A1 | 4/2014 | Koenig |
| 2014/0105912 A1 | 4/2014 | Noelle |
| 2014/0114173 A1 | 4/2014 | Bar-Tal et al. |
| 2014/0142426 A1 | 5/2014 | Razzaque et al. |
| 2014/0168261 A1 | 6/2014 | Margolis et al. |
| 2014/0176661 A1 | 6/2014 | Smurro et al. |
| 2014/0177023 A1 | 6/2014 | Gao et al. |
| 2014/0189508 A1 | 7/2014 | Granchi et al. |
| 2014/0198129 A1 | 7/2014 | Liu et al. |
| 2014/0218291 A1 | 8/2014 | Kirk |
| 2014/0240484 A1 | 8/2014 | Kodama et al. |
| 2014/0243614 A1 | 8/2014 | Rothberg et al. |
| 2014/0256429 A1 | 9/2014 | Kobayashi et al. |
| 2014/0266983 A1 | 9/2014 | Christensen |
| 2014/0268356 A1 | 9/2014 | Bolas et al. |
| 2014/0270505 A1 | 9/2014 | McCarthy |
| 2014/0275760 A1 | 9/2014 | Lee et al. |
| 2014/0285404 A1 | 9/2014 | Takano et al. |
| 2014/0285429 A1 | 9/2014 | Simmons |
| 2014/0288413 A1 | 9/2014 | Hwang et al. |
| 2014/0300632 A1 | 10/2014 | Laor |
| 2014/0300967 A1 | 10/2014 | Tilleman et al. |
| 2014/0301624 A1 | 10/2014 | Barckow et al. |
| 2014/0303491 A1 | 10/2014 | Shekhar et al. |
| 2014/0320399 A1 | 10/2014 | Kim et al. |
| 2014/0333899 A1 | 11/2014 | Smithwick |
| 2014/0336461 A1 | 11/2014 | Reiter et al. |
| 2014/0340286 A1 | 11/2014 | Machida et al. |
| 2014/0361956 A1 | 12/2014 | Mikhailov et al. |
| 2014/0371728 A1 | 12/2014 | Vaughn |
| 2015/0005772 A1 | 1/2015 | Anglin et al. |
| 2015/0018672 A1 | 1/2015 | Blumhofer et al. |
| 2015/0031985 A1 | 1/2015 | Reddy et al. |
| 2015/0043798 A1 | 2/2015 | Carrell et al. |
| 2015/0070347 A1 | 3/2015 | Hofmann et al. |
| 2015/0084990 A1 | 3/2015 | Laor |
| 2015/0148847 A1 | 5/2015 | Moskowitz et al. |
| 2015/0150641 A1 | 6/2015 | Daon et al. |
| 2015/0182293 A1 | 7/2015 | Yang et al. |
| 2015/0192776 A1 | 7/2015 | Lee et al. |
| 2015/0209119 A1 | 7/2015 | Theodore et al. |
| 2015/0230873 A1 | 8/2015 | Kubiak et al. |

(56) References Cited

U.S. PATENT DOCUMENTS

| | | |
|---|---|---|
| 2015/0230893 A1 | 8/2015 | Huwais |
| 2015/0261922 A1 | 9/2015 | Nawana et al. |
| 2015/0277123 A1 | 10/2015 | Chaum et al. |
| 2015/0282735 A1 | 10/2015 | Rossner |
| 2015/0287188 A1 | 10/2015 | Gazit et al. |
| 2015/0287236 A1 | 10/2015 | Winne et al. |
| 2015/0297314 A1 | 10/2015 | Fowler et al. |
| 2015/0305828 A1 | 10/2015 | Park et al. |
| 2015/0310668 A1 | 10/2015 | Ellerbrock |
| 2015/0338652 A1 | 11/2015 | Lim et al. |
| 2015/0338653 A1 | 11/2015 | Subramaniam et al. |
| 2015/0350517 A1 | 12/2015 | Duret et al. |
| 2015/0351863 A1 | 12/2015 | Plassky et al. |
| 2015/0363978 A1 | 12/2015 | Maimone et al. |
| 2015/0366620 A1 | 12/2015 | Cameron et al. |
| 2016/0015878 A1 | 1/2016 | Graham et al. |
| 2016/0022287 A1 | 1/2016 | Nehls |
| 2016/0030131 A1 | 2/2016 | Yang et al. |
| 2016/0054571 A1 | 2/2016 | Tazbaz et al. |
| 2016/0086380 A1 | 3/2016 | Vayser et al. |
| 2016/0103318 A1 | 4/2016 | Du et al. |
| 2016/0125603 A1 | 5/2016 | Tanji |
| 2016/0133051 A1 | 5/2016 | Aonuma et al. |
| 2016/0143699 A1 | 5/2016 | Tanji |
| 2016/0153004 A1 | 6/2016 | Zhang et al. |
| 2016/0163045 A1 | 6/2016 | Penney et al. |
| 2016/0175064 A1 | 6/2016 | Steinle et al. |
| 2016/0178910 A1 | 6/2016 | Giudicelli et al. |
| 2016/0191887 A1* | 6/2016 | Casas ................. G02B 27/0172 348/47 |
| 2016/0223822 A1 | 8/2016 | Harrison et al. |
| 2016/0228033 A1 | 8/2016 | Rossner |
| 2016/0246059 A1 | 8/2016 | Halpin et al. |
| 2016/0249989 A1 | 9/2016 | Devam et al. |
| 2016/0256223 A1 | 9/2016 | Haimerl et al. |
| 2016/0275684 A1 | 9/2016 | Elenbaas et al. |
| 2016/0297315 A1 | 10/2016 | Gonzalez et al. |
| 2016/0302870 A1 | 10/2016 | Wilkinson et al. |
| 2016/0324580 A1 | 11/2016 | Esterberg |
| 2016/0324583 A1 | 11/2016 | Kheradpir et al. |
| 2016/0339337 A1 | 11/2016 | Ellsworth et al. |
| 2017/0014119 A1 | 1/2017 | Capote et al. |
| 2017/0024634 A1 | 1/2017 | Miao et al. |
| 2017/0027650 A1 | 2/2017 | Merck et al. |
| 2017/0031163 A1 | 2/2017 | Gao et al. |
| 2017/0031179 A1 | 2/2017 | Guillot et al. |
| 2017/0045742 A1 | 2/2017 | Greenhalgh et al. |
| 2017/0065364 A1 | 3/2017 | Schuh et al. |
| 2017/0068119 A1 | 3/2017 | Antaki et al. |
| 2017/0076501 A1 | 3/2017 | Jagga et al. |
| 2017/0086941 A1 | 3/2017 | Marti et al. |
| 2017/0112586 A1 | 4/2017 | Dhupar |
| 2017/0148215 A1 | 5/2017 | Aksoy et al. |
| 2017/0164919 A1 | 6/2017 | Lavallee et al. |
| 2017/0164920 A1 | 6/2017 | Lavallee et al. |
| 2017/0172755 A1 | 6/2017 | Suh et al. |
| 2017/0178375 A1 | 6/2017 | Benishti et al. |
| 2017/0220224 A1 | 8/2017 | Kodali et al. |
| 2017/0239015 A1 | 8/2017 | Sela et al. |
| 2017/0245944 A1 | 8/2017 | Crawford et al. |
| 2017/0251900 A1 | 9/2017 | Hansen et al. |
| 2017/0252109 A1 | 9/2017 | Yang et al. |
| 2017/0258526 A1 | 9/2017 | Lang |
| 2017/0281283 A1 | 10/2017 | Siegler et al. |
| 2017/0312032 A1 | 11/2017 | Amanatullah et al. |
| 2017/0318235 A1 | 11/2017 | Schneider et al. |
| 2017/0322950 A1 | 11/2017 | Han et al. |
| 2017/0348055 A1 | 12/2017 | Salcedo et al. |
| 2017/0348061 A1 | 12/2017 | Joshi et al. |
| 2017/0366773 A1 | 12/2017 | Kiraly et al. |
| 2017/0367766 A1 | 12/2017 | Mahfouz |
| 2017/0367771 A1 | 12/2017 | Tako et al. |
| 2017/0372477 A1 | 12/2017 | Penney et al. |
| 2018/0003981 A1 | 1/2018 | Urey |
| 2018/0018791 A1 | 1/2018 | Guoyi |
| 2018/0021597 A1 | 1/2018 | Berlinger et al. |
| 2018/0028266 A1 | 2/2018 | Barnes et al. |
| 2018/0036884 A1 | 2/2018 | Chen et al. |
| 2018/0049622 A1 | 2/2018 | Ryan et al. |
| 2018/0055579 A1 | 3/2018 | Daon et al. |
| 2018/0071029 A1 | 3/2018 | Srimohanarajah et al. |
| 2018/0078316 A1 | 3/2018 | Schaewe et al. |
| 2018/0082480 A1 | 3/2018 | White et al. |
| 2018/0092667 A1 | 4/2018 | Heigl et al. |
| 2018/0092698 A1 | 4/2018 | Chopra et al. |
| 2018/0092699 A1 | 4/2018 | Finley |
| 2018/0116732 A1 | 5/2018 | Lin et al. |
| 2018/0116741 A1 | 5/2018 | Garcia et al. |
| 2018/0117150 A1 | 5/2018 | O'Dwyer et al. |
| 2018/0120106 A1 | 5/2018 | Sato |
| 2018/0133871 A1 | 5/2018 | Farmer |
| 2018/0143442 A1 | 5/2018 | Gupta |
| 2018/0153626 A1 | 6/2018 | Yang et al. |
| 2018/0182150 A1 | 6/2018 | Benishti et al. |
| 2018/0185100 A1 | 7/2018 | Weinstein et al. |
| 2018/0185113 A1 | 7/2018 | Gregerson et al. |
| 2018/0193097 A1 | 7/2018 | McLachlin et al. |
| 2018/0200002 A1 | 7/2018 | Kostrzewski et al. |
| 2018/0247128 A1 | 8/2018 | Alvi et al. |
| 2018/0262743 A1 | 9/2018 | Casas |
| 2018/0303558 A1 | 10/2018 | Thomas |
| 2018/0311011 A1 | 11/2018 | Van et al. |
| 2018/0317803 A1 | 11/2018 | Ben-Yishai et al. |
| 2018/0318035 A1 | 11/2018 | McLachlin et al. |
| 2018/0368898 A1 | 12/2018 | Divincenzo et al. |
| 2019/0000372 A1 | 1/2019 | Gullotti et al. |
| 2019/0000564 A1 | 1/2019 | Navab et al. |
| 2019/0015163 A1 | 1/2019 | Abhari et al. |
| 2019/0018235 A1 | 1/2019 | Ouderkirk et al. |
| 2019/0038362 A1 | 2/2019 | Nash et al. |
| 2019/0038365 A1 | 2/2019 | Soper et al. |
| 2019/0043238 A1 | 2/2019 | Benishti et al. |
| 2019/0043392 A1 | 2/2019 | Abele |
| 2019/0046272 A1 | 2/2019 | Zoabi et al. |
| 2019/0046276 A1 | 2/2019 | Inglese et al. |
| 2019/0053851 A1 | 2/2019 | Siemionow et al. |
| 2019/0069971 A1 | 3/2019 | Tripathi et al. |
| 2019/0080515 A1 | 3/2019 | Geri et al. |
| 2019/0105116 A1 | 4/2019 | Johnson et al. |
| 2019/0130792 A1 | 5/2019 | Rios et al. |
| 2019/0142519 A1 | 5/2019 | Siemionow et al. |
| 2019/0144443 A1 | 5/2019 | Jackson et al. |
| 2019/0175228 A1 | 6/2019 | Elimelech et al. |
| 2019/0192226 A1 | 6/2019 | Lang |
| 2019/0192230 A1 | 6/2019 | Siemionow et al. |
| 2019/0200894 A1 | 7/2019 | Jung et al. |
| 2019/0201106 A1 | 7/2019 | Siemionow et al. |
| 2019/0205606 A1 | 7/2019 | Zhou et al. |
| 2019/0216537 A1 | 7/2019 | Eltorai et al. |
| 2019/0251692 A1 | 8/2019 | Schmidt-Richberg et al. |
| 2019/0251694 A1 | 8/2019 | Han et al. |
| 2019/0254753 A1 | 8/2019 | Johnson et al. |
| 2019/0273916 A1 | 9/2019 | Benishti et al. |
| 2019/0310481 A1 | 10/2019 | Blum et al. |
| 2019/0324365 A1 | 10/2019 | De et al. |
| 2019/0333480 A1 | 10/2019 | Lang |
| 2019/0369660 A1 | 12/2019 | Wen et al. |
| 2019/0369717 A1 | 12/2019 | Frielinghaus et al. |
| 2019/0378276 A1 | 12/2019 | Flossmann et al. |
| 2019/0387351 A1 | 12/2019 | Lyren et al. |
| 2020/0015895 A1 | 1/2020 | Frielinghaus et al. |
| 2020/0019364 A1 | 1/2020 | Pond |
| 2020/0020249 A1 | 1/2020 | Jarc et al. |
| 2020/0038112 A1 | 2/2020 | Amanatullah et al. |
| 2020/0043160 A1 | 2/2020 | Mizukura et al. |
| 2020/0059640 A1 | 2/2020 | Browd et al. |
| 2020/0078100 A1 | 3/2020 | Weinstein et al. |
| 2020/0085511 A1 | 3/2020 | Oezbek et al. |
| 2020/0088997 A1 | 3/2020 | Lee et al. |
| 2020/0100847 A1 | 4/2020 | Siegler et al. |
| 2020/0117025 A1 | 4/2020 | Sauer |
| 2020/0129058 A1 | 4/2020 | Li et al. |
| 2020/0129136 A1 | 4/2020 | Harding et al. |
| 2020/0129262 A1 | 4/2020 | Verard et al. |

(56) References Cited

U.S. PATENT DOCUMENTS

| | | |
|---|---|---|
| 2020/0129264 A1 | 4/2020 | Oativia et al. |
| 2020/0133029 A1 | 4/2020 | Yonezawa |
| 2020/0138518 A1 | 5/2020 | Lang |
| 2020/0138618 A1 | 5/2020 | Roszkowiak et al. |
| 2020/0143594 A1 | 5/2020 | Lal et al. |
| 2020/0146546 A1 | 5/2020 | Chene et al. |
| 2020/0151507 A1 | 5/2020 | Siemionow et al. |
| 2020/0156259 A1 | 5/2020 | Ruiz et al. |
| 2020/0159313 A1 | 5/2020 | Gibby et al. |
| 2020/0163723 A1 | 5/2020 | Wolf et al. |
| 2020/0163739 A1 | 5/2020 | Messinger et al. |
| 2020/0178916 A1 | 6/2020 | Lalys et al. |
| 2020/0184638 A1 | 6/2020 | Meglan et al. |
| 2020/0186786 A1 | 6/2020 | Gibby et al. |
| 2020/0188028 A1 | 6/2020 | Feiner et al. |
| 2020/0188034 A1 | 6/2020 | Lequette et al. |
| 2020/0201082 A1 | 6/2020 | Carabin |
| 2020/0229877 A1 | 7/2020 | Siemionow et al. |
| 2020/0237256 A1 | 7/2020 | Farshad et al. |
| 2020/0237459 A1 | 7/2020 | Racheli et al. |
| 2020/0237880 A1 | 7/2020 | Kent et al. |
| 2020/0242280 A1 | 7/2020 | Pavloff et al. |
| 2020/0246074 A1 | 8/2020 | Lang |
| 2020/0246081 A1 | 8/2020 | Johnson et al. |
| 2020/0264451 A1 | 8/2020 | Blum et al. |
| 2020/0265273 A1 | 8/2020 | Wei et al. |
| 2020/0275988 A1 | 9/2020 | Johnson et al. |
| 2020/0281554 A1 | 9/2020 | Trini et al. |
| 2020/0286222 A1 | 9/2020 | Essenreiter et al. |
| 2020/0288075 A1 | 9/2020 | Bonin et al. |
| 2020/0294233 A1 | 9/2020 | Merlet |
| 2020/0297427 A1 | 9/2020 | Cameron et al. |
| 2020/0305980 A1 | 10/2020 | Lang |
| 2020/0315734 A1 | 10/2020 | El Amm |
| 2020/0321099 A1 | 10/2020 | Holladay et al. |
| 2020/0323460 A1 | 10/2020 | Busza et al. |
| 2020/0323609 A1 | 10/2020 | Johnson et al. |
| 2020/0327721 A1 | 10/2020 | Siemionow et al. |
| 2020/0330179 A1 | 10/2020 | Ton |
| 2020/0337780 A1 | 10/2020 | Winkler et al. |
| 2020/0341283 A1 | 10/2020 | McCracken et al. |
| 2020/0352655 A1 | 11/2020 | Freese |
| 2020/0355927 A1 | 11/2020 | Marcellin-Dibon et al. |
| 2020/0360091 A1 | 11/2020 | Murray et al. |
| 2020/0360105 A1 | 11/2020 | Frey et al. |
| 2020/0375666 A1 | 12/2020 | Murphy |
| 2020/0377493 A1 | 12/2020 | Heiser et al. |
| 2020/0377956 A1 | 12/2020 | Vogelstein et al. |
| 2020/0386982 A1 | 12/2020 | Luxembourg |
| 2020/0388075 A1 | 12/2020 | Kazanzides et al. |
| 2020/0389425 A1 | 12/2020 | Bhatia et al. |
| 2020/0390502 A1 | 12/2020 | Holthuizen et al. |
| 2020/0390503 A1 | 12/2020 | Casas et al. |
| 2020/0402647 A1 | 12/2020 | Domracheva et al. |
| 2020/0409306 A1 | 12/2020 | Gelman et al. |
| 2020/0410687 A1 | 12/2020 | Siemionow et al. |
| 2020/0413031 A1 | 12/2020 | Khani et al. |
| 2021/0004956 A1 | 1/2021 | Book et al. |
| 2021/0009339 A1 | 1/2021 | Morrison et al. |
| 2021/0015560 A1 | 1/2021 | Boddington et al. |
| 2021/0015583 A1 | 1/2021 | Avisar et al. |
| 2021/0022599 A1 | 1/2021 | Freeman et al. |
| 2021/0022808 A1 | 1/2021 | Lang |
| 2021/0022811 A1 | 1/2021 | Mahfouz |
| 2021/0022828 A1 | 1/2021 | Elimelech et al. |
| 2021/0029804 A1 | 1/2021 | Chang |
| 2021/0030374 A1 | 2/2021 | Takahashi et al. |
| 2021/0030511 A1 | 2/2021 | Wolf et al. |
| 2021/0038339 A1 | 2/2021 | Yu et al. |
| 2021/0049825 A1 | 2/2021 | Wheelwright et al. |
| 2021/0052348 A1 | 2/2021 | Stifter et al. |
| 2021/0056687 A1 | 2/2021 | Hibbard et al. |
| 2021/0065911 A1 | 3/2021 | Goel et al. |
| 2021/0077195 A1 | 3/2021 | Saeidi et al. |
| 2021/0077210 A1 | 3/2021 | Itkowitz et al. |
| 2021/0080751 A1 | 3/2021 | Lindsey et al. |
| 2021/0090344 A1 | 3/2021 | Geri et al. |
| 2021/0093391 A1 | 4/2021 | Poltaretskyi et al. |
| 2021/0093392 A1 | 4/2021 | Poltaretskyi et al. |
| 2021/0093400 A1 | 4/2021 | Quaid et al. |
| 2021/0093417 A1 | 4/2021 | Liu |
| 2021/0104055 A1 | 4/2021 | Ni et al. |
| 2021/0107923 A1 | 4/2021 | Jackson et al. |
| 2021/0109349 A1 | 4/2021 | Schneider et al. |
| 2021/0109373 A1 | 4/2021 | Loo et al. |
| 2021/0110517 A1 | 4/2021 | Flohr et al. |
| 2021/0113269 A1 | 4/2021 | Vilsmeier et al. |
| 2021/0113293 A9 | 4/2021 | Silva et al. |
| 2021/0121238 A1 | 4/2021 | Palushi et al. |
| 2021/0137634 A1 | 5/2021 | Lang |
| 2021/0141887 A1 | 5/2021 | Kim et al. |
| 2021/0150702 A1 | 5/2021 | Claessen et al. |
| 2021/0157544 A1 | 5/2021 | Denton |
| 2021/0160472 A1 | 5/2021 | Casas |
| 2021/0161614 A1 | 6/2021 | Elimelech et al. |
| 2021/0162287 A1 | 6/2021 | Xing et al. |
| 2021/0165207 A1 | 6/2021 | Peyman |
| 2021/0169504 A1 | 6/2021 | Brown |
| 2021/0169578 A1 | 6/2021 | Calloway et al. |
| 2021/0169581 A1 | 6/2021 | Calloway et al. |
| 2021/0169605 A1 | 6/2021 | Calloway et al. |
| 2021/0186647 A1 | 6/2021 | Elimelech et al. |
| 2021/0196404 A1 | 7/2021 | Wang |
| 2021/0211640 A1 | 7/2021 | Bristol et al. |
| 2021/0223577 A1 | 7/2021 | Zhang et al. |
| 2021/0225006 A1 | 7/2021 | Grady et al. |
| 2021/0227791 A1 | 7/2021 | De et al. |
| 2021/0231301 A1 | 7/2021 | Hikmet et al. |
| 2021/0235061 A1 | 7/2021 | Hegyi |
| 2021/0248822 A1 | 8/2021 | Choi et al. |
| 2021/0274281 A1 | 9/2021 | Zhang et al. |
| 2021/0278675 A1 | 9/2021 | Klug et al. |
| 2021/0282887 A1 | 9/2021 | Wiggermann |
| 2021/0290046 A1 | 9/2021 | Nazareth et al. |
| 2021/0290336 A1 | 9/2021 | Wang |
| 2021/0290394 A1 | 9/2021 | Mahfouz |
| 2021/0295108 A1 | 9/2021 | Bar |
| 2021/0295512 A1 | 9/2021 | Knoplioch et al. |
| 2021/0298795 A1 | 9/2021 | Bowling et al. |
| 2021/0298835 A1 | 9/2021 | Wang |
| 2021/0306599 A1 | 9/2021 | Pierce |
| 2021/0311322 A1 | 10/2021 | Belanger et al. |
| 2021/0314502 A1 | 10/2021 | Liu |
| 2021/0315636 A1 | 10/2021 | Akbarian et al. |
| 2021/0315662 A1 | 10/2021 | Freeman et al. |
| 2021/0325684 A1 | 10/2021 | Ninan et al. |
| 2021/0332447 A1 | 10/2021 | Lubelski et al. |
| 2021/0333561 A1 | 10/2021 | Oh et al. |
| 2021/0341739 A1 | 11/2021 | Cakmakci et al. |
| 2021/0341740 A1 | 11/2021 | Cakmakci et al. |
| 2021/0346115 A1 | 11/2021 | Dulin et al. |
| 2021/0349677 A1 | 11/2021 | Baldev et al. |
| 2021/0364802 A1 | 11/2021 | Uchiyama et al. |
| 2021/0369226 A1 | 12/2021 | Siemionow et al. |
| 2021/0371413 A1 | 12/2021 | Thurston et al. |
| 2021/0373333 A1 | 12/2021 | Moon |
| 2021/0373344 A1 | 12/2021 | Loyola et al. |
| 2021/0378757 A1 | 12/2021 | Bay et al. |
| 2021/0382310 A1 | 12/2021 | Freeman et al. |
| 2021/0386482 A1 | 12/2021 | Gera et al. |
| 2021/0389590 A1 | 12/2021 | Freeman et al. |
| 2021/0400247 A1 | 12/2021 | Casas |
| 2021/0401533 A1 | 12/2021 | Im |
| 2021/0402255 A1 | 12/2021 | Fung |
| 2021/0405369 A1 | 12/2021 | King |
| 2022/0003992 A1 | 1/2022 | Ahn |
| 2022/0007006 A1 | 1/2022 | Healy et al. |
| 2022/0008135 A1 | 1/2022 | Frielinghaus et al. |
| 2022/0038675 A1 | 2/2022 | Hegyi |
| 2022/0039873 A1 | 2/2022 | Harris |
| 2022/0051484 A1 | 2/2022 | Jones et al. |
| 2022/0054199 A1 | 2/2022 | Sivaprakasam et al. |
| 2022/0061921 A1 | 3/2022 | Crawford et al. |
| 2022/0071712 A1 | 3/2022 | Wolf et al. |

(56) References Cited

U.S. PATENT DOCUMENTS

| | | |
|---|---|---|
| 2022/0079675 A1 | 3/2022 | Lang |
| 2022/0087746 A1 | 3/2022 | Lang |
| 2022/0113810 A1 | 4/2022 | Isaacs et al. |
| 2022/0117669 A1 | 4/2022 | Nikou et al. |
| 2022/0121041 A1 | 4/2022 | Hakim |
| 2022/0125496 A1 | 4/2022 | Lpez et al. |
| 2022/0133484 A1 | 5/2022 | Lang |
| 2022/0142730 A1 | 5/2022 | Wolf et al. |
| 2022/0155861 A1 | 5/2022 | Myung et al. |
| 2022/0159227 A1 | 5/2022 | Quiles Casas |
| 2022/0179209 A1 | 6/2022 | Cherukuri |
| 2022/0192776 A1 | 6/2022 | Gibby et al. |
| 2022/0193453 A1 | 6/2022 | Miyazaki et al. |
| 2022/0201274 A1 | 6/2022 | Achilefu et al. |
| 2022/0245400 A1 | 8/2022 | Siemionow et al. |
| 2022/0245821 A1* | 8/2022 | Ouzounis ............... G06T 7/62 |
| 2022/0257206 A1 | 8/2022 | Hartley et al. |
| 2022/0269077 A1 | 8/2022 | Adema et al. |
| 2022/0270263 A1 | 8/2022 | Junio |
| 2022/0287676 A1 | 9/2022 | Steines et al. |
| 2022/0292786 A1 | 9/2022 | Pelzl et al. |
| 2022/0295033 A1 | 9/2022 | Quiles Casas |
| 2022/0296315 A1 | 9/2022 | Sokhanvar et al. |
| 2022/0304768 A1 | 9/2022 | Elimelech et al. |
| 2022/0351385 A1 | 11/2022 | Finley et al. |
| 2022/0353487 A1 | 11/2022 | Hegyi |
| 2022/0358759 A1 | 11/2022 | Cork et al. |
| 2022/0370152 A1 | 11/2022 | Lavallee et al. |
| 2022/0387130 A1 | 12/2022 | Spaas et al. |
| 2022/0392085 A1 | 12/2022 | Finley et al. |
| 2022/0397750 A1 | 12/2022 | Zhou et al. |
| 2022/0398752 A1 | 12/2022 | Yoon et al. |
| 2022/0398755 A1 | 12/2022 | Herrmann |
| 2022/0405935 A1 | 12/2022 | Flossmann et al. |
| 2023/0004013 A1 | 1/2023 | Mccracken et al. |
| 2023/0009793 A1 | 1/2023 | Gera et al. |
| 2023/0025480 A1 | 1/2023 | Kemp et al. |
| 2023/0027801 A1 | 1/2023 | Qian et al. |
| 2023/0032731 A1 | 2/2023 | Hrndler et al. |
| 2023/0034189 A1 | 2/2023 | Gera et al. |
| 2023/0050636 A1 | 2/2023 | Yanof et al. |
| 2023/0053120 A1 | 2/2023 | Jamali et al. |
| 2023/0073041 A1 | 3/2023 | Samadani et al. |
| 2023/0085387 A1 | 3/2023 | Jones et al. |
| 2023/0087783 A1 | 3/2023 | Dulin et al. |
| 2023/0100078 A1 | 3/2023 | Toporek et al. |
| 2023/0123621 A1 | 4/2023 | Joshi et al. |
| 2023/0126207 A1 | 4/2023 | Wang |
| 2023/0129056 A1 | 4/2023 | Hemingway et al. |
| 2023/0131515 A1 | 4/2023 | Oezbek et al. |
| 2023/0149083 A1 | 5/2023 | Lin et al. |
| 2023/0162493 A1 | 5/2023 | Worrell et al. |
| 2023/0165640 A1 | 6/2023 | Dulin et al. |
| 2023/0169659 A1 | 6/2023 | Chen et al. |
| 2023/0196582 A1 | 6/2023 | Grady et al. |
| 2023/0200917 A1 | 6/2023 | Calloway et al. |
| 2023/0236426 A1 | 7/2023 | Manly et al. |
| 2023/0236427 A1 | 7/2023 | Jiannyuh |
| 2023/0245784 A1 | 8/2023 | Crawford et al. |
| 2023/0260142 A1 | 8/2023 | Chatterjee et al. |
| 2023/0290037 A1 | 9/2023 | Tasse et al. |
| 2023/0295302 A1 | 9/2023 | Bhagavatheeswaran et al. |
| 2023/0306590 A1 | 9/2023 | Jazdzyk et al. |
| 2023/0316550 A1 | 10/2023 | Hiasa |
| 2023/0326011 A1 | 10/2023 | Cutforth et al. |
| 2023/0326027 A1 | 10/2023 | Wahrenberg |
| 2023/0329799 A1 | 10/2023 | Gera et al. |
| 2023/0329801 A1 | 10/2023 | Elimelech et al. |
| 2023/0334664 A1 | 10/2023 | Lu et al. |
| 2023/0335261 A1 | 10/2023 | Reicher et al. |
| 2023/0359043 A1 | 11/2023 | Russell |
| 2023/0363832 A1 | 11/2023 | Mosadegh et al. |
| 2023/0371984 A1 | 11/2023 | Leuthardt et al. |
| 2023/0372053 A1 | 11/2023 | Elimelech et al. |
| 2023/0372054 A1 | 11/2023 | Elimelech et al. |
| 2023/0377171 A1 | 11/2023 | Hasler et al. |
| 2023/0377175 A1 | 11/2023 | Seok |
| 2023/0379448 A1 | 11/2023 | Benishti et al. |
| 2023/0379449 A1 | 11/2023 | Benishti et al. |
| 2023/0386022 A1 | 11/2023 | Tan et al. |
| 2023/0386067 A1 | 11/2023 | De et al. |
| 2023/0389991 A1 | 12/2023 | Glaser et al. |
| 2023/0394791 A1 | 12/2023 | Wang et al. |
| 2023/0397349 A1 | 12/2023 | Capelli et al. |
| 2023/0397957 A1 | 12/2023 | Crawford et al. |
| 2023/0410445 A1 | 12/2023 | Elimelech et al. |
| 2023/0419496 A1 | 12/2023 | Wuelker et al. |
| 2023/0420114 A1 | 12/2023 | Scholler et al. |
| 2024/0008935 A1 | 1/2024 | Wolf et al. |
| 2024/0016549 A1 | 1/2024 | Johnson et al. |
| 2024/0016572 A1 | 1/2024 | Elimelech et al. |
| 2024/0020831 A1 | 1/2024 | Johnson et al. |
| 2024/0020840 A1 | 1/2024 | Johnson et al. |
| 2024/0020862 A1 | 1/2024 | Johnson et al. |
| 2024/0022704 A1 | 1/2024 | Benishti et al. |
| 2024/0023946 A1 | 1/2024 | Wolf et al. |
| 2024/0041530 A1 | 2/2024 | Lang |
| 2024/0041558 A1 | 2/2024 | Siewerdsen et al. |
| 2024/0045491 A1 | 2/2024 | Sourov |
| 2024/0058064 A1 | 2/2024 | Weiser et al. |
| 2024/0062387 A1 | 2/2024 | Frantz et al. |
| 2024/0103271 A1 | 3/2024 | Zare Seisan |
| 2024/0103282 A1 | 3/2024 | Law et al. |
| 2024/0111163 A1 | 4/2024 | Law et al. |
| 2024/0122560 A1 | 4/2024 | Junio et al. |
| 2024/0126087 A1 | 4/2024 | Gera et al. |
| 2024/0127578 A1 | 4/2024 | Hiasa |
| 2024/0129451 A1 | 4/2024 | Healy et al. |
| 2024/0130826 A1 | 4/2024 | Elimelech et al. |
| 2024/0134206 A1 | 4/2024 | Gera et al. |
| 2024/0144497 A1 | 5/2024 | Cvetko et al. |
| 2024/0156532 A1 | 5/2024 | Weiman et al. |
| 2024/0177445 A1 | 5/2024 | Galeotti et al. |
| 2024/0177458 A1 | 5/2024 | Zhang et al. |
| 2024/0180634 A1 | 6/2024 | Mikus |
| 2024/0184119 A1 | 6/2024 | Lee et al. |
| 2024/0185509 A1 | 6/2024 | Kovler et al. |
| 2024/0202926 A1 | 6/2024 | Crawford et al. |
| 2024/0202927 A1 | 6/2024 | Haslam et al. |
| 2024/0212111 A1 | 6/2024 | Genghi et al. |
| 2024/0233131 A1 | 7/2024 | Westerhoff et al. |
| 2024/0245463 A1 | 7/2024 | Mlsmeier et al. |
| 2024/0245474 A1 | 7/2024 | Weiman et al. |
| 2024/0248530 A1 | 7/2024 | Gibby et al. |
| 2024/0252252 A1 | 8/2024 | Lang |
| 2024/0261036 A1 | 8/2024 | Finley et al. |
| 2024/0261058 A1 | 8/2024 | Gera et al. |
| 2024/0265645 A1 | 8/2024 | Papar |
| 2024/0266033 A1 | 8/2024 | Freeman et al. |
| 2024/0268922 A1 | 8/2024 | Calloway et al. |
| 2024/0273740 A1 | 8/2024 | Gibby et al. |
| 2024/0281979 A1 | 8/2024 | Schrempf et al. |
| 2024/0296527 A1 | 9/2024 | Nett et al. |
| 2024/0303832 A1 | 9/2024 | Chen et al. |
| 2024/0307101 A1 | 9/2024 | Gera et al. |
| 2024/0312012 A1 | 9/2024 | Li et al. |
| 2024/0341853 A1 | 10/2024 | Gibby et al. |
| 2024/0341861 A1 | 10/2024 | Wolf et al. |
| 2024/0341910 A1 | 10/2024 | Wolf et al. |
| 2024/0341911 A1 | 10/2024 | Elimelech et al. |
| 2024/0355098 A1 | 10/2024 | Liu et al. |
| 2024/0374314 A1 | 11/2024 | Frey et al. |
| 2024/0377640 A1 | 11/2024 | Asaban et al. |
| 2024/0378708 A1 | 11/2024 | Kim et al. |
| 2024/0382283 A1 | 11/2024 | Kuhnert et al. |
| 2024/0386572 A1 | 11/2024 | Barasofsky et al. |
| 2024/0386682 A1 | 11/2024 | Cvetko et al. |
| 2024/0394883 A1 | 11/2024 | Liao et al. |
| 2024/0394985 A1 | 11/2024 | Hanlon et al. |
| 2024/0404065 A1 | 12/2024 | Gibbons et al. |
| 2024/0404106 A1 | 12/2024 | Wu et al. |
| 2024/0404180 A1 | 12/2024 | Kobayashi et al. |
| 2024/0420337 A1 | 12/2024 | Li et al. |
| 2024/0420592 A1 | 12/2024 | Stone et al. |

(56) References Cited

U.S. PATENT DOCUMENTS

| | | |
|---|---|---|
| 2024/0423724 A1 | 12/2024 | Wolf et al. |
| 2024/0423750 A1 | 12/2024 | Elimelech et al. |
| 2025/0020931 A1 | 1/2025 | Gera et al. |
| 2025/0049534 A1 | 2/2025 | Elimelech et al. |
| 2025/0090266 A1 | 3/2025 | Gera et al. |
| 2025/0114151 A1 | 4/2025 | Gera et al. |
| 2025/0114164 A1 | 4/2025 | Gera et al. |
| 2025/0114165 A1 | 4/2025 | Wolf et al. |

FOREIGN PATENT DOCUMENTS

| | | |
|---|---|---|
| CN | 101379412 A | 3/2009 |
| CN | 102740784 A | 10/2012 |
| CN | 102740789 A | 10/2012 |
| CN | 103106348 A | 5/2013 |
| CN | 103945780 A | 7/2014 |
| CN | 105310756 A | 2/2016 |
| CN | 109199563 A | 1/2019 |
| CN | 111915696 A | 11/2020 |
| CN | 112489047 A | 3/2021 |
| DE | 202004011567 U1 | 11/2004 |
| DE | 102004011567 A1 | 9/2005 |
| DE | 102014008153 A1 | 10/2014 |
| DE | 202022103168 U1 | 6/2022 |
| EP | 0933096 A2 | 8/1999 |
| EP | 1640750 A1 | 3/2006 |
| EP | 1757974 A1 | 2/2007 |
| EP | 2119397 A1 | 11/2009 |
| EP | 2134847 A2 | 12/2009 |
| EP | 2557998 A1 | 2/2013 |
| EP | 2823463 A1 | 1/2015 |
| EP | 2868277 A1 | 5/2015 |
| EP | 2891966 A1 | 7/2015 |
| EP | 2963616 A2 | 1/2016 |
| EP | 3028258 A1 | 6/2016 |
| EP | 3034607 A1 | 6/2016 |
| EP | 3037038 A1 | 6/2016 |
| EP | 3069318 A1 | 9/2016 |
| EP | 3076660 A1 | 10/2016 |
| EP | 3121789 A1 | 1/2017 |
| EP | 3123970 A1 | 2/2017 |
| EP | 2654749 B1 | 5/2017 |
| EP | 3175815 A1 | 6/2017 |
| EP | 3216416 A1 | 9/2017 |
| EP | 2032039 B1 | 10/2017 |
| EP | 3224376 A1 | 10/2017 |
| EP | 3247297 A1 | 11/2017 |
| EP | 3256213 A1 | 12/2017 |
| EP | 3306567 A1 | 4/2018 |
| EP | 3320874 A1 | 5/2018 |
| EP | 2030193 B1 | 7/2018 |
| EP | 2225723 B1 | 2/2019 |
| EP | 2619622 B1 | 2/2019 |
| EP | 2892558 B1 | 4/2019 |
| EP | 3494903 A1 | 6/2019 |
| EP | 2635299 B1 | 7/2019 |
| EP | 3505050 A1 | 7/2019 |
| EP | 2875149 B1 | 12/2019 |
| EP | 3593227 A1 | 1/2020 |
| EP | 3634294 A1 | 4/2020 |
| EP | 3206583 B1 | 9/2020 |
| EP | 3711700 A1 | 9/2020 |
| EP | 2625845 B1 | 3/2021 |
| EP | 3789965 A1 | 3/2021 |
| EP | 3858280 A1 | 8/2021 |
| EP | 3913423 A1 | 11/2021 |
| EP | 3952331 A1 | 2/2022 |
| EP | 3960235 A1 | 3/2022 |
| EP | 3635683 B1 | 7/2022 |
| EP | 3602492 B1 | 11/2022 |
| EP | 4173590 A1 | 5/2023 |
| EP | 3533031 B1 | 8/2023 |
| EP | 4252695 A1 | 10/2023 |
| EP | 3195257 B1 | 11/2023 |
| EP | 3405909 B1 | 11/2023 |
| EP | 4270313 A1 | 11/2023 |
| EP | 4287120 A1 | 12/2023 |
| EP | 3488381 B1 | 2/2024 |
| EP | 3834768 B1 | 2/2024 |
| EP | 3903714 B1 | 2/2024 |
| EP | 4336450 A1 | 3/2024 |
| EP | 3814984 B1 | 4/2024 |
| EP | 4115389 B1 | 4/2024 |
| EP | 3752981 B1 | 5/2024 |
| EP | 4375948 A1 | 5/2024 |
| EP | 4383203 A1 | 6/2024 |
| EP | 4459543 A1 | 11/2024 |
| EP | 4292045 B1 | 12/2024 |
| EP | 4298604 B1 | 12/2024 |
| GB | 2507314 A | 4/2014 |
| IL | 262864 A | 3/2019 |
| JP | 2004-237092 A | 8/2004 |
| JP | 2005-246059 A | 9/2005 |
| JP | 2008-507361 A | 3/2008 |
| JP | 2009-514571 A | 4/2009 |
| JP | 2021-525186 A | 9/2021 |
| KR | 10-2014-0120155 A | 10/2014 |
| WO | 03/34705 A2 | 4/2003 |
| WO | 2006/002559 A1 | 1/2006 |
| WO | 2007/051304 A1 | 5/2007 |
| WO | 2007/115826 A2 | 10/2007 |
| WO | 2008/103383 A1 | 8/2008 |
| WO | 2010/067267 A1 | 6/2010 |
| WO | 2010/074747 A1 | 7/2010 |
| WO | 2012/061537 A2 | 5/2012 |
| WO | 2012/101286 A1 | 8/2012 |
| WO | 2013/112554 A1 | 8/2013 |
| WO | 2014/014498 A1 | 1/2014 |
| WO | 2014/024188 A1 | 2/2014 |
| WO | 2014/037953 A2 | 3/2014 |
| WO | 2014/113455 A1 | 7/2014 |
| WO | 2014/125789 A1 | 8/2014 |
| WO | 2014/167563 A1 | 10/2014 |
| WO | 2014/174067 A1 | 10/2014 |
| WO | 2015/058816 A1 | 4/2015 |
| WO | 2015/061752 A1 | 4/2015 |
| WO | 2015/109145 A1 | 7/2015 |
| WO | 2016/151506 A1 | 9/2016 |
| WO | 2017/042171 A1 | 3/2017 |
| WO | 2018/052966 A1 | 3/2018 |
| WO | 2018/073452 A1 | 4/2018 |
| WO | 2018/200767 A1 | 11/2018 |
| WO | 2018/206086 A1 | 11/2018 |
| WO | 2019/083431 A1 | 5/2019 |
| WO | 2019/135209 A1 | 7/2019 |
| WO | 2019/135210 A1 | 7/2019 |
| WO | 2019/161477 A1 | 8/2019 |
| WO | 2019/195926 A1 | 10/2019 |
| WO | 2019/210353 A1 | 11/2019 |
| WO | 2019/211741 A1 | 11/2019 |
| WO | 2020/109903 A1 | 6/2020 |
| WO | 2020/109904 A1 | 6/2020 |
| WO | 2021/017019 A1 | 2/2021 |
| WO | 2021/019369 A1 | 2/2021 |
| WO | 2021/021979 A2 | 2/2021 |
| WO | 2021/023574 A1 | 2/2021 |
| WO | 2021/046455 A1 | 3/2021 |
| WO | 2021/048158 A1 | 3/2021 |
| WO | 2021/061459 A1 | 4/2021 |
| WO | 2021/062375 A1 | 4/2021 |
| WO | 2021/073743 A1 | 4/2021 |
| WO | 2021/087439 A1 | 5/2021 |
| WO | 2021/091980 A1 | 5/2021 |
| WO | 2021/112918 A1 | 6/2021 |
| WO | 2021/130564 A1 | 7/2021 |
| WO | 2021/137752 A1 | 7/2021 |
| WO | 2021/141887 A1 | 7/2021 |
| WO | 2021/145584 A1 | 7/2021 |
| WO | 2021/154076 A1 | 8/2021 |
| WO | 2021/183318 A2 | 9/2021 |
| WO | 2021/188757 A1 | 9/2021 |
| WO | 2021/255627 A1 | 12/2021 |
| WO | 2021/257897 A1 | 12/2021 |
| WO | 2021/258078 A1 | 12/2021 |

(56) References Cited

FOREIGN PATENT DOCUMENTS

| | | | |
|---|---|---|---|
| WO | 2022/009233 | A1 | 1/2022 |
| WO | 2022/053923 | A1 | 3/2022 |
| WO | 2022/056010 | A1 | 3/2022 |
| WO | 2022/079565 | A1 | 4/2022 |
| WO | 2022/180624 | A1 | 9/2022 |
| WO | 2023/003952 | A1 | 1/2023 |
| WO | 2023/281395 | A1 | 1/2023 |
| WO | 2023/007418 | A1 | 2/2023 |
| WO | 2023/011924 | A1 | 2/2023 |
| WO | 2023/021448 | A1 | 2/2023 |
| WO | 2023/021450 | A1 | 2/2023 |
| WO | 2023/021451 | A1 | 2/2023 |
| WO | 2023/026229 | A1 | 3/2023 |
| WO | 2023/047355 | A1 | 3/2023 |
| WO | 2023/072887 | A1 | 5/2023 |
| WO | 2023/088986 | A1 | 5/2023 |
| WO | 2023/158878 | A1 | 8/2023 |
| WO | 2023/159104 | A2 | 8/2023 |
| WO | 2023/161848 | A1 | 8/2023 |
| WO | 2023/163933 | A1 | 8/2023 |
| WO | 2023/175244 | A1 | 9/2023 |
| WO | 2023/186996 | A1 | 10/2023 |
| WO | 2023/202909 | A1 | 10/2023 |
| WO | 2023/205212 | A1 | 10/2023 |
| WO | 2023/205896 | A1 | 11/2023 |
| WO | 2023/209014 | A1 | 11/2023 |
| WO | 2023/229415 | A1 | 11/2023 |
| WO | 2023/232492 | A1 | 12/2023 |
| WO | 2023/240912 | A1 | 12/2023 |
| WO | 2024/001140 | A1 | 1/2024 |
| WO | 2024/002620 | A1 | 1/2024 |
| WO | 2024/013642 | A2 | 1/2024 |
| WO | 2024/018368 | A2 | 1/2024 |
| WO | 2024/046760 | A1 | 3/2024 |
| WO | 2024/052136 | A1 | 3/2024 |
| WO | 2024/077077 | A1 | 4/2024 |
| WO | 2024/121060 | A1 | 6/2024 |
| WO | 2024/132609 | A1 | 6/2024 |
| WO | 2024/145341 | A1 | 7/2024 |
| WO | 2024/160896 | A1 | 8/2024 |
| WO | 2024/165508 | A1 | 8/2024 |
| WO | 2024/173251 | A1 | 8/2024 |
| WO | 2024/186811 | A1 | 9/2024 |
| WO | 2024/226797 | A1 | 10/2024 |
| WO | 2024/251344 | A1 | 12/2024 |

OTHER PUBLICATIONS

U.S. Appl. No. 16/159,740 (U.S. Pat. No. 10,382,748), filed Oct. 15, 2018 (Aug. 13, 2019), Combining Video-Based and Optic-Based Augmented Reality in a Near Eye Display.
U.S. Appl. No. 16/419,023 (U.S. Pat. No. 11,750,794), filed May 22, 2019 (Sep. 5, 2023), Combining Video-Based and Optic-Based Augmented Reality in a Near Eye Display.
U.S. Appl. No. 18/352,158, filed Jul. 13, 2023, Combining Video-Based and Optic-Based Augmented Reality in a Near Eye Display.
U.S. Appl. No. 18/365,643, filed Aug. 4, 2023, Head-Mounted Augmented Reality Near Eye Display Device.
U.S. Appl. No. 18/365,650, filed Aug. 4, 2023, Systems for Facilitating Augmented Reality-Assisted Medical Procedures.
U.S. Appl. No. 15/127,423 (U.S. Pat. No. 9,928,629), filed Sep. 20, 2016 (Mar. 27, 2018), Combining Video-Based and Optic-Based Augmented Reality in a Near Eye Display.
U.S. Appl. No. 16/120,480 (U.S. Pat. No. 10,835,296), filed Sep. 4, 2018 (Nov. 17, 2020), Spinous Process Clamp.
U.S. Appl. No. 17/067,831, filed Oct. 12, 2020, Spinous Process Clamp.
U.S. Appl. No. 18/030,072, filed Apr. 4, 2023, Spinous Process Clamp.
U.S. Appl. No. 18/365,590 (U.S. Pat. No. 11,980,508), filed Aug. 4, 2023 (May 14, 2024), Registration of a Fiducial Marker for an Augmented Reality System.
U.S. Appl. No. 18/365,571 (U.S. Pat. No. 11,974,887), filed Aug. 4, 2023 (May 7, 2024), Registration Marker for an Augmented Reality System.
U.S. Appl. No. 18/632,588, filed Apr. 11, 2024, Registration of a Fiducial Marker for an Augmented Reality System.
U.S. Appl. No. 17/045,766 (U.S. Pat. No. 11,980,507), filed Oct. 7, 2020 (May 14, 2024), Registration of a Fiducial Marker for an Augmented Reality System.
U.S. Appl. No. 16/199,281 (U.S. Pat. No. 10,939,977), filed Nov. 26, 2018 (Mar. 9, 2021), Positioning Marker.
U.S. Appl. No. 16/524,258 (U.S. Pat. No. 11,980,506), filed Jul. 29, 2019 (May 14, 2024), Fiducial Marker.
U.S. Appl. No. 18/631,804, filed Apr. 10, 2024, Fiducial Marker.
U.S. Appl. No. 17/585,629, filed Jan. 27, 2022, Fiducial Marker.
U.S. Appl. No. 16/724,297 (U.S. Pat. No. 11,382,712), filed Dec. 22, 2019 (Jul. 12, 2022), Mirroring in Image Guided Surgery.
U.S. Appl. No. 17/827,710 (U.S. Pat. No. 11,801,115), filed May 29, 2022 (Oct. 31, 2023), Mirroring in Image Guided Surgery.
U.S. Appl. No. 18/352,181, filed Jul. 13, 2023, Mirroring in Image Guided Surgery.
U.S. Appl. No. 18/400,739, filed Dec. 29, 2023, Mirroring in Image Guided Surgery.
U.S. Appl. No. 16/200,144 (U.S. Pat. No. 11,766,296), filed Nov. 26, 2018 (Sep. 26, 2023), Tracking System for Image-Guided Surgery.
U.S. Appl. No. 18/470,809 (U.S. Pat. No. 11,980,429), filed Sep. 20, 2023 (May 14, 2024), Tracking Methods for Image-Guided Surgery.
U.S. Appl. No. 18/631,877, filed Apr. 10, 2024, Tracking Systems and Methods for Image-Guided Surgery.
U.S. Appl. No. 17/015,199, filed Sep. 9, 2020, Universal Tool Adapter.
U.S. Appl. No. 18/598,965, filed Mar. 7, 2024, Universal Tool Adapter for Image Guided Surgery.
U.S. Appl. No. 18/044,380, filed Mar. 8, 2023, Universal Tool Adapter for Image-Guided Surgery.
U.S. Appl. No. 16/901,026 (U.S. Pat. No. 11,389,252), filed Jun. 15, 2020 (Jul. 19, 2022), Rotating Marker for Image Guided Surgery.
U.S. Appl. No. 18/008,980, filed Dec. 8, 2022, Rotating Marker.
U.S. Appl. No. 17/368,859 (U.S. Pat. No. 11,896,445), Jul. 7, 2021 (Feb. 13, 2024), Iliac Pin and Adapter.
U.S. Appl. No. 18/437,898, filed Feb. 9, 2024, Iliac Pin and Adapter.
U.S. Appl. No. 18/576,516, filed Jan. 4, 2024, Iliac Pin and Adapter.
U.S. Appl. No. 17/388,064, filed Jul. 29, 2021, Rotating Marker and Adapter for Image-Guided Surgery.
U.S. Appl. No. 18/291,731, filed Jan. 24, 2024, Rotating Marker and Adapter for Image-Guided Surgery.
U.S. Appl. No. 18/365,844, filed Aug. 4, 2023, Augmented-Reality Surgical System Using Depth Sensing.
U.S. Appl. No. 18/683,676, filed Feb. 14, 2024, Stereoscopic Display and Digital Loupe for Augmented-Reality Near-Eye Display.
U.S. Appl. No. 18/683,680, filed Feb. 14, 2024, Augmented Reality Assistance for Osteotomy and Discectomy.
U.S. Appl. No. 18/684,756, filed Feb. 19, 2024, Registration and Registration Validation in Image-Guided Surgery.
U.S. Appl. No. 18/693,338, filed Mar. 19, 2024, Surgical Planning and Display.
U.S. Appl. No. 18/365,566, filed Aug. 4, 2023, Systems for Medical Image Visualization.
U.S. Appl. No. 18/398,837, filed Dec. 28, 2023, Adjustable Augmented Reality Eyewear for Image-Guided Medical Intervention.
U.S. Appl. No. 18/399,433, filed Dec. 28, 2023, Configurable Augmented Reality Eyewear for Image-Guided Medical Intervention.
U.S. Appl. No. 35/508,942 (D. 930,162), filed Feb. 13, 2020 (Sep. 7, 2021), Medical Headset.
16 Augmented Reality Glasses of 2021 (with Features), in Back to News, Dated May 6, 2022, accessed at https://web.archive.org/web/20221127195438/https://circuitstream.com/blog/16-augmented-reality-glasses-of-2021-with-features-breakdowns/.
Everysight, Installing your RX Adaptor, accessed Mar. 13, 2024 at https://support.everysight.com/hc/en-us/articles/115000984571-Installing-your-RX-Adaptor.

(56) References Cited

OTHER PUBLICATIONS

Everysight, Raptor User Manual, copyright 2017, in 46 pages.
Frames Direct, InSpatialRx Prescription Insert, Prescription Insert for Magic Leap 1, accessed Mar. 8, 2024 at https://www.framesdirect.com/inspatialrx-prescription-insert.html.
ISA/220—Notification of Transmittal or Search Report and Written Opinion of the ISA, or the Declaration Mailed on Aug. 11, 2023 for WO Application No. PCT/IB23/054056, 19 page(s).
Reddit, Notice on Prescription Lenses for Nreal Glasses, accessed Mar. 13, 2024 at https://www.reddit.com/r/nreal/comments/x1fte5/notice_on_prescription_lenses_for_nreal_glasses/.
Vuzix Blades, Prescription Lens Installation Guide, copyright 2020.
U.S. Appl. No. 18/857,558, Oct. 17, 2024, Reduction of Jitter in Virtual Presentation.
U.S. Appl. No. 18/398,837, Dec. 28, 2023, Adjustable Augmented Reality Eyewear for Image-Guided Medical Intervention.
U.S. Appl. No. 18/399,433, Dec. 28, 2023, Configurable Augmented Reality Eyewear for Image-Guided Medical Intervention.
U.S. Appl. No. 18/772,578, Jul. 15, 2024, Augmented Reality Eyewear for Image-Guided Medical Intervention.
U.S. Appl. No. 35/508,942, Feb. 13, 2020, Medical Headset.
Augmedics Ltd., 510k Clearance Summary for Augmedics' xvision Spine system, dated Dec. 20, 2019 in 11 pages.
Medtronic Navigation, Inc., StealthStation™ S8 System Manual in 82 pages, Revision 2, Copyright 2018.
Novarad Healthcare IT and Imaging, OpenSight ENGLISH: See 3D Medical Images Using Augmented Reality, dated Mar. 9, 2018, accessed via YouTube on Mar. 11, 2025 at https://www.youtube.com/watch?v=M3yY_b8jT54.

\* cited by examiner

METHODS FOR MEDICAL IMAGE VISUALIZATION

INCORPORATION BY REFERENCE TO ANY PRIORITY APPLICATIONS

This application is a continuation of U.S. patent application Ser. No. 18/365,566, filed Aug. 4, 2023, which is a continuation of International PCT Application PCT/IB2023/054056, filed Apr. 20, 2023, which claims the benefit of U.S. Provisional Patent Application No. 63/333,128, filed Apr. 21, 2022 and of U.S. Provisional Patent Application No. 63/428,781, filed Nov. 30, 2022. The entire contents of each of the foregoing applications is incorporated herein by reference.

FIELD

The present disclosure generally relates to medical visualization, including systems and methods for generating (e.g., computing) three-dimensional (3D) models based on 2D or 3D medical images for use, among other considered medical usages, such as in image-guided surgery, and for generating 3D renderings based on the 2D or 3D medical images (e.g., for output on an augmented reality display).

BACKGROUND

Near-eye display devices and systems, such as head-mounted displays are commonly used in augmented reality systems, for example, for performing image-guided surgery. In this way, a computer-generated three-dimensional (3D) model of a volume of interest of a patient may be presented to a healthcare professional who is performing the procedure, such that the 3D model is visible to the professional engaged in optically viewing an anatomical portion of a patient who is undergoing the procedure.

Systems of this sort for image-guided surgery are described, for example, in Applicant's U.S. Pat. Nos. 9,928,629, 10,835,296, 10,939,977, PCT International Publication WO 2022/053923, and U.S. Patent Application Publication 2020/0163723. The disclosures of all of these patents and publications are incorporated herein by reference.

SUMMARY

In accordance with several embodiments, systems, devices and methods are described that provide enhanced or improved display of 3D models in connection with image-guided medical procedures. For example, the 3D models may be displayed with reduced noise and increased image quality. In some instances, the 3D models may not be displayed with background features (e.g., soft tissue is not displayed when it is bone tissue that is desired to be displayed). In some instances, the 3D models that are generated include implants or hardware (such as screws, rods, cages, pins, tools, instruments, etc.) but not certain types of tissue (e.g., soft tissue, nerve tissue) that is not the focus of the particular medical procedure. For example, the content of the 3D model or rendering that is generated for display may preferentially or selectively include only certain types of content that a clinical professional or other operator would want to see and not "background" content that the clinical professional or other operator does not need to see or does not want to see because it does not impact or affect the medical procedure (e.g., surgical or non-surgical therapeutic procedure or diagnostic procedure). In the example of a spinal surgical procedure, the background content that may be desired to be filtered out or selectively or preferentially not displayed may be soft tissue surrounding or between the vertebrae of the spine and the content that may selectively or preferentially be displayed is the bone tissue (and optionally, any hardware, implant or instruments or tools within the bone, such as screws, rods, cages, etc.).

In accordance with several embodiments, the systems, devices and methods described herein involve automatically segmenting the image(s) (e.g., 3D computed tomography images, 3D magnetic resonance images, other 2D or 3D images) received from an imaging device scan prior to applying one or more 3D model generation algorithms or processes. In accordance with several embodiments, the segmentation advantageously reduces noise around the bone structure and provides a better "starting point" for the 3D model generation algorithms or processes. The segmentation may involve segmenting the 3D image into multiple separate regions, sections, portions, or segments. An entire anatomical portion of a subject (e.g., an entire spine or entire other bone, such as a hip, knee, shoulder, ankle, limb bone, cranium, facial bone, jaw bone, etc.) may be segmented or a subportion of the anatomical portion may be segmented.

Several embodiments are particularly advantageous because they include one, several or all of the following benefits: (i) using a segmented image for 3D image rendering and/or model building to achieve a more accurate and less noisy 3D model and/or visualization of a patient anatomy (e.g., a portion of the patient anatomy); and/or (ii) using artificial intelligence based segmentation in 3D model building to support low-quality intra-operative scanners or imaging devices; and/or (iii) applying different threshold values to different portions of the medical image to achieve better visualization of the patient anatomy; and/or (iv) enhancing a 3D model building while using a model building algorithm which may receive only a single threshold by applying multiple thresholds and/or (v) allowing a user to select different thresholds to be applied on different portions of a medical image (e.g., to improve or optimize visualization).

In accordance with several embodiments, a system for improving display of 3D models in connection with image-guided medical procedures (e.g., surgical or non-surgical therapeutic and/or diagnostic procedures) comprises or consists essentially of a wearable device (e.g., head-mounted unit such as eyewear) including at least one see-through display configured to allow viewing of a region of a body of a patient through at least a portion of the display and at least one processor (e.g., a single processor or multiple processors) configured to perform actions (e.g., upon execution of stored program instructions on one or more non-transitory computer-readable storage media). For example, the at least one processor is configured to receive a three-dimensional (3D) image of the region of the body of the patient, the 3D image having intensity values; segment the 3D image to define at least one region of interest (ROI) of the region of the body (e.g., a portion of a spine or other bone associated with the medical procedure); determine at least one ROI intensity threshold value of the at least one ROI; determine a background intensity threshold value; and generate a 3D rendering of the 3D image.

The generation of the 3D rendering may include, in the at least one defined ROI of the 3D image, rendering based on intensity values of the at least one ROI that satisfy a lowest threshold value of the at least one ROI intensity threshold value and the background intensity threshold value; and, in a background region of the 3D image, rendering based on intensity values of the background region that satisfy the background intensity threshold value. The background region of the 3D image may include a portion of the 3D image which is not an ROI.

The at least one processor may also be configure to cause the 3D rendering to be output to the display of the wearable device.

In some embodiments, the intensity values are values of 3D image voxels of the 3D image.

In some embodiments, the wearable device is a pair of glasses or other eyewear. In some embodiments, the wearable device is an over-the-head mounted unit, such as a headset.

In some embodiments, the wearable device is configured to facilitate display of 3D stereoscopic images that are projected at a distance to align with a natural focal length of eyes (or a natural convergence or focus) of a wearer of the wearable device to reduce vergence-accommodation conflict.

The 3D image may be a computed tomography image, a magnetic resonance image, or other 3D image generated by another 3D imaging modality.

In some embodiments, the at least one processor is configured to display the 3D rendering in alignment by performing registration of the 3D rendering with the body region of the patient (e.g., using one or more markers, such as retroreflective markers that can be scanned or imaged by an imaging device of the wearable device).

In some embodiments, the 3D rendering is a 3D model. The 3D rendering may be output for display as a virtual augmented reality image. The virtual augmented reality image may be projected directly on a retina of the wearer of the wearable device. The virtual augmented reality image may be presented in such a way that the wearer can still see the physical region of interest through the display.

In some embodiments, the at least one processor is configured to generate the 3D rendering by changing the determined intensity values of the 3D image into a value which does not satisfy the lowest threshold value.

In some embodiments, the background region of the 3D image includes soft tissue.

In some embodiments, the at least one processor is further configured to repeatedly adjust the at least one ROI intensity threshold value and the background feature intensity threshold value according to input from a user; and repeatedly generate a 3D rendering of the 3D image based on the adjusted values of the at least two intensity thresholds. Only one of the threshold values may be adjusted in some embodiments.

In accordance with several embodiments, a system for improving display of 3D models in connection with image-guided surgery comprises or consists essentially of a head-mounted unit including at least one see-through display configured to allow viewing of a region of a spine of a patient through at least a portion of the display and at least one processor configured to (e.g., upon execution of program instructions stored on one or more non-transitory computer-readable storage media): receive a three-dimensional (3D) image of the region of the spine of the patient, the 3D image having intensity values, segment the 3D image to define multiple regions of interest (ROI) of the spine (e.g., multiple vertebrae or multiple vertebral segments); determine a ROI intensity threshold value for each of the multiple ROIs of the spine; determine a background intensity threshold value; generate a 3D rendering (e.g., 3D model) of the 3D image; and cause the 3D rendering to be output to the display as a virtual augmented reality image. The generation of the 3D rendering includes, in the multiple ROIs of the 3D image, rendering based on the determined ROI intensity values of the multiple ROIs that satisfy a lowest threshold value of the intensity threshold value and the background intensity threshold value and, in a background region of the 3D image, rendering based on intensity values of the background region that satisfy the background intensity threshold value. The background region of the 3D image includes a portion of the 3D image which is not an ROI.

In some embodiments, the intensity values are voxel values of the 3D image.

In some embodiments, the head-mounted unit is a pair of glasses or other form of eyewear, including eyewear without lenses. In some embodiments, the head-mounted unit is an over-the-head mounted unit (e.g. a headset).

In some embodiments, the display is configured to be displayed directly on a retina of a wearer of the head-mounted unit.

In some embodiments, the at least one processor is configured to display the 3D rendering in alignment by performing registration of the 3D rendering with the region of the spine.

In some embodiments, the at least one processor is configured to generate the 3D rendering by changing the determined intensity values of the 3D image into a value which does not satisfy the lowest threshold value.

In some embodiments, the at least one processor is further configured to repeatedly adjust the at least one ROI intensity threshold value and the background feature intensity threshold value according to input from a user and repeatedly generate a 3D rendering of the 3D image based on the adjusted values of the at least two intensity thresholds.

An embodiment of the present disclosure that is described hereinafter provides a computer-implemented method that includes obtaining a three-dimensional (3D) image of a region of a body of a patient, the 3D image having feature values. The 3D image is segmented to define one or more regions of interest (ROIs). The one or more regions of interest may include one or more portions of a bone or joint (e.g., a portion of a spine, individual vertebrae of a portion of a spine, a particular spinal segment, a portion of a pelvis or sacroiliac region, or other bone or joint). At least one region of interest (ROI) feature threshold is determined. A background feature threshold is determined. A 3D model is generated from the 3D image based on the determined at least one ROI feature threshold, the determined background feature threshold, and the segmentation. The 3D model is outputted for display to a user.

In some embodiments, the feature values are intensity values, the ROI feature threshold is an ROI intensity threshold, and the background feature threshold is a background intensity threshold.

In some embodiments, the intensity values are the 3D image voxel values, and the intensity thresholds are the 3D image voxel thresholds.

In an embodiment, the method further includes generating a 3D rendering of the 3D image, wherein the generation of the 3D rendering includes (i) in the at least one ROI of the 3D image, rendering based on feature values of the at least one ROI that satisfy the lowest threshold of the at least one ROI feature threshold and the background feature threshold, and (ii) in a background region of the 3D image, rendering based on feature values of the background region that satisfy the background feature threshold, wherein the background region of the 3D image includes a portion of the 3D image which is not an ROI. The 3D model is outputted for display to a user.

In another embodiment, generating the 3D model includes using a 3D model generation algorithm and providing a feature threshold as input to the 3D model generation algorithm.

In some embodiments, the 3D model generation algorithm is a marching cubes algorithm.

In some embodiments, the provided feature threshold corresponds to one of the at least one ROI feature threshold.

In some embodiments, the provided feature threshold is determined based on the at least one ROI feature threshold and the background feature threshold.

In other embodiments, the provided feature threshold is selected as the lowest of the at least one ROI feature threshold value and the background feature threshold value.

In some embodiments, the generation of the 3D model includes selecting feature values of the 3D image satisfying the provided feature threshold and omitting portions of the background region of the 3D image with selected feature values from being an input to the generation of the 3D model.

In other embodiments, the omitting of portions of the background region includes changing the selected feature values of the portions of the background region into a value that does not satisfy the provided feature threshold.

In an embodiment, the determination of the at least one ROI feature threshold and of the background feature threshold includes receiving input values for at least one of: the at least one ROI feature threshold or the background feature threshold.

In some embodiments, the input values are received for the at least one ROI feature threshold and the background feature threshold.

In some embodiments, the input values are received from a user.

In some embodiments, the receiving of the input values from the user includes generating a Graphical User Interface (GUI) element to be displayed to the user, the GUI element allowing the user to adjust the input values, and the rendering and displaying of the 3D rendering is iteratively performed in correspondence to the user adjustment of the input values.

In an embodiment, in response to a request of the user, the 3D model is generated based on current input values for at least one of: the at least one ROI feature threshold or the background feature threshold.

In another embodiment, the input values are received for the at least one ROI feature threshold and the background feature threshold.

In some embodiments, the method further includes displaying a default 3D model based on default values for the at least one ROI feature threshold and the background feature threshold, and displaying the default 3D model to the user.

In some embodiments, the determining of the at least one ROI feature threshold includes, when multiple ROIs are considered, determining respective multiple ROI feature thresholds.

In some embodiments, the determining of the at least one ROI feature threshold includes setting a feature threshold value that differentiates bone from soft tissue.

In other embodiments, the determining of the background feature threshold includes setting a feature threshold value that differentiates metal from bone.

In an embodiment, the method further includes using the 3D model with an image-guided system. The image-guided system and methods described herein can be surgical, non-surgical or diagnostic.

In another embodiment, the image-guided system is an augmented or mixed reality system including a direct see-through display, such as a Head Mounted Display (HMD). In some embodiments, the image-guided system is an augmented or mixed reality system that does not include a head mounted display/component or includes both head mounted and non-head mounted displays/components.

In some embodiments, the segmentation is performed based on one or more deep learning networks. In some embodiments, the deep learning networks are convolutional neural networks.

There is additionally provided, in accordance with another embodiment of the present disclosure, a computer-implemented method including obtaining a three-dimensional (3D) image of a region of a body of a patient, the 3D image having features. The 3D image is segmented to define one or more regions of interest (ROIs). At least one ROI feature threshold is determined. A background feature threshold is determined. A 3D rendering of the 3D image is generated, wherein the generation of the 3D rendering includes (i) in the at least one defined ROI of the 3D image, rendering based on feature values of the at least one ROI that satisfy the lowest threshold of the at least one ROI feature threshold and the background feature threshold, and (ii) in a background region of the 3D image, rendering based on feature values of the background region that satisfy the background feature threshold, wherein the background region of the 3D image includes a portion of the 3D image which is not an ROI. The 3D model is outputted for display to a user.

In some embodiments, the method further includes generating a 3D model based on the determined at least one ROI feature threshold, the determined background feature threshold, and the segmentation. The 3D model is displayed on a display.

In some embodiments, generating the 3D model includes using a 3D model generation algorithm and providing a feature threshold as input to the 3D model generation algorithm.

In an embodiment, the provided feature threshold is selected to be the lowest of the at least one ROI feature threshold and the background feature threshold.

In another embodiment, the provided feature threshold is the at least one ROI feature threshold, and the portions of the background region having selected feature values which do not satisfy the background intensity threshold are omitted.

In some embodiments, the determination of the at least ROI feature threshold and of the background feature threshold includes receiving input values for at least one of: the at least one ROI feature threshold or the background feature threshold.

In some embodiments, the method further includes displaying a default 3D rendering based on default values for the at least one ROI feature threshold and the background feature threshold, and displaying the default 3D rendering to the user.

There is further provided, in accordance with another embodiment of the present disclosure, a system for image-guided surgery (or other procedures such as non-surgical procedures and diagnostics), the system including at least one display, and at least one processor. The at least one processor is configured to (i) receive a three-dimensional (3D) image of a region of a body of a patient, the 3D image having intensity values, (ii) compute a 3D model of the region based on at least two intensity threshold values applied to the 3D image, and (iii) cause the computed 3D model to be output for display on the at least one display.

In some embodiments, the at least one display includes a see-through display configured to allow viewing of a body of a patient through at least a portion of the display.

In some embodiments, the see-through display is included in a head-mounted unit. The head-mounted unit may provide elimination of attention shift and a reduced (e.g., minimized) line of sight interruption.

In other embodiments, the computed 3D model is displayed in alignment with the body of the patient as viewed through the see-through display. The 3D model may be provided in a 3D stereoscopic view. The virtual images may be projected at 50 cm in order to align with a normal focal distance of the eyes so as to reduce "vergence-accommodation conflict", which can result in fatigue, headache, or general discomfort. The line of sight may be at approximately 30 degrees.

In other embodiments, the at least one processor is configured to display in alignment by performing registration of the 3D model with the body of the patient.

In some embodiments, the intensity values are the 3D image voxel values.

In an embodiment, the at least one display includes a stationary display. In some embodiments, the display is a display of a head-mounted device, including but not limited to glasses, googles, spectacles, visors, monocle, other eyewear, or over-the-head headset. In some embodiments, the head-mounted displays are not used or used together with stand-alone displays, such as monitors, portable devices, tablets, etc. The display may be a hands-free display such that the operator does not need to hold the display.

The head-mounted device may alternatively be a wearable device on a body part other than the head (e.g., a non-head-mounted device). The head-mounted device may be substituted with an alternative hands-free device that is not worn by the operator, such as a portal, monitor or tablet. The display may be a head-up display or heads-up display.

In an embodiment, the at least one processor is further configured to segment the 3D image to define one or more regions of interest (ROIs), and the computation of the 3D model is further based on the segmentation.

In another embodiment, the at least two intensity threshold values include at least one ROI threshold intensity value and a background threshold intensity value, and the at least one processor is further configured to (i) compute the 3D model by selecting intensity values of the 3D image satisfying the lowest intensity threshold value of the at least one ROI threshold intensity value, and (ii) omit portions of a background region of the 3D image with intensity values between the lowest intensity threshold value of the at least one ROI threshold intensity values and the background threshold intensity value from being an input to the generation of the 3D model.

In some embodiments, the at least one processor is configured to generate the 3D model by changing the selected intensity values of the 3D image into a value which does not satisfy the lowest intensity threshold value.

In some embodiments, the at least two intensity thresholds include at least one region of interest (ROI) intensity threshold to be applied to one or more ROIs and a background intensity threshold to be applied to at least a background region of the 3D image, and the background region of the 3D image includes a portion of the 3D image which is not an ROI.

In other embodiments, the at least one processor is further configured to (i) repeatedly adjust the at least two intensity thresholds according to input from a user, and (ii) repeatedly generate a 3D rendering of the 3D image based on the adjusted values of the at least two intensity thresholds.

In an embodiment, a method is provided of generating at least one of a 3D model and images for display.

In an embodiment, a system is provided, that includes at least one processor configured for facilitating generation of at least one of a 3D model and images, the system further including a display device configured to display the at least one of a 3D model and images.

Also described and contemplated herein is the use of any of the apparatus, systems, or methods for the treatment of a spine through a surgical intervention.

Also described and contemplated herein is the use of any of the apparatus, systems, or methods for the treatment of an orthopedic joint through a surgical intervention, including, optionally, a shoulder, a knee, an ankle, a hip, or other joint.

Also described and contemplated herein is the use of any of the apparatus, systems, or methods for the treatment of a cranium through a surgical intervention.

Also described and contemplated herein is the use of any of the apparatus, systems, or methods for the treatment of a jaw through a surgical intervention.

Also described and contemplated herein is the use of any of the apparatus, systems, or methods for diagnosis of a spinal abnormality or degeneration or deformity.

Also described and contemplated herein is the use of any of the apparatus, systems, or methods for diagnosis of a spinal injury.

Also described and contemplated herein is the use of any of the apparatus, systems, or methods for diagnosis of joint damage.

Also described and contemplated herein is the use of any of the apparatus, systems, or methods for diagnosis of an orthopedic injury.

In accordance with several embodiments, any of the methods described herein may include diagnosing and/or treating a medical condition, the medical condition comprising one or more of the following: back pain, spinal deformity, spinal stenosis, disc herniation, joint inflammation, joint damage, ligament or tendon ruptures or tears.

In accordance with several embodiments, a method of presenting one or more images on a wearable display is described and/or illustrated herein during medical procedures, such as orthopedic procedures, spinal surgical procedures, joint repair procedures, joint replacement procedures, facial bone repair or reconstruction procedures, ENT procedures, cranial procedures or neurosurgical procedures.

For purposes of summarizing the disclosure, certain aspects, advantages, and novel features of embodiments of the disclosure have been described herein. It is to be understood that not necessarily all such advantages may be achieved in accordance with any particular embodiment of the disclosure disclosed herein. Thus, the embodiments disclosed herein may be embodied or carried out in a manner that achieves or optimizes one advantage or group of advantages as taught or suggested herein without necessarily achieving other advantages as may be taught or suggested herein. The systems and methods of the disclosure each have several innovative aspects, no single one of which is solely responsible for the desirable attributes disclosed herein. The methods summarized above and set forth in further detail below describe certain actions taken by a practitioner; however, it should be understood that they can also include the instruction of those actions by another party. Thus, actions such as "adjusting a threshold" include "instructing the adjustment of a threshold."

The present disclosure will be more fully understood from the following detailed description of the embodiments thereof, taken together with the drawings.

BRIEF DESCRIPTION OF THE DRAWINGS

Non-limiting features of some embodiments are set forth with particularity in the claims that follow. The following drawings are for illustrative purposes only and show non-limiting embodiments. Features from different figures may be combined in several embodiments. It should be understood that the figures are not necessarily drawn to scale. Distances, angles, etc. are merely illustrative and do not necessarily bear an exact relationship to actual dimensions and layout of the devices illustrated.

DETAILED DESCRIPTION OF THE PREFERRED EMBODIMENT

Overview

Figure 1:
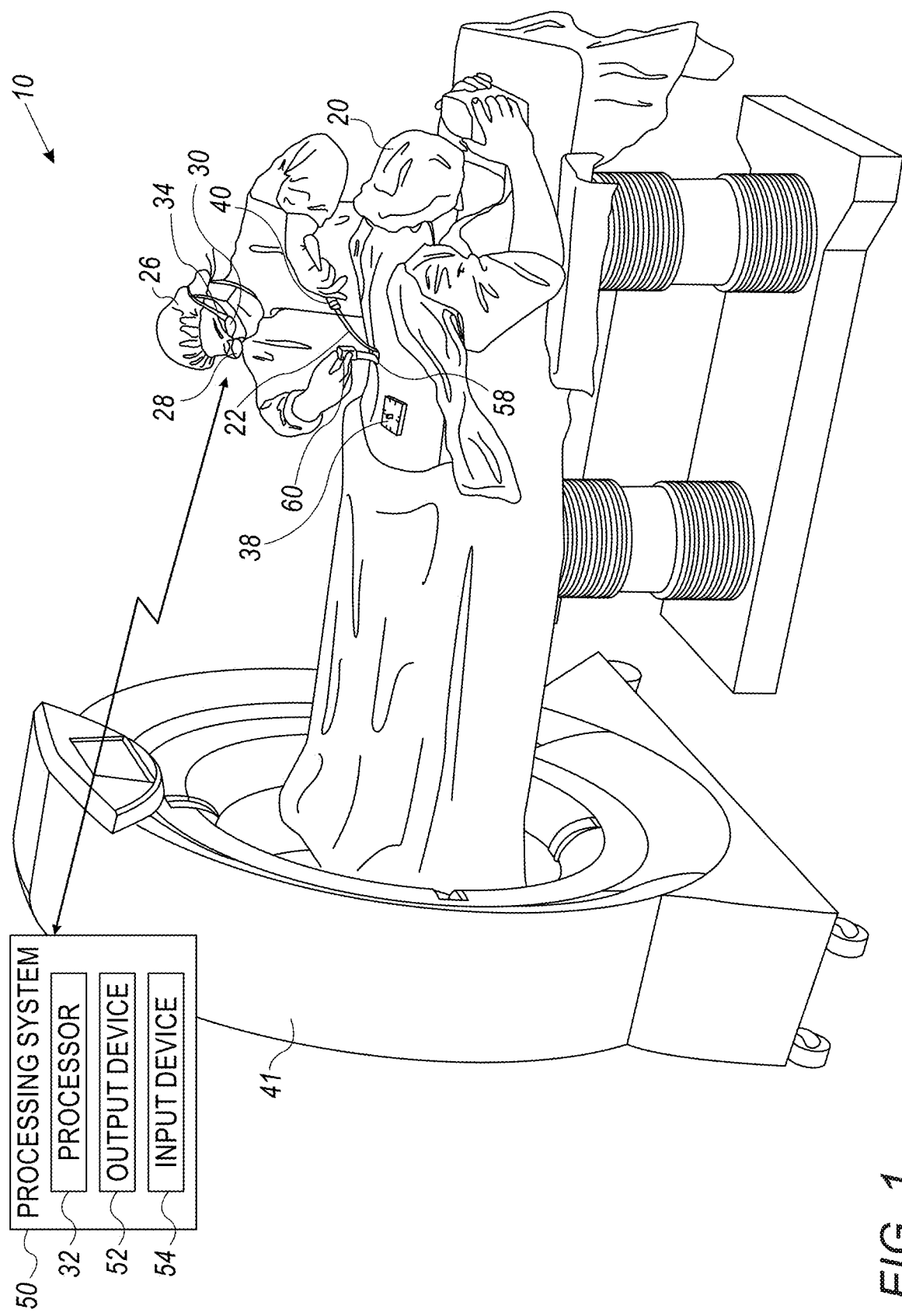
FIG. 1 is a schematic, pictorial illustration of an example system for image-guided surgery or other medical intervention utilizing a head-mounted display, in accordance with an embodiment of the disclosure.

A three-dimensional (3D) model of a volume of interest of a patient may include irrelevant or undesired information around the volume of interest or around the model, such as irrelevant or undesired objects or tissue and/or image noise. A user may adjust or cause adjustment of a threshold (e.g., radiodensity threshold value such as using a Hounsfield Unit scale) of an image (e.g., a CT image or other 2D or 3D medical image), to suppress the irrelevant or undesired information. However, reducing irrelevant or undesired information this way may cause loss of some of the relevant or desired information. For example, a 3D image may include metal objects characterized by very high radiodensity values and bone characterized by lower radiodensity values. Setting a high enough threshold may show the metal objects and remove noise but may well erode or remove some bone structure features in the image.

In accordance with several embodiments, a pre-processing stage may be included to automatically segment the medical image (e.g., 3D CT scan) prior to generation of a 3D model (e.g., generating a 3D model by applying one or more 3D model generation algorithms or processes). The segmentation may advantageously reduce the noise around the bone structure and provide a better "starting point" for the 3D model generation. The segmentation may be applied to the entire medical image or to one or more portions, regions or segments of the medical image.

Image-guided surgery employs tracked surgical instruments and images of the patient anatomy in order to guide the procedure. In such procedures, a proper visualization of regions of interest of the patient anatomy, including tissue of interest, is of high importance. Enhanced or improved visualization may also advantageously provide increased user adoption and enhance user experience.

In particular, during image-guided surgery or other medical intervention (e.g., procedures employing augmented reality technology, virtual reality technology or mixed-reality technology), the 3D model of a volume of interest of the patient upon whom the surgery or other medical intervention (including diagnostic and/or therapeutic intervention) is being performed may be aligned with tools or devices used during the surgery or intervention and/or with the anatomical portion of the patient undergoing surgery or other medical intervention. Such 3D model may be derived from a 3D medical image, such as a 3D CT image or 3D MR image. In accordance with several embodiments, a proper modeling based on the 3D medical image is important for providing the user with the required and accurate information for navigating a medical tool on anatomical images derived from the 3D medical image (e.g., slices, 3D model and/or 2D images) and for accurate and/or proper augmentation (e.g., in alignment) of the 3D model with the optically viewed (e.g., with a near-eye display device) anatomical portion of the patient when augmented-reality is used.

Some embodiments of the present disclosure provide computer-implemented methods for generating a 3D model from at least one 3D medical image. The methods include obtaining one or more 3D images of at least a region of a body of a patient (e.g., including a cervical spine region, a thoracic spine region, a lumbosacral spine region, a cranial region, an ENT-associated region, a facial region, a hip region, a shoulder region, a knee region, an ankle region, a joint region, or a limb region), the 3D image having one or more feature values, such as image intensity values on a gray-scale, RGB values, gradients, edges and/or texture. In some embodiments, the 3D image is first segmented to include or identify one or more regions of interest (ROIs). At least one ROI feature threshold may be determined. At least one background feature threshold may also be determined. In some embodiments, a 3D model is generated from the 3D image, based on the determined at least one ROI feature threshold, the determined at least one background feature threshold, and the segmentation. The 3D model may then be saved for use in image-guided surgery and/or systems, e.g., to be displayed to a user on a display of a wearable (e.g., head-mounted or near-eye or direct see-through) display device and/or on a separate or stationary display monitor or device (e.g., a standalone or separate portal, tablet or monitor).

In some embodiments, the 3D image is processed to only show the at least one ROI and to only show background information above the background feature threshold. This may be performed, for example, by segmenting the image and applying different feature thresholds to different portions of the image. In such embodiments, irrelevant or undesired background information can be suppressed using a high background feature threshold, without desired features inside the at least one ROI being eroded.

As noted above, the techniques disclosed herein may advantageously present (e.g., cause to be displayed) maximum or an increased amount of information obtained from ROIs of the 3D medical image and filter out some of the background of the 3D medical image, which may include, for example, noise or information of less interest. Accordingly, in some embodiments, the at least one processor may be configured to apply the lowest feature threshold to the ROIs (e.g., even if a specific ROI's feature threshold is not or different than the lowest feature threshold). In some embodiments, the at least one processor may be configured to apply the background feature threshold to the entire image while determining in each region or segment of the image the lowest feature threshold applied to the region or segment as the specific region or segment feature threshold. For example, for a specific ROI, a background feature threshold and an ROI feature threshold are applied. One may expect that the ROI feature threshold would be the lowest but in case the background feature threshold is the lowest, then the background feature threshold value would determine the threshold value for the specific ROI. Specifically, a background feature (e.g., intensity) threshold may be set to a higher value than any of one or more ROI feature (e.g., intensity) thresholds, for example. As a result, the processed 3D image (e.g., processed via volume rendering) may show only information contained in the at least one ROI and background information (e.g., objects) of sufficient intensity, while removing irrelevant or undesired background information. The processed 3D image may show in an ROI bone structure with metal surgical objects in the background, without showing irrelevant anatomy (e.g., other bones or other type of tissue) or an image suffering from background image noise.

In some embodiments, at least two feature thresholds are provided that include at least one region of interest (ROI) feature threshold to be applied to the one or more ROIs, and a background feature threshold to be applied to a background region of the 3D image. The background region of the 3D image may include a portion of the 3D image which is not an ROI or the portion or all portions of the 3D image which are not an ROI. By suppressing the values of the background regions (e.g., values of 3D image voxels) which do not satisfy the background feature threshold, an effective unique threshold may be obtained. This suppression step may be used for generating a 3D model using an algorithm that accepts only one threshold value (e.g., marching cubes algorithm), while at the same time maximizing or otherwise increasing information obtained from ROIs of the 3D medical image and filtering out some of the background of the 3D medical image, which may be an area of less interest.

In some embodiments of the computer-implemented method, before the 3D model is computed, a 3D rendering based on a processed 3D image (e.g., a segmented image) is displayed to a user, such as a surgeon or other healthcare professional. The user may view the 3D rendering on a monitor or a display (e.g., a graphical user interface display on a monitor or on a near-eye display of a head-mounted, direct see-through, or near-eye display device). The graphical user interface display may allow the user to adjust the at least one ROI intensity threshold and/or the background intensity threshold, to thereby modify the look of the 3D rendering. This way, the user can advantageously optimize the rendered 3D image by selecting and/or identifying optimal and/or desired feature thresholds, based on which the 3D model will be computed.

The 3D rendering may be made of the original image voxels, or may be a result of further image processing steps applied to the 3D image, such as surface ray casting. Further image processing of the 3D image beyond producing a 3D rendering using the native 3D image voxels can have advantages. For example, using ray casting may facilitate interpolation between, e.g., voxel intensity values, to produce a smoother look. Also, some methods such as surface ray cast rendering use only a portion of the information included in the native 3D image (e.g., use only voxels encountered by rays, provided the voxels have feature values such as intensities above a threshold). In accordance with several embodiments, using only a subset of the voxels minimizes or otherwise advantageously reduces computation effort and time required to generate a 3D rendering. This reduction may be particularly important as the user manipulates the view of the rendering (e.g., views the rendering from different points of view), which requires repeated computations of the 3D rendering.

In accordance with several embodiments, the 3D rendering generation process comprises the steps of:

In the at least one ROI of the 3D image, rendering based on feature values of the at least one ROI which satisfy the lowest threshold of the at least one ROI feature threshold and the background feature threshold.

In a background region of the 3D image, rendering based on feature values of the background region which satisfy the background feature threshold, wherein the background region of the 3D image comprises a portion of the 3D image which is not an ROI.

As noted above, to generate the 3D model, two thresholds (e.g., the ROI feature threshold and the background feature threshold) may be determined by a user (or automatically by at least one processor, e.g., based on accumulated data or based on trained machine learning algorithms or neural networks). However, some 3D model generation algorithms (e.g., surface building algorithms, such as the Marching Cubes algorithm), may receive as input only a single threshold value. In accordance with several embodiments, the techniques disclosed herein advantageously solve the limitation of only a single allowed input threshold by:

Using the lowest ROI feature threshold value with the algorithm (e.g., running the Marching Cubes algorithm) to delineate ROI regions.

Visualizing only ROI regions with feature values higher than a lowest ROI feature threshold.

Visualizing only portions of any other regions, including background regions, with feature values higher than a background feature threshold.

In accordance with several embodiments, background information (e.g., voxel values) having feature values higher than the ROI feature threshold but lower than the background feature threshold is removed (e.g., in order not to model and display irrelevant or undesired information). In some embodiments, such removal is performed by determining the value of such voxels to a value which does not satisfy the ROI feature threshold(s), e.g., equal to or lower than the ROI feature threshold (e.g., ROI threshold-C) while C is a constant (non-negative number): C>0. In some embodiments, the subtracting of such a constant may allow further smoothing of the visualization (e.g., the 3D model).

As described above, using two thresholds, called herein TH ROI and TH Background, may allow showing ROI information and some selected background objects, respectively. If ROI information to be visualized has to meet multiple thresholding conditions (e.g., multiple tissue types have to be visualized, such as fat, muscle and bone), then two or more (e.g., multiple) ROI thresholds (e.g., one for each ROI type), TH(j) ROI, j=1, 2, . . . , may be defined and used in segmentation, volume rendering and/or generating a 3D model. In some embodiments when only one threshold may be input to a 3D model generation algorithm, then the lowest of {TH(j)ROI} may be used.

In one embodiment, a trained neural-network (NN) based segmentation algorithm is provided. The disclosed segmentation algorithm classifies different regions of 3D image as ROI and background and delineates one from another. For example, in orthopedic image-guided applications (such as surgery or other procedures, such as non-surgical or diagnostic procedures), the disclosed segmentation algorithm may be trained to classify vertebrae column and the Iliac and Sacrum as "Spine". According to some embodiments, the vertebrae, each vertebra, the Iliac and/or the Sacrum may be segmented separately. According to some embodiments, screws, implants and/or inter-bodies included in the scan may also be classified by the algorithm as "Spine" (or the desired category to be shown). Soft tissues, the rib cage and instruments such as clamps, retractors and rods that are included in the scan may be classified as "background." In some implementations, the segmentation of the spine is done on the whole spine anatomy included in the scan. In some implementations, the segmentation of the spine is performed on portions of the spine anatomy (e.g., just the lumbosacral region, just the lumbar region, just the thoracic region, just the sacral region, just the sacroiliac region, just the cervical region, or combinations thereof) or on individual vertebrae, and/or on anatomical portions of individual vertebrae. The segmentation may further be used for creating a virtual 3D model of the scanned spine area, leaving out, for example, soft tissue, ribs and rods. However, in some embodiments, such left-out elements may be segmented and classified as ROI, such as ribs.

In some embodiments, a segmentation method is applied for generating a 3D model without resorting to a subsequent model building step and algorithm. To this end, the segmentation may use ROI and background feature threshold values in the delineation process. In some embodiments, the segmentation algorithm uses the minimal ROI feature threshold value to segment a first group of regions (e.g., bone regions) in the 3D image, with values above the minimal ROI feature threshold value. Then, the segmentation algorithm uses the background intensity threshold to further segment a second group of regions in the 3D image, with values above the background feature threshold value. A processed image is then generated that visualizes only first and second regions obtained by the segmentation algorithm. If the spatial resolution of the segmentation algorithm is sufficiently high, as well as that of the native 3D image, the segmentation algorithm may be sufficient to create a 3D model (e.g., without resorting to surface building algorithms, such as the Marching Cubes algorithm).

In some embodiments, the at least one processor is configured to use the segmentation to generate a digitally reconstructed radiograph (DRR) of one or more ROIs only. To this end, the at least one processor may be configured to omit the background region, for example, by setting voxel feature values in the medical 3D image (e.g., an input 3D Digital Imaging and Communications in Medicine (DICOM) image) segmented as background to zero. The DRRs may be generated by summarizing feature values in one dimension or by using methods such as Siddon's algorithm published in 1985 by Robert L. Siddon. For example, in Siddon's algorithm, the index of each voxel along a certain projection ray and the interesting length of that ray within that voxel may be computed by four multiplications. Refinements or modifications to Siddon's algorithm, or alternative algorithms (e.g., for calculating radiological paths through pixel or voxel spaces), may also be used.

A further embodiment provides an augmented-reality system for image-guided surgery (or other procedures such as non-surgical procedures and diagnostics), the system comprising (i) a see-through augmented-reality display configured to allow viewing of a body of a patient through at least a portion of the display by the user (e.g., wearing a head-mounted unit), and at least one processor, which is configured to receive the 3D image of a region of the body of the patient and compute a 3D model of the region based on at least two intensity thresholds applied to the 3D image, and present the computed 3D model on the display in alignment with the body of the patient viewed through the display, e.g., for better spatial awareness.

In some embodiments, accurate and/or proper augmentation (e.g., alignment) of a navigated medical tool with images derived from the medical image (e.g., slices, 3D model, 2D images and/or DRR images) and, optionally, accurate and/or proper augmentation of the 3D model with an optically viewed anatomical portion is facilitated by a registration step of the 3D medical image, e.g., via artificial fiducials in the 3D medical image and by utilizing a tracking system. Specifically, when using a direct see-through or head-mounted display, accurate and/or proper augmentation of the 3D model with an optically viewed anatomical portion as viewed from the point of view of a professional wearing the head-mounted display, may be achieved by utilizing a tracking device for tracking at least the position of the head-mounted display relative to the anatomical portion. In some embodiments the tracking system may be mounted on the head-mounted display device. Systems of this sort using augmented-reality for image-guided surgery (or other procedures such as non-surgical procedures and diagnostics), are described, for example, in the above incorporated Applicant's U.S. Pat. Nos. 9,928,629, 10,939,977, PCT International Publication WO 2022/053923, and U.S. Patent Application Publication 2020/0163723.

The disclosure describes, for example, a method of generating a 3D model and/or images for display (e.g., to facilitate image-guided surgery using a direct see-through or head-mounted augmented reality display device) such as described and/or illustrated hereinafter. The disclosure further describes a system comprising at least one processor for generating a 3D model and/or images for display, and a display device configured to display the 3D model and/or images (e.g., to facilitate image-guided surgery using a head-mounted augmented reality display device) such as described and/or illustrated hereinafter.

Finally, as noted above, one common type of 3D medical image in use is a 3D CT image. Another type of 3D medical image that can be used is a 3D MM image. The method can use, mutatis mutandis, 2D or 3D medical images derived from other imaging modalities, such as ultrasound, positron emission tomography (PET), and optical coherence tomography (OCT). Therefore, the above-described methods may be applied to other types of medical acquisitions (e.g., medical scans or images), including electroencephalogram (EEG) imaging, and to other areas or organs of the body, such as skull or cranium, knees, hips, shoulders, sacroiliac joints, ankles, ear, nose, throat, facial regions, elbows, other joint regions or orthopedic regions, gastrointestinal regions, etc. Accordingly, the feature values may be selected as any relevant physiological or electrophysiological values, such as blood and neural activation velocities, respectively, or speeds as derived from the image features.

The systems and methods described herein may be used in connection with surgical procedures, such as spinal surgery, joint surgery (e.g., shoulder, knee, hip, ankle, other joints), orthopedic surgery, heart surgery, bariatric surgery, facial bone surgery, dental surgery, cranial surgery, or neurosurgery. The surgical procedures may be performed during open surgery or minimally-invasive surgery (e.g., surgery during which small incisions are made that are self-sealing or sealed with surgical adhesive or minor suturing or stitching. However, the systems and methods described may be used in connection with other medical procedures (including therapeutic and diagnostic procedures) and with other instruments and devices or other non-medical display environments. The methods described herein further include the performance of the medical procedures (including but not limited to performing a surgical intervention such as treating a spine, shoulder, hip, knee, ankle, other joint, jaw, cranium, etc.).

System Description

FIG. 1 is a schematic, pictorial illustration of an example system 10 for image-guided surgery or other medical intervention utilizing a head-mounted display such as a direct see-through display, in accordance with an embodiment of the disclosure. FIG. 1 is a pictorial illustration of the system as a whole, including showing, by way of example, a head-mounted display unit 28 in a form of eye-glasses, spectacles, or other eyewear that is used in system 10. Alternative types of a head-mounted unit, such as ones based on a helmet, visor, or over-the-head mounted unit that the surgeon wears, may be used in system 10. Alternatively, other wearable or hands-free devices, units or displays may be used.

In accordance with several embodiments, system 10 is applied in a medical procedure on a patient 20 using image-guided intervention. In this procedure, a tool 22 is inserted via an incision (e.g., minimally-invasive or self-sealing incision) in the patient's back in order to perform a surgical intervention. Alternatively, system 10 and the techniques described herein may be used, mutatis mutandis, in other surgical or non-surgical medical or diagnostic procedures.

In the pictured embodiment, a user of system 10, such as a healthcare professional 26 (e.g., a surgeon performing the procedure), wears the head-mounted display unit 28. In various embodiments, the head-mounted display unit 28 includes one or more see-through displays 30, for example as described in the above-mentioned U.S. Pat. No. 9,928,629 or in the other patents and applications cited above that are incorporated by reference. Such see-through displays may include an optical combiner that is controlled by a computer processor (e.g., a computer processor 32 in a central processing system 50 and/or a dedicated computer processor in the head-mounted display unit 28) to display an augmented-reality image to the healthcare professional 26. The image is presented on a see-through display 30 (e.g., as a stereoscopic near-eye display) such that a computer-generated image is projected in alignment with the anatomy of the body of patient 20 that is visible to professional 26 through a portion of the see-through display. In some embodiments, one or more projected computer-generated images include a virtual image of tool 22 overlaid on a virtual image of at least a portion of the patient's anatomy (such as slices, the 3D model or 2D images derived from the 3D medical image, e.g., of a portion of the spine). Specifically, a portion of the tool 22 that would not otherwise be visible to the healthcare professional 26 (for example, by virtue of being hidden by the patient's anatomy) is included in the computer-generated image.

In image-guided surgery or in surgeries utilizing augmented reality systems, a bone-anchoring device may be used as a fiducial marker or may be coupled with such a marker, for indicating the patient's body location in a coordinate system. In system 10, for example, an anchoring device is coupled with a marker that is used to register a region of interest (ROI) of the patient body with a CT scan or other medical images of the ROI (e.g., preoperative, or intraoperative CT or fluoroscopic image). During the procedure, a tracking system (e.g., an IR tracking system of the head-mounted display unit 28) tracks a marker mounted on the anchoring device and a tool that includes a tool marker. Following that, the display of the CT or other medical image data (which may include, for example, a model generated based on such data) on a near-eye display may be aligned with the professional's actual view of the ROI based on this registration. In addition, a virtual image of the tool 22 may be displayed on the CT or other 3D image model based on the tracking data and the registration. The user (e.g., professional 26) may then navigate the tool 22 based on the virtual display of the tool 22 with respect to the patient image data, and optionally, while the 3D model is aligned with the professional's view of the patient or ROI.

According to some aspects, the 3D image or model presented on see-through display 30 is aligned with the patient's body. According to some aspects, allowed alignment error (or allowed misalignment) may not be more than about two to three mm or may be less than four mm or less than five mm or about one to two mm or less than one mm. In one embodiment, the allowed alignment error is less than one mm. In order to account for such a limit on error in alignment of the patient's anatomy with the presented images, the position of the patient's body, or a portion thereof, with respect to the head-mounted unit may be tracked. According to some aspects, the 3D model presented on see-through display 30 is misaligned with the patient's body (e.g., having a misalignment greater than the allowed misalignment).

A patient marker 60 attached to an anchoring implement or device such as a clamp 58 or a pin, for example, may be used for this purpose, as described further hereinbelow. In some embodiments, a registration marker, such as registration marker 38, may be used for registering the 3D image with the patient anatomy, e.g., in a preceding registration procedure. In some embodiments registration marker 38 may be removed once the registration is complete. According to some embodiments, patient marker 60 and registration marker 38 may be combined into a single marker. Anchoring devices, markers and registration systems and methods of this sort for image-guided surgery are described, for example, in the above incorporated U.S. Pat. Nos. 9,928,629, 10,835,296 and 10,939,977, and in addition in Applicant's U.S. Patent Application Publication 2021/0161614, U.S. Patent Application Publication 2022/0142730, U.S. Patent Application Publication 2021/0386482, U.S. Patent Application Publication 2023/0009793, and PCT International Publication WO 2023/026229, all of which are incorporated herein by reference.

When an image of tool 22 is incorporated into the image that is displayed on head-mounted display unit 28, the position of the tool 22 with respect to the patient's anatomy should be accurately reflected. For this purpose, the position of the tool 22 or a portion thereof (e.g., a tool marker 40) is tracked by system 10 (e.g., via a tracking system built into the head-mounted display unit 28). In some embodiments, it is desirable to determine the location of the tool 22 with respect to the patient's body such that errors in the determined location of the tool 22 with respect to the patient's body are typically less than three mm or less than two and a half mm or less than two mm.

In some embodiments, head-mounted display unit 28 includes a tracking sensor 34 to facilitate determination of the location and orientation of head-mounted display unit 28 with respect to the patient's body (e.g., via patient marker 60) and/or with respect to tool 22 (e.g., via a tool marker 40). Tracking sensor 34 can also be used in finding the position and orientation of tool 22 (e.g., via tool marker 40) with respect to the patient's body (e.g., via patient marker 60). In one embodiment, tracking sensor 34 comprises one or more image-capturing or image-acquiring devices, such as a camera (e.g., infrared camera, visible light camera, and/or an RGB-IR camera), which captures or acquires images of patient marker 60 and/or tool marker 40, and/or other landmarks or markers. The tracking sensor 34 may comprise an optical tracking device, an RFID reader, an NFC reader, a Bluetooth sensor, an electromagnetic tracking device, an ultrasound tracking device, or other tracking device.

In the pictured embodiment, system 10 also includes a tomographic imaging device, such as an intraoperative computerized tomography (CT) scanner 41. Alternatively or additionally, processing system 50 may access or otherwise receive tomographic data from other sources; and the CT scanner 41 itself is not necessarily an essential part of the present system 10 (e.g., it is optional). Regardless of the source of the tomographic data, processor 32 computes a transformation over the ROI so as to register the tomographic images with images and information (e.g., a depth map) that are displayed on head-mounted display unit 28. The processor 32 can then apply this transformation in presenting at least a part of the tomographic image on see-through display 30 in registration with the ROI viewed through the see-through display 30. In the disclosed technique, the processor 32 can generate from the tomographic images, collectively named 3D image, a 3D model, and register the 3D model with the ROI, e.g., viewed through the see-through display 30.

In accordance with several implementations, in order to generate and present an augmented reality image on see-through display 30, processor 32 computes the location and orientation of head-mounted display unit 28 with respect to a portion of the body of patient 20 (e.g., the patient's back or a portion thereof). In some embodiments, processor 32 also computes the location and orientation of tool 22 with respect to the patient's body. In one embodiment, a processor which is integrated within the head-mounted display unit 28, may perform these functions or a portion of these functions. Alternatively or additionally, processor 32, which is disposed externally to the head-mounted display unit 28 and which may be in wireless communication with the head-mounted display unit 28, may be used to perform these functions or a portion of these functions. Processor 32 can be part of processing system 50, which additionally includes an output device 52 (e.g., a display, such as a monitor) for outputting information to an operator of the system, memory, and/or an input device 54 (such as a pointing device, a keyboard, a mouse, a trackpad, a pedal or touchscreen display, etc.) to allow the operator (e.g., professional 26 or an assistant to professional 26) to input data into the system 10.

In general, in the context of the present description, when a computer processor is described as performing certain steps, these steps may be performed by external computer processor 32 and/or a computer processor that is integrated within the head-mounted display unit 28. The processors described herein (e.g., processor 32) may include a single processor or multiple processors (e.g., parallel processors running in parallel to reduce computing time). If multiple processors are used, they may be communicatively coupled to each other over a network (e.g., wired or wireless communications network). The processor or processors carry out the described functionality under the control of suitable software, which may be downloaded to system 10 in electronic form, for example over a network, and/or stored on tangible, non-transitory computer-readable media, such as electronic, magnetic, or optical memory. In some embodiments, processing system 50 may be integrated in head-mounted display unit 28. In some embodiments, system 10 may include a see-through and/or augmented reality display which is not head-mounted. In such systems the display may be mounted to patient 20 or to the operating table and positioned such that professional 26 may be able to view patient 20 anatomy and/or operation site through at least a portion of the display. The display position may be adjustable.

In some embodiments, the 3D image, 3D rendering and 3D model of the present disclosure may be displayed while allowing user interaction as described herein on a display which is not a see-through display and/or a head-mounted display, such as a display of a workstation, a personal computer, a terminal, a tablet or a mobile device.

Visualizing a 3D Medical Image

Figure 2:
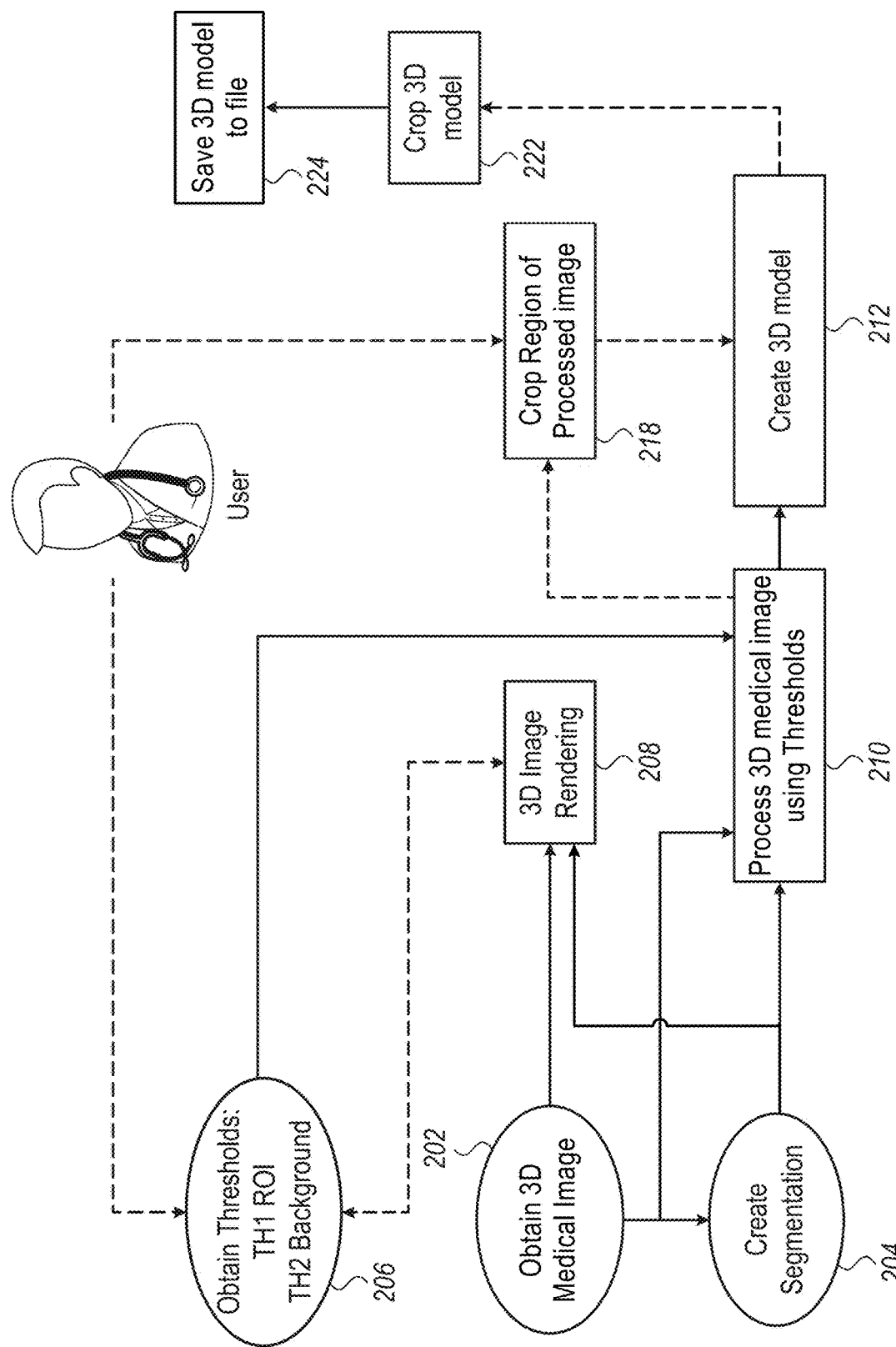
FIG. 2 is a flowchart of steps performed to generate a 3D rendering and/or a 3D model based on a 3D medical image of at least a portion of a body of a patient, in accordance with an embodiment of the disclosure.

FIG. 2 is a flowchart of steps performed to visualize a 3D medical image of a portion of a body of a patient, in accordance with an embodiment of the disclosure. The process can run automatically without user input, by one or more processors running all of the steps. Optionally, a user, such as the professional 26, may give input in thresholds obtaining step 206 and/or optical image cropping step 218, as described below. In some embodiments, the processor can be more than one processor, such that various steps are performed by different processors or processing units. In some embodiments, a single processor runs all of the steps. Thus, when a processor is mentioned herein, it may be referring to a single processor or multiple processors or processing units.

The process begins by the processor obtaining a 3D medical image (e.g., a CT scan) of a volume of the body portion, at a medical image obtaining step 202.

In general, e.g., depending on the clinical application, various medical image formats or modalities may be considered, such as MRI, PET or ultrasound images. In the contexts of this disclosure, the term "obtaining" may refer to, inter alia, acquiring, receiving, and/or accessing the 3D image and does not necessarily require the system to include the imaging device and/or the method to include the image acquiring operation or step.

Next, the processor segments the medical image to delineate at least one ROI (e.g., a spine section or region) from the rest of the imaged volume, at an image segmentation step 204. Various segmentation methods may be used, such as one that uses a trained convolutional neural network (CNN, such as U-net or V-net).

In some embodiments, a 3D image of the spine is segmented into spinal regions (e.g., cervical, thoracic, lumbar, sacral). In some embodiments, a 3D image of the spine is segmented into individual 3D vertebrae. In some embodiments, a 3D image of the spine is further segmented to indicate anatomical regions or portions of a vertebra (for example, spinous process, articular processes, transverse processes, vertebral body, centrum, posterior vertebral arch or neural arch). Bones other than the bones of the spine or other tissue may also be segmented into various regions, into individual components, and/or into anatomical portions of individual components. Such segmentation, although requiring more computation resources, may provide a better segmentation of the spine or any other such complex structure. This segmentation operation can advantageously be carried out by deep learning techniques, using one or more trained CNNs. The sacrum and ilium may be segmented in this manner, as well, using a separate neural network from the neural network used for the vertebrae or the same neural network.

In some embodiments, a combination of three networks may be used for this purpose. The networks are fully convolutional networks, e.g., based on the U-Net architecture.

The processor may obtain at least one ROI threshold and background threshold levels or values, TH1 ROI and TH2 background, respectively, at thresholds obtaining step 206. Examples of different ROI intensity threshold and background intensity threshold levels used are described in connection with FIGS. 3A-3C below. In the examples given by FIGS. 3A-3C, the ROI and background thresholds are HU thresholds that govern CT 3D visualization of mainly bone and metal. In these figures, of an orthopedic application concerning a spine, the main aim of the background threshold is to visualize metal elements that are in the background section (e.g., external to the spine) such as clamps and retractors without adding irrelevant or undesired information (e.g., background noise, such as noisy voxel levels, having a radiodensity value which does not satisfy the background threshold).

In another example, relevant to another medical application, the ROI and background thresholds can be MM intensities set to optimize, for example, an MRI 3D visualization of a joint or of at least a portion of a brain. In other embodiments, to, for example, distinguish between multiple tissue types, two or more (e.g., multiple) ROI thresholds can be defined and used together with the background threshold in segmentation, rendering a 3D image and/or generating a 3D model.

Figure 3A:
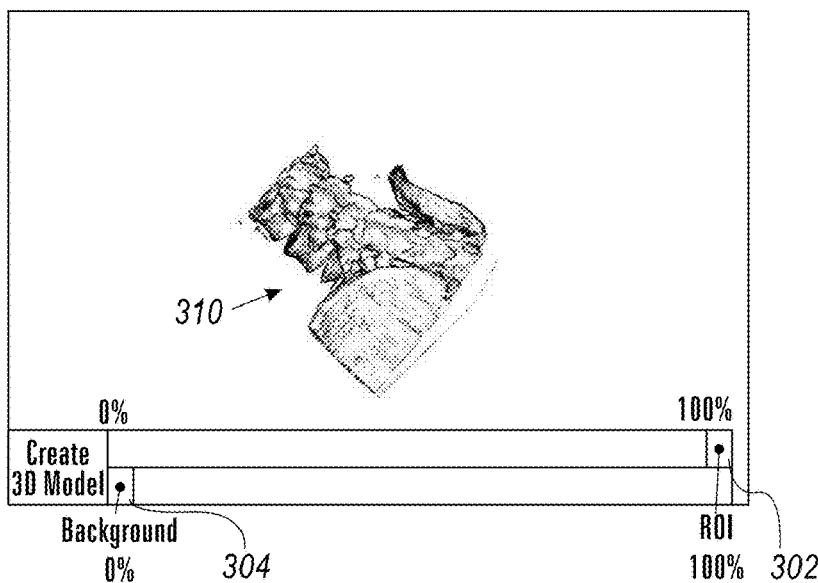
FIGS. 3A-3C show graphical user interface displays that include 3D renderings based on processed 3D images that facilitate the determination of feature thresholds used for computing respective 3D models, in accordance with embodiments of the disclosure.
Figure 3B:
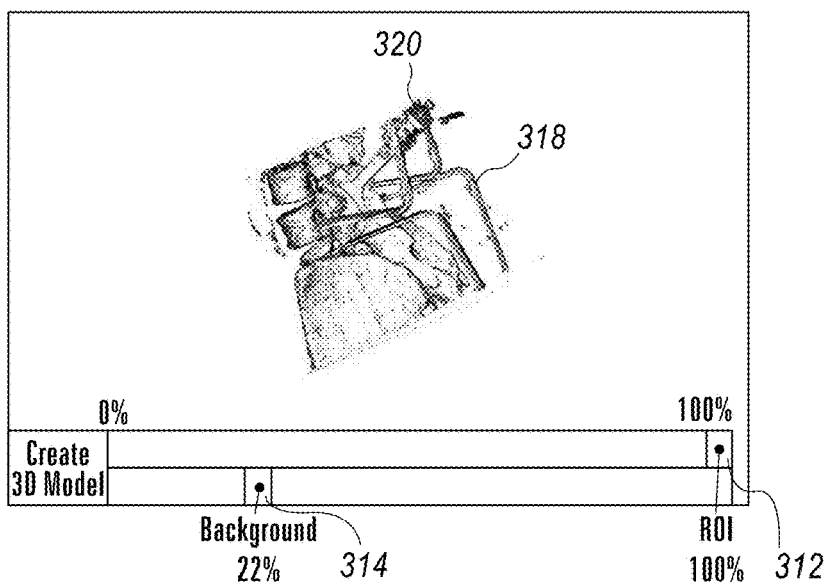
Figure 3C:
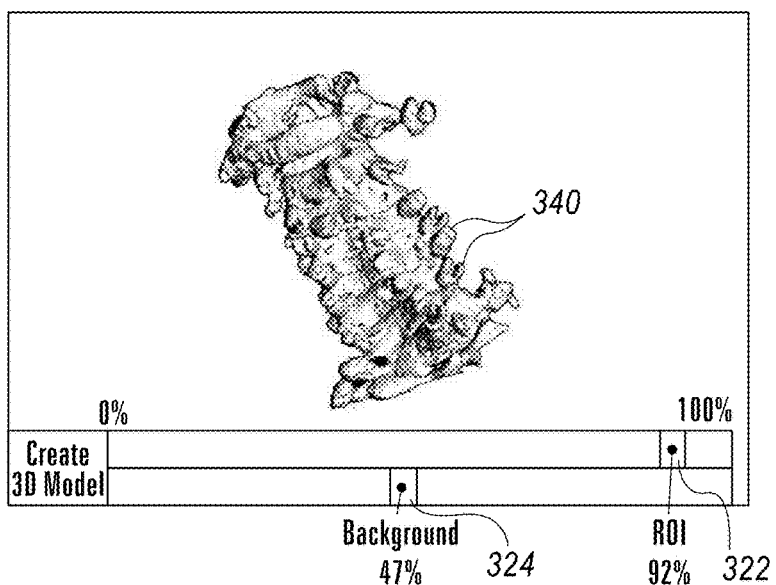

In an image processing step 210, the processor utilizes the segmentation and/or the thresholds to generate a processed 3D image. The processing may include reducing the feature values of voxels classified as background voxels having feature values which satisfy the ROI feature threshold value but do not satisfy the background feature threshold value. Thus, a 3D model generated based on the processed image (e.g., image with altered feature values) and the ROI feature threshold may visualize tissue features inside ROIs (e.g., bone tissue) when irrelevant or undesired background information is suppressed The processed 3D image of image processing step 210 may be used by the processor for computing a 3D model, at a 3D model creation step 212. At 3D model creation step 212, the processor, in some embodiments, runs a 3D model generation application (e.g., a surface building algorithm), such as a marching cubes algorithm described by Lorensen E. and Harvey E. in a paper titled, "Marching cubes: A high resolution 3D surface construction algorithm," published in ACM SIGGRAPH Computer Graphics, Volume 21 (4): 163-169, July 1987, the content of which is incorporated herein by reference. As described above, the marching cubes algorithm may use a threshold value, e.g., the lowest TH ROI value, to generate the 3D model. In some embodiments, the 3D model comprises a surface of an anatomy in the ROI (e.g., spine) and possibly comprising artificial elements as well, depending on TH ROI and TH background threshold settings. An example of a generated 3D model is shown in FIGS. 3A-3C, described below.

Figure 4:
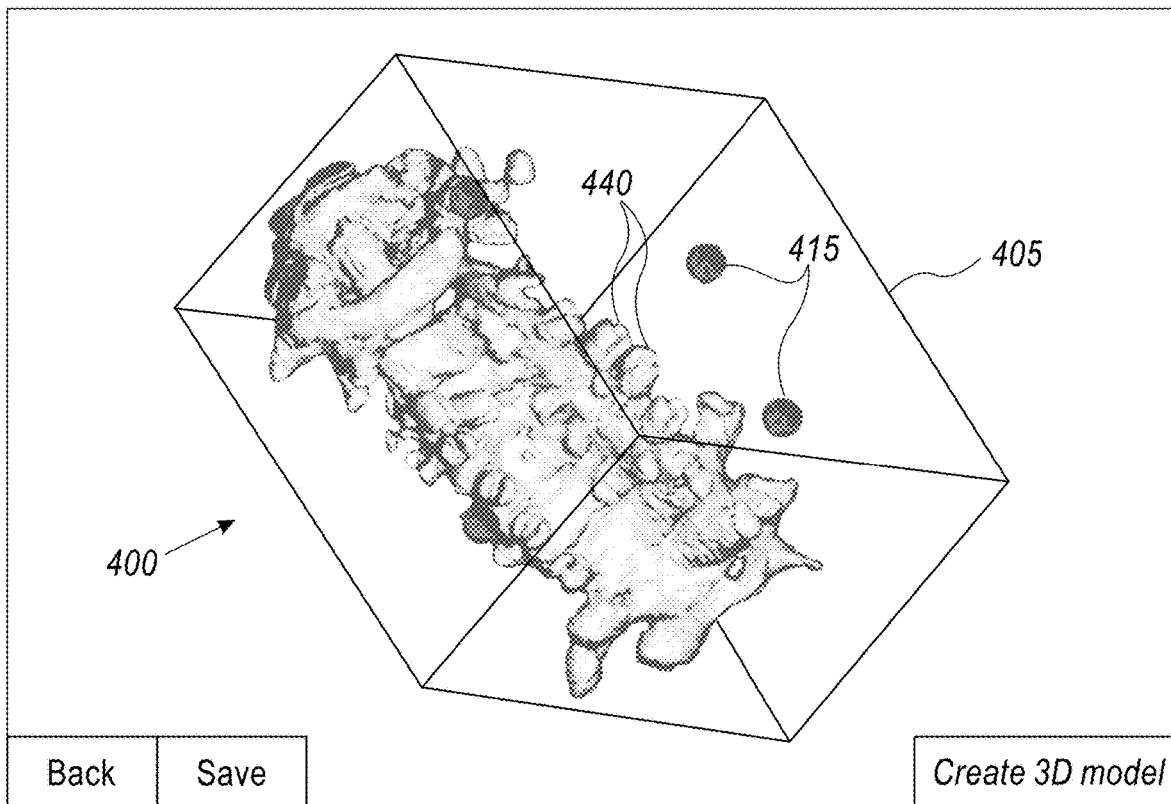
FIG. 4 is a graphical user interface display that includes a generated 3D model of a volume of interest of a patient, the 3D model computed based on the 3D image used to generate the 3D rendering of FIG. 3C, in accordance with an embodiment of the disclosure.

3D model cropping step 222 and 3D model saving step 224 include generating a suitable file of the 3D model, to be used, for example, with a near eye display (e.g., of head-mounted display unit 28) in image-guided surgery and/or with any other display such as a work station display. In an optional 3D model cropping step 222, the processor may define or may receive a definition (e.g., via user input) of a cropping box, such as shown in FIG. 4, and may crop the 3D model accordingly. Finally, the processor saves the 3D model (e.g., cropped 3D model) into a file of a suitable format (e.g., PLY format), in a memory, to be later uploaded to the processor or any other processor (e.g., a dedicated processor of a near-eye display of a head-mounted display unit 28).

In optional 3D image rendering step 208, the 3D image obtained medical image obtaining in step 202 is displayed on a monitor as a 3D visualization (e.g., a 3D volume rendering). A user, such as a medical professional can optimize the 3D visualization for the required or desired medical application (e.g., for spine image-guided surgery) by adjusting the two feature thresholds obtained (e.g., received, uploaded, etc.) in thresholds obtaining step 206. According to some embodiments, the initial 3D rendering is performed based on predetermined default values for the TH1 ROI and TH2 Background. According to some embodiments, the thresholds may be iteratively adjusted by the user. Final threshold values may be set or determined, for example, once a user input indicating that the threshold adjustment process is complete or a user request for generating of the 3D model is received.

In optional image cropping step 218, the processed 3D image obtained in image processing step 210 is displayed on a monitor so that the user can crop the portion of processed 3D image inputted for the modeling step (e.g., instead of the processor performing this step as part of, for example, image processing step 210). According to some embodiments, the cropping may be performed following optional 3D image rendering step 208 or in the frame of optional 3D image rendering step 208 and/or prior to image processing step 210.

In an additional optional step (not illustrated), the generated 3D model is displayed on a display (e.g., a stationary display such as a workstation and/or a near-eye display of head-mounted display unit 28) for the user's review.

The flowchart of FIG. 2 is presented by way of example and is simplified for clarity of presentation. The process may include additional or alternative steps, such as generating a 3D model from another imaging modality (e.g., based on a volume rendering obtained using ultrasound or MRI or fluoroscopy), or directly from high resolution segmentation, skipping the step of volume rendering, as described above.

FIGS. 3A-3C are exemplary Graphical User Interface (GUI) displays showing 3D renderings based on processed CT images (e.g., segmented CT images) of a spine that can be used for selecting or determining optimal or desired ROI intensity threshold and background intensity threshold for computing the 3D model, in accordance with embodiments of the disclosure. The 3D renderings may be viewed by a user that can determine or adjust the two thresholds of the thresholds obtaining step 206 above. The user may set or adjust the ROI and background intensity thresholds by adjusting a GUI element, such as sliding ROI TH sliders (302, 312, 322) and background TH sliders (304, 314, 324), respectively, at the bottom of the 3D rendering screen, respectively. The 3D rendering will change in correspondence to the change in thresholds and based on the segmentation, visualizing the data that will be included in the 3D model for each selection of thresholds or for each selected combination of thresholds. The user may then optimize the visualization or rendering while the thresholds values for the optimized or desired rendering will be provided as input to the 3D image processing and/or modeling. In FIGS. 3A-3C, the value of a threshold increases as the threshold slider is slid to the left. The slider may be moved by touching and dragging on the screen and/or by use of a computer mouse, keyboard, joystick, voice-activated control, or other input device.

FIG. 3A is a graphic display of a rendering 310 of a 3D image with threshold sliders set as follows: ROI TH slider 302 at 100%, meaning ROI intensity TH value=min scan radiodensity value and all is shown within the segmented area, and background threshold slider 304 at 0%, meaning background intensity TH value=maximum scan radiodensity value and all information outside the segmented portion is blocked.

FIG. 3B is a graphic display of a rendering of a 3D image with threshold sliders set as follows: ROI threshold slider 312 is set at 100%, meaning ROI intensity TH value=minimum scan radiodensity value and all tissue is shown within segmented portion. Background threshold slider is set at 22%, meaning background intensity TH value is high but such that metal retractors 318 and clamp 320 outside the segmented spine are shown.

FIG. 3C is a graphic display of a rendering of a 3D image with threshold sliders set as follows: ROI threshold slider is set at 92%, meaning ROI intensity TH value=low scan radiodensity value and most tissue is shown within segmented portion. Background threshold slider is set at 47%, meaning background intensity TH value is of mid value but such that the heads of metal screws 340 implanted in the bone protruding from the spine are shown.

Due to the relatively large background threshold, e.g., that is set at about the middle of the intensity range, irrelevant or undesired signals in the background, such as image noise and soft and bone tissue are not shown, making the disclosed processed 3D image particularly well visualizing the ROIs only.

In some embodiments, in generating the rendering, the one or more ROI feature thresholds would be applied to the one or more ROIs respectively while the background feature threshold would be applied only to the background portion of the image.

In some embodiments, as illustrated in FIGS. 3A-3C, when generating the rendering, the one or more ROI feature thresholds would be applied to the one or more ROIs respectively, while the background feature threshold would be applied to the entire image (i.e., including the one or more ROIs). In such a case, in the one or more ROIs, rendering may be performed based on the lowest threshold applied (i.e., the lowest of the respective ROI feature threshold and the background feature threshold). In such embodiment, the user may view a rendering or visualization of the medical image without the effect of the segmentation by simply setting the background feature threshold to a value lower than or equal to the one or more ROI feature thresholds. Following that, a single feature threshold value would apply to the entire scan or image without a distinction between different portions of the image (e.g., ROI vs. background).

FIG. 4 is a graphical user interface display showing a 3D model 400 of a volume of interest, the 3D model 400 computed based on processed 3D image of FIG. 3C, in accordance with an embodiment of the disclosure. As seen, the 3D model 400 is located inside a box 405 having marked facets 415. The disclosed 3D model clearly presents a spine section implanted with metal screws 440 with clean background (e.g., empty of, or without, irrelevant or undesired information). Such 3D model is suitable for presentation and/or augmentation with the optically viewed (e.g., with the near-eye display device) anatomical portion of the patient.

Figure 5:
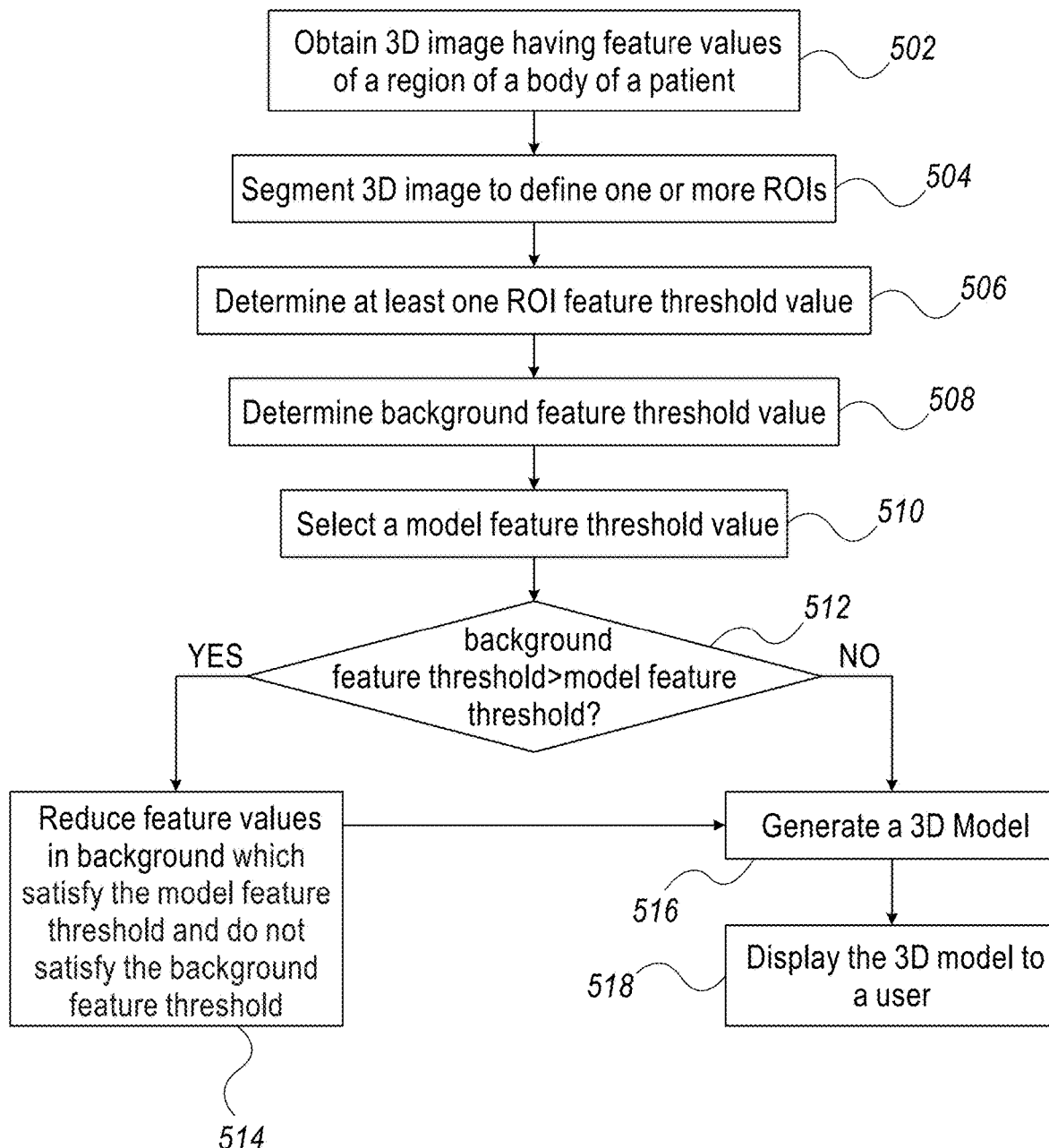
FIG. 5 is a flowchart of steps performed to generate a three-dimensional (3D) model based on a 3D image of a portion of a body of a patient using a selected threshold value, in accordance with an embodiment of the disclosure.

FIG. 5 is a flowchart of steps performed to generate a three-dimensional (3D) model based on a 3D image of a portion of a body of a patient using selected threshold values, in accordance with an embodiment of the disclosure. The method according to the presented embodiment carries out a process that begins with obtaining a 3D medical image having feature values, of at least a portion of an organ or anatomy of a patient (e.g., an entire spine or region of a spine, such as a lumbosacral region, a cervical region, a thoracic region, and/or a sacroiliac region), at a 3D medical image receiving step 502. The features may be directly extracted from the medical image, as in the case the feature is intensity, or may require an additional operation of processing or computation, for example, as in the case the feature is gradients. The 3D medical image may be obtained, for example, via provided input, uploaded or downloaded via the internet. In some embodiments the 3D image may be obtained by capturing the medical image via a medical imaging device.

Next, a processor segments the 3D medical image to define one or more ROIs (e.g., portions of spine regions), at 3D medical image segmentation step 504.

At a ROI feature threshold value determination step 506, the processor determines at least one ROI features threshold, such as image intensity threshold value. At a background feature threshold value determination step 508, the processor determines a background features threshold, such as image background intensity threshold value.

The determination of the at least one ROI feature threshold and of the background feature threshold of ROI feature threshold value determination step 506 and background feature threshold value determination step 508 may include receiving input values (e.g., from the user) for the at least one ROI feature threshold or for the background feature threshold or for both. In some implementations, the receiving of the input values from the user comprises generating a GUI element to be displayed to the user, such as ROI TH sliders 302, 312, 322 and background TH sliders 304, 314, 324 of FIGS. 3A-3C. The GUI element may allow the user to adjust the input values, while the 3D rendering and displaying of the 3D rendering to the user are iteratively performed in correspondence to the user adjustment of the input values. In some embodiments, the one or more ROI feature thresholds and the background feature threshold are predetermined. In some embodiments, a default value for some or for each of the one or more ROI feature thresholds and the background feature threshold is predetermined. A 3D rendering based on these default values may be displayed to the user as a default 3D rendering. The user may then adjust the thresholds values as described above.

At model feature threshold value selection step 510, the processor selects or determines the threshold to be input to a 3D model generation algorithm based on the determined one or more ROI feature thresholds and the background feature threshold. In some embodiments, the lowest ROI feature threshold may be selected or determined as the input threshold for the 3D model generation. In some embodiments, the lowest of the one or more ROI feature thresholds and the background feature threshold may be selected.

At threshold values checking step 512, the processor checks if the background feature threshold value is greater than the threshold value selected to be provided to the 3D model generation algorithm (model feature threshold value selection step 510 above).

If the result of the check performed in threshold values checking step 512 is positive, i.e., the background feature threshold value is greater than the threshold value selected in model feature threshold value selection step 510, then selected feature values in the background (e.g., feature values associated with voxels segmented as background (3D) medical image segmentation step 504 above)) are reduced or suppressed in a step 514. Background feature values which satisfy the model generation threshold (i.e., the threshold selected to be input to the 3D model generation algorithm in model feature threshold value selection step 510 above) but do not satisfy the background feature threshold are reduced to a value equal to or below the model generation threshold. In some embodiments, such background feature values are reduced to a value equal to the value of the model generation threshold minus a constant. Thus, background elements (e.g., voxels) having feature values which do not satisfy the background feature threshold, are not considered for the model generation, or excluded from being included in the model generation algorithm input.

At a step 516, a 3D model is generated by a model generation algorithm that accepts a single 3D image feature threshold value selected at model feature threshold value selection step 510. An example of such a model is the aforementioned marching cubes algorithm.

Finally, the processor displays (or generates an output for display) the generated 3D model to the user, at a 3D model displaying step 518.

The flowchart of FIG. 5 is presented by way of example and is simplified for clarity of presentation. The process may include alternative steps, such as determining threshold values that are from different medical modalities.

FIGS. 6A-6D are example GUI displays 600 that include various views of a patient's spine, in accordance with an embodiment of the disclosure. FIGS. 6A-6D show an illustration of image data displayed during a medical procedure for inserting pedicle screws into a patient's spine. The image data include a display of a 3D model or rendering 601 of an ROI (e.g., a portion of the patient's spine), and virtual images of a tool 602 and a pedicle screw implant 604. In some embodiments, 3D model 601 may be generated as disclosed hereinabove. The GUI displays 600 in FIGS. 6A-6D further include various views, represented as images, of the patient spine and pedicle screw implant 604: X-ray lateral view 606, X-ray anteroposterior (AP) view 608, 3D lateral view 610 and 3D AP view 612, displayed in different combinations.

The displays shown in FIGS. 6A-6D are not augmented-reality displays and may be displayed, for example, on a workstation. However, these displays may be displayed in a see-through display of a wearable, hands-free and/or head-mounted display system while 3D model 601 is overlaid on the patient anatomy, optionally in-alignment, and as described hereinabove. The different views (606, 608, 610 and/or 612) may be displayed on a different section of the see-through display, e.g., in a top portion or a side portion of the display and such that they will not interfere with the user's view (e.g., direct see-through view) of the physical ROI through the display.

A user may select which view will be presented in each view display window, such as windows 614 and 616. The different views may be presented in the GUI display, for example, via a drop-down menu, such as drop-down menu 618, associated with each view display window. The GUI display 600 shown in FIGS. 6A-6D includes two view display windows. Other embodiments may include a different number of view display windows. In some embodiments, the user may select which view to display in which view display window (e.g., via a drop-down menu) and switch between the views during the procedure, as desired. Accordingly, the user may generate different combinations of views during the procedure, allowing him or her to receive maximal and proper information for each maneuver, occurrence and/or phase of the procedure.

X-ray views 606 and 608 are X-ray like images or virtual X-ray images derived from the 3D medical image as viewed from a fixed position, specifically lateral and AP respectively. Lateral and AP X-ray like or virtual X-ray views may facilitate navigation while AP view may allow, for example, symmetric screw insertion planning (e.g., during minimally invasive surgical (MIS) procedures). The virtual X-ray images may be generated by the processor from the 3D medical image by generating digitally reconstructing radiographs. In some embodiments, the processor may utilize the segmentation to digitally reconstruct radiographs from the segmented 3D medical image. The voxel feature values segmented as background (i.e., not ROI) may be set to zero, thus generating X-ray views of the ROI only (e.g., without noise or with reduced noise), as shown, for example, in FIGS. 6A-6D. In some embodiments, a GUI element such as slider 620 may be generated to allow the user to adjust the DRR images visibility threshold (e.g., sum of voxels intensity values). Each change of visibility threshold may cause the processor to generate a new DRR based on the adjusted visibility threshold.

In some embodiments, X-ray views 606 and 608 may display 2D X-ray images of the patient anatomy captured by an X-ray imaging device such as a fluoroscope. In some embodiments, the X-ray images may be registered with the 3D medical image.

3D views 610 and 612 display the 3D model as viewed from a fixed position, specifically lateral and AP respectively. The 3D view may facilitate visualization and orientation and may simplify entry point location.

Although FIGS. 6A-6D show X-ray views and 3D views from lateral and AP points of view, other points of view or angles of view may be displayed alternatively or additionally. It should be noted that lateral and AP points of view may be specifically advantageous for medical procedures or interventions which the professional may perform via a lateral approach (e.g., by positioning the patient on the side of his body), such as a Lateral Lumbar Interbody Fusion (LLIF) procedure.

Figure 6A:
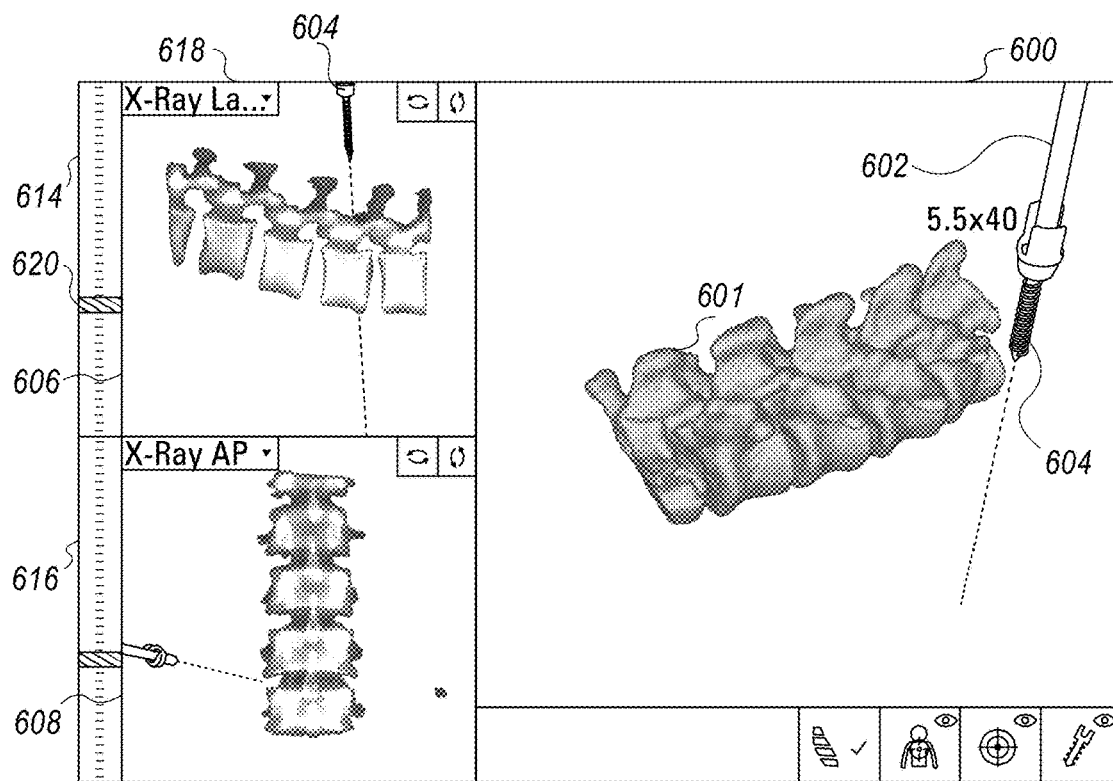
FIGS. 6A-6D are example graphical user interface displays that include various views of a patient's spine, in accordance with an embodiment of the disclosure.
Figure 6B:
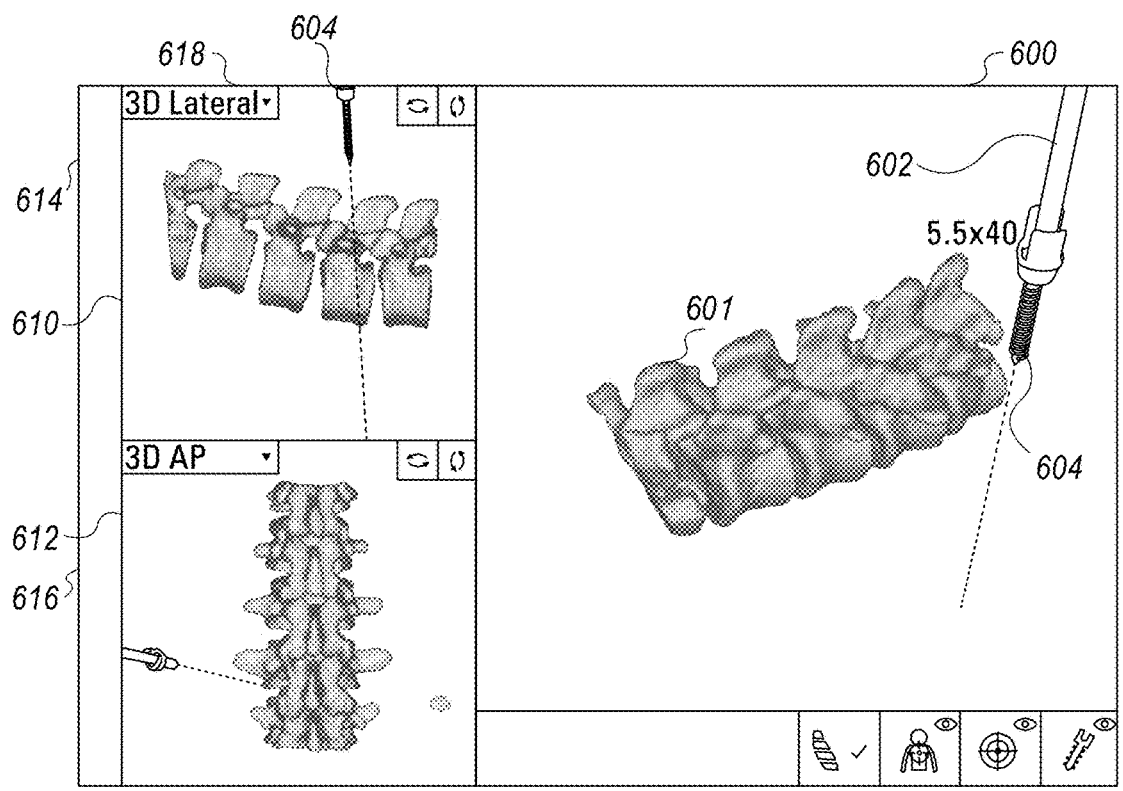
Figure 6C:
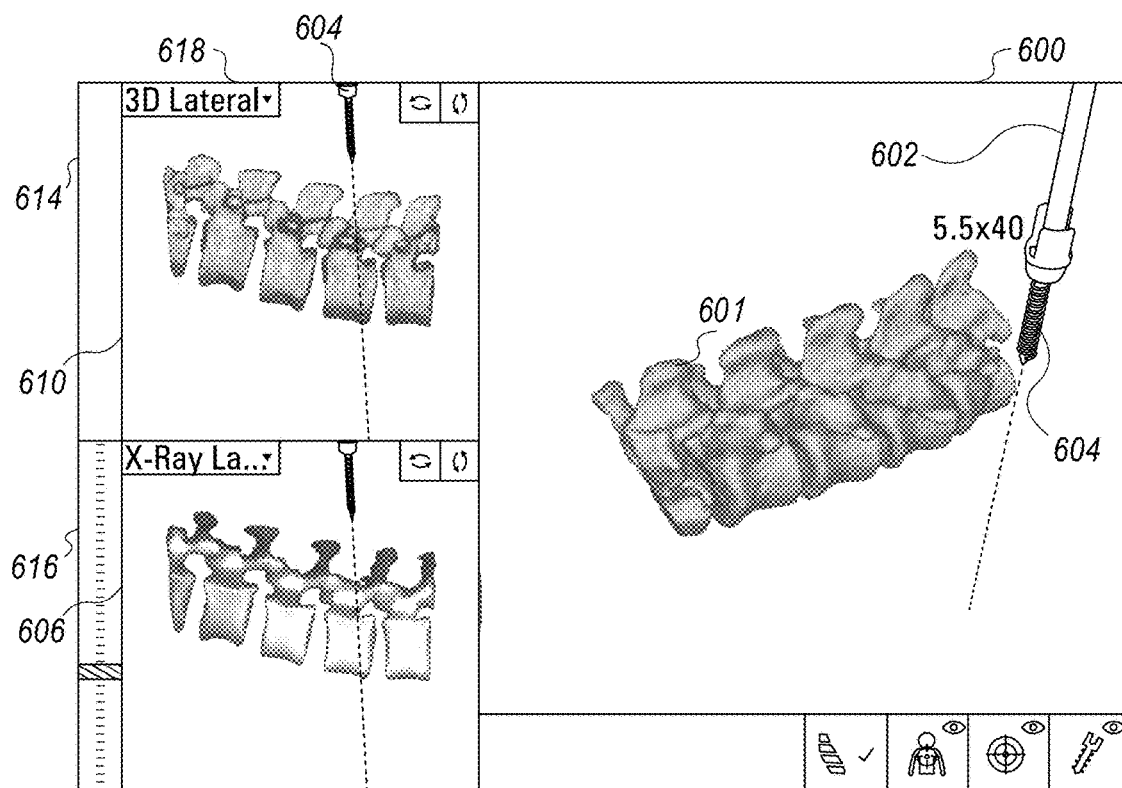
Figure 6D:
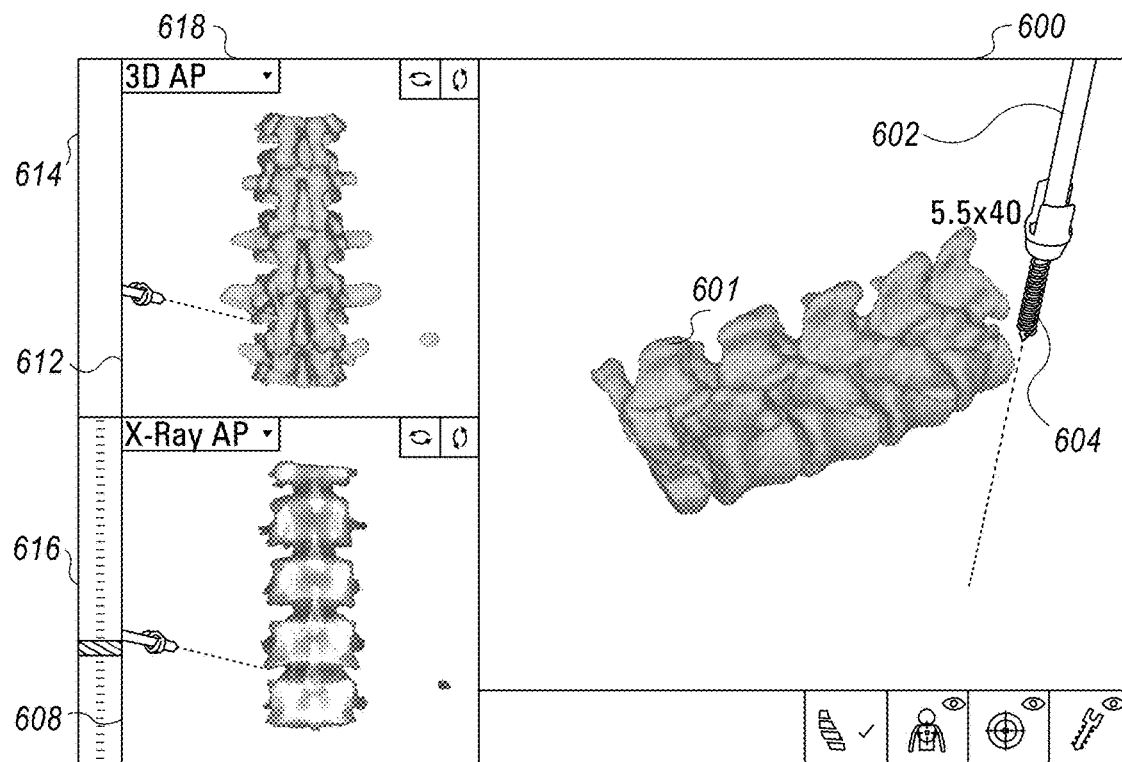

In some embodiments, as indicated above, the user may select which views will be displayed in each window of the display, such as windows 614 and 616. FIGS. 6A-6D show such various combinations which may be advantageous to the user during a medical procedure or intervention (e.g., surgical or non-surgical therapeutic or diagnostic procedure). FIG. 6A shows a combination of X-ray views 606 and 608 from different points of view, specifically lateral and AP. FIG. 6B shows a combination of 3D views 610 and 612 from different points of view, specifically lateral and AP. FIG. 6C shows a combination of lateral views 606 and 610 via different types of view (e.g., imaging modalities or techniques), specifically X-ray and 3D, respectively. FIG. 6D shows a combination of AP views 608 and 612 via different types of view, specifically X-ray and 3D, respectively. It should be noted that 3D view may provide surface-related data of a bone structure, while X-ray view may provide depth-related data of the bone structure. Displaying a specific type of view, e.g., X-ray view or 3D view, from multiple points of view or a specific point of view, e.g., lateral or AP, via different types of view at the same time may be advantageous and may facilitate the procedure or intervention or even better the procedure or intervention outcome by providing the required information and/or more information and better visualization of the ROI to the professional performing the procedure or intervention.

While images of views 606, 608, 610 and 612 are static, virtual images of the tool 602 and screw implant 604 may be dynamically augmented on images of views 606, 608, 610 and 612 presenting the actual location and navigation of the tool and/or screw implant with respect to the patient anatomy. Such display may be facilitated via a tracking system and as described hereinabove. Since screw implant 604 is attached as a straight extension to tool 602 and since its dimensions may be predefined, there is no need for tracking of screw implant 604 and tracking of only tool 602 may suffice.

In some embodiments, the GUI may include one or more slice views of the 3D medical image. In some embodiments, a sagittal slice view and an axial slice view may be generated and displayed. A virtual image representing a tool and/or a virtual image representing an implant, such as a pedicle screw may be augmented on the slice views, while navigated by a professional during a medical procedure or intervention. In some embodiments, the displayed slice may be selected and/or generated based on or according to the position of the navigated tool. In some embodiments, the displayed slice may be selected and/or generated such that a predefined axis of the tool is aligned with the slice plane. For example, for an elongated tool, such as a screwdriver, the tool longitudinal axis may be predefined as the tool axis. Thus, for each tracked and/or recorded change of position of the tool a new slice may be generated and displayed.

In some embodiments, for each anatomical view only slices of the specific anatomical view would be generated and displayed in response to the manipulation of the tool. For example, for an axial view, only axial slices would be displayed according to the axial component of the tool current position. In some embodiments, in one or more anatomical views, slices may be generated based on tool movement in two or three anatomical planes. For example, in an axial view, for a current position of the tool having components in the axial and coronal planes, a slice positioned axially and coronally in accordance with the axial and coronal tool position, would be generated and displayed. As another example, in an axial view, for a current position of the tool having components in the axial, coronal and sagittal planes, a corresponding slice would be generated for the axial view. Thus, for example, for a tool positioned in a sagittal plane, the axial slice view and the sagittal slice view may be similar or even identical. Such anatomical slice view which allows slice generation in multiple plains and not just in the predefined view plane provides better visualization and may facilitate navigation.

In some embodiments, the display of the various views may be manipulated by a user. In some embodiments a view may be mirrored, e.g., with respect to an anatomical plane of the patient. For example, a mirroring command button may be included in the GUI. Mirroring of a lateral view may be performed, for example, with respect to a plane of the patient body. In some embodiments, the view may be rotated by a specific angle, e.g., by 180°, with respect to an anatomical axis, for example. Such rotating may be performed by pressing a dedicated command button generated as part of the GUI, for example. Specifically, such rotating of an AP view may provide a view rotated by 180° with respect to the longitudinal anatomical axis (i.e., head to toe). Such manipulation may be advantageous, for example, when the medical image and its derived images are displayed from a side opposite to the desired side (e.g., left side or right side of the patient or upper side or lower side of the patient). In some embodiments, the various views may be panned and zoomed in and out, e.g., via dedicated command buttons generated as part of the GUI.

While examples of the disclosed technique are given for body portion containing spine vertebrae, the principles of the system, method, and/or disclosure may also be applied to other bones and/or body portions than spine, including hip bones, pelvic bones, leg bones, arm bones, ankle bones, foot bones, shoulder bones, cranial bones, oral and maxillofacial bones, sacroiliac joints, etc.

The disclosed technique is presented with relation to image-guided surgery systems or methods, in general, and accordingly, the disclosed technique of visualization of medical images should not be considered limited only to augmented reality systems and/or head-mounted systems. For example, the technique is applicable to the processing of images from different imaging modalities, as described above, for use in diagnostics.

The terms "top," "bottom," "first," "second," "upper," "lower," "height," "width," "length," "end," "side," "horizontal," "vertical," and similar terms may be used herein; it should be understood that these terms have reference only to the structures shown in the figures and are utilized only to facilitate describing embodiments of the disclosure. Various embodiments of the disclosure have been presented in a range format. It should be understood that the description in range format is merely for convenience and brevity and should not be construed as an inflexible limitation on the scope of the disclosure. The ranges disclosed herein encompass any and all overlap, sub-ranges, and combinations thereof, as well as individual numerical values within that range. For example, description of a range such as from about 5 to about 30 degrees should be considered to have specifically disclosed subranges such as from 5 to 10 degrees, from 10 to 20 degrees, from 5 to 25 degrees, from 15 to 30 degrees etc., as well as individual numbers within that range (for example, 5, 10, 15, 20, 25, 12, 15.5 and any whole and partial increments therebetween). Language such as "up to," "at least," "greater than," "less than," "between," and the like includes the number recited. Numbers preceded by a term such as "about" or "approximately" include the recited numbers. For example, "approximately 2 mm" includes "2 mm." The terms "approximately", "about", and "substantially" as used herein represent an amount close to the stated amount that still performs a desired function or achieves a desired result.

In some embodiments, the system comprises various features that are present as single features (as opposed to multiple features). For example, in one embodiment, the system includes a single HMD, a single camera, a single processor, a single display, a single fiducial marker, a single imaging device, etc. Multiple features or components are provided in alternate embodiments.

In some embodiments, the system comprises one or more of the following: means for imaging (e.g., a camera or fluoroscope or MRI machine or CT machine), means for calibration or registration (e.g., adapters, markers, objects), means for fastening (e.g., anchors, adhesives, clamps, pins), etc.

The processors described herein may include one or more central processing units (CPUs) or processors or microprocessors. The processors may be communicatively coupled to one or more memory units, such as random-access memory (RAM) for temporary storage of information, one or more read only memory (ROM) for permanent storage of information, and one or more mass storage devices, such as a hard drive, diskette, solid state drive, or optical media storage device. The processors (or memory units communicatively coupled thereto) may include modules comprising program instructions or algorithm steps configured for execution by the processors to perform any of all of the processes or algorithms discussed herein. The processors may be communicatively coupled to external devices (e.g., display devices, data storage devices, databases, servers, etc. over a network via a network communications interface.

In general, the algorithms or processes described herein can be implemented by logic embodied in hardware or firmware, or by a collection of software instructions, possibly having entry and exit points, written in a programming language, such as, for example, Python, Java, Lua, C, C #, or C++. A software module or product may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, or any other tangible medium. Such software code may be stored, partially or fully, on a memory device of the executing computing device, such as the processing system 50, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules but may be represented in hardware or firmware. Generally, any modules or programs or flowcharts described herein may refer to logical modules that may be combined with other modules or divided into sub-modules despite their physical organization or storage.

The various features and processes described above may be used independently of one another or may be combined in various ways. All possible combinations and sub-combinations are intended to fall within the scope of this disclosure. In addition, certain method or process blocks or steps may be omitted in some implementations. The methods and processes described herein are also not limited to any particular sequence, and the blocks, steps, or states relating thereto can be performed in other sequences that are appropriate. For example, described blocks, steps, or states may be performed in an order other than that specifically disclosed, or multiple blocks or states may be combined in a single block or state. The example blocks, steps, or states may be performed in serial, in parallel, or in some other manner. Blocks, steps, or states may be added to or removed from the disclosed example embodiments. The example systems and components described herein may be configured differently than described. For example, elements may be added to, removed from, or rearranged compared to the disclosed example embodiments.

Any process descriptions, elements, or blocks in the flow diagrams described herein and/or depicted in the attached figures should be understood as potentially representing modules, segments, or portions of code which include one or more executable instructions for implementing specific logical functions or steps in the process.

It will be appreciated that the systems and methods of the disclosure each have several innovative aspects, no single one of which is solely responsible or required for the desirable attributes disclosed herein. The various features and processes described above may be used independently of one another or may be combined in various ways. The section headings used herein are merely provided to enhance readability and are not intended to limit the scope of the embodiments disclosed in a particular section to the features or elements disclosed in that section.

Certain features that are described in this specification in the context of separate embodiments also may be implemented in combination in a single embodiment. Conversely, various features that are described in the context of a single embodiment also may be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination. No single feature or group of features is necessary or indispensable to each and every embodiment.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

What is claimed is:

1. A computer-implemented method for improving display of 3D models in connection with image-guided surgery, the method comprising:

obtaining a three-dimensional (3D) computed tomography image of a region of a spine of a patient, the 3D computed tomography image having intensity values;

segmenting the 3D computed tomography image to define multiple regions of interest (ROIs) of the spine and a background region, wherein the background region comprises a portion of the 3D computed tomography image which is not an ROI;

determining, for each of the multiple ROIs of the spine, a ROI intensity threshold value that can be used as an input to control what portions of the ROI are included in a 3D rendering of the 3D computed tomography image;

determining a background intensity threshold value that can be used as an input to control what portions of the background region are included in the 3D rendering of the 3D computed tomography image;

generating the 3D rendering of the 3D computed tomography image, wherein the generation of the 3D rendering comprises:

in each of the multiple ROIs of the spine of the 3D computed tomography image, rendering based on intensity values of the ROI that satisfy a lowest threshold value of the determined ROI intensity threshold value and the determined background intensity threshold value; and in the background region of the 3D computed tomography image, rendering based on intensity values of the background region that satisfy the determined background intensity threshold value; and causing the 3D rendering to be output for display to a user, wherein the intensity threshold values are voxel values.

2. The computer-implemented method of claim 1, further comprising displaying the 3D rendering in alignment by performing registration of the 3D rendering with the region of the spine.

3. The computer-implemented method of claim 1, wherein the 3D rendering is a 3D model.

4. The computer-implemented method of claim 1, wherein the generating the 3D rendering comprises changing at least some of the intensity values of the 3D computed tomography image into a value which does not satisfy the lowest threshold value.

5. The computer-implemented method of claim 1, wherein the background region of the 3D computed tomography image comprises soft tissue.

6. The computer-implemented method of claim 1, further comprising:

repeatedly adjusting one or more of the ROI intensity threshold values and the background intensity threshold value according to input from a user; and repeatedly generating the 3D rendering of the 3D computed tomography image based on the adjusted values.

7. The computer-implemented method of claim 1, wherein the multiple ROIs of the spine comprise various regions of the spine.

8. The computer-implemented method of claim 1, wherein the multiple ROIs of the spine comprise individual vertebrae of the spine.

9. The computer-implemented method of claim 1, further comprising:

adjusting one or more of the ROI intensity threshold values and the background intensity threshold value according to input from a user;

regenerating the 3D rendering of the 3D computed tomography image based on the adjusted values; and generating a 3D model based on the adjusted values.

10. A computer-implemented method for improving display of 3D models in connection with image-guided surgery, the method comprising:

obtaining a three-dimensional (3D) image of a region of a spine of a patient, the 3D image having intensity values, segmenting the 3D image to define multiple regions of interest (ROIs) of the spine and a background region, wherein the background region comprises a portion of the 3D image which is not an ROI;

determining, for each of the multiple ROIs of the spine, a ROI intensity threshold value that can be used as an input to control what portions of the ROI are included in a 3D rendering of the 3D image;

determining a background intensity threshold value that can be used as an input to control what portions of the background region are included in the 3D rendering of the 3D image;

generating the 3D rendering of the 3D image, wherein the generation of the 3D rendering comprises:

in each of the multiple ROIs of the spine of the 3D image, rendering based on intensity values of ROI that satisfy a lowest threshold value of the determined ROI intensity threshold value and the determined background intensity threshold value; and in the background region of the 3D image, rendering based on intensity values of the background region that satisfy the determined background intensity threshold value; and causing the 3D rendering to be output for display to a user.

11. The computer-implemented method of claim 10, wherein the intensity values are voxel values of the 3D image.

12. The computer-implemented method of claim 10, wherein the 3D image is a computed tomography image or a magnetic resonance image.

13. The computer-implemented method of claim 10, further comprising displaying the 3D rendering in alignment by performing registration of the 3D rendering with the region of the spine.

14. The computer-implemented method of claim 10, wherein the 3D rendering is a 3D model.

15. The computer-implemented method of claim 10, wherein the generating the 3D rendering comprises changing at least some of the intensity values of the 3D image into a value which does not satisfy the lowest threshold value.

16. The computer-implemented method of claim 10, wherein the background region of the 3D image comprises soft tissue.

17. The computer-implemented method of claim 10, further comprising:

repeatedly adjusting one or more of the ROI intensity threshold values and the background intensity threshold value according to input from a user; and repeatedly generating the 3D rendering of the 3D image based on the adjusted values.

18. The computer-implemented method of claim 10, further comprising:

adjusting one or more of the ROI intensity threshold values and the background intensity threshold value according to input from a user;

regenerating the 3D rendering of the 3D image based on the adjusted values; and generating a 3D model based on the adjusted values.

19. The computer-implemented method of claim 10, wherein the multiple ROIs of the spine comprise various regions of the spine.

20. The computer-implemented method of claim 10, wherein the multiple ROIs of the spine comprise individual vertebrae of the spine.

* * * * *